US008916531B2

(12) United States Patent
Bennett et al.

(10) Patent No.: US 8,916,531 B2
(45) Date of Patent: Dec. 23, 2014

(54) MODULATION OF CD40 EXPRESSION

(75) Inventors: C. Frank Bennett, Carlsbad, CA (US); Lex M. Cowsert, New Braunfels, TX (US); Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 766 days.

(21) Appl. No.: 12/743,797

(22) PCT Filed: Nov. 20, 2008

(86) PCT No.: PCT/US2008/012998
§ 371 (c)(1),
(2), (4) Date: Feb. 15, 2011

(87) PCT Pub. No.: WO2009/067243
PCT Pub. Date: May 28, 2009

(65) Prior Publication Data
US 2011/0160283 A1 Jun. 30, 2011

Related U.S. Application Data

(60) Provisional application No. 60/989,421, filed on Nov. 20, 2007.

(51) Int. Cl.
C12N 15/113 (2010.01)

(52) U.S. Cl.
CPC ........ *C12N 15/1138* (2013.01); *C12N 2310/11* (2013.01); *C12N 2310/341* (2013.01); *C12N 2310/3341* (2013.01); *C12N 2310/321* (2013.01); *C12N 2310/346* (2013.01); *C12N 2310/315* (2013.01)
USPC ...................................... 514/44 A; 536/24.5

(58) Field of Classification Search
None
See application file for complete search history.

(56) References Cited

U.S. PATENT DOCUMENTS

| 3,687,808 | A | 8/1972 | Merigan |
|---|---|---|---|
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,762,779 | A | 8/1988 | Snitman |
| 4,789,737 | A | 12/1988 | Miyoshi et al. |
| 4,800,159 | A | 1/1989 | Mullis et al. |
| 4,806,463 | A | 2/1989 | Goodchild et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh Dinh et al. |
| 4,876,335 | A | 10/1989 | Yammane et al. |
| 4,904,582 | A | 2/1990 | Tullis |
| 4,948,882 | A | 8/1990 | Ruth |
| 4,958,013 | A | 9/1990 | Letsinger |
| 4,981,957 | A | 1/1991 | Lebleu et al. |
| 5,013,830 | A | 5/1991 | Ohtsuka et al. |
| 5,023,243 | A | 6/1991 | Tullis |
| 5,034,506 | A | 7/1991 | Summerton et al. |
| 5,075,302 | A | 12/1991 | Neustadt |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,134,066 | A | 7/1992 | Rogers et al. |
| 5,138,045 | A | 8/1992 | Cook et al. |
| 5,149,797 | A | 9/1992 | Pederson et al. |
| 5,166,315 | A | 11/1992 | Summerton et al. |
| 5,175,273 | A | 12/1992 | Bischofberger et al. |
| 5,177,196 | A | 1/1993 | Meyer, Jr. et al. |
| 5,177,198 | A | 1/1993 | Spielvogel et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,220,007 | A | 6/1993 | Pederson et al. |
| 5,223,618 | A | 6/1993 | Cook et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,256,775 | A | 10/1993 | Froehler |
| 5,258,506 | A | 11/1993 | Urdea et al. |

(Continued)

FOREIGN PATENT DOCUMENTS

| EP | 0514927 | 11/1992 |
|---|---|---|
| EP | 0650493 | 5/1995 |

(Continued)

OTHER PUBLICATIONS

U.S. Appl. No. 08/465,880, filed Jun. 6, 1995, Cook.
U.S. Appl. No. 08/368,037, filed Jun. 6, 1995, Cook et al.
U.S. Appl. No. 08/762,488, filed Dec. 1, 1996, Cook et al.
Agrawal, "Antisense oligonucleotides: towards clinical trials" Tibtech (1996) 14:376-387.
Albelda et al., "Adhesion molecules and inflammatory injury" FASEB J. (1994) 8:504-512.
Albert et al., "Antisense knockouts: molecular scalpels for the dissection of signal transduction" TiPS (1994) 15:250-254.
Altschul et al., "Basic Local Alignment Search Tool" J. Mol. Biol. (1990) 215:403-410.
Altschul et al., "Gapped BLAST and PSI-BLAST: a new generation of protein database search programs" Nucl. Acids Res. (1997) 25(17):3389-3402.

(Continued)

Primary Examiner — Tracy Vivlemore
(74) Attorney, Agent, or Firm — Isis Pharmacueticals, Inc. Patent Dept.

(57) ABSTRACT

Disclosed herein are antisense compounds and methods for decreasing CD40. Examples of disease conditions that can be ameliorated with the administration of antisense compounds targeted to CD40 include hyperproliferative disorders, graft versus host disease (GVHD), graft rejection, asthma, airway hyperresponsiveness, chronic obstructive pulmonary disease (COPD), multiple sclerosis (MS), systemic lupus erythematosus (SLE), and certain forms of arthritis.

20 Claims, No Drawings

(56) References Cited

U.S. PATENT DOCUMENTS

| | | |
|---|---|---|
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,352,775 A | 10/1994 | Albertsen et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,378,825 A | 1/1995 | Cook et al. |
| 5,386,023 A | 1/1995 | Sanghvi et al. |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,407,794 A | 4/1995 | Kass |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,436,327 A | 7/1995 | Southern et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,463,564 A | 10/1995 | Agrafiotis et al. |
| 5,463,657 A | 10/1995 | Rice |
| 5,466,677 A | 11/1995 | Baxter et al. |
| 5,466,786 A | 11/1995 | Buhr et al. |
| 5,470,967 A | 11/1995 | Huie et al. |
| 5,472,672 A | 12/1995 | Brennan |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,507,796 A | 4/1996 | Hasson |
| 5,508,270 A | 4/1996 | Baxter et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,523,389 A | 6/1996 | Ecker et al. |
| 5,525,465 A | 6/1996 | Haralambidis et al. |
| 5,525,711 A | 6/1996 | Hawkins et al. |
| 5,529,756 A | 6/1996 | Brennan |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,543,508 A | 8/1996 | Haseloff et al. |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,554,613 A | 9/1996 | Mallion |
| 5,561,225 A | 10/1996 | Maddry et al. |
| 5,563,036 A | 10/1996 | Peterson et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,574,656 A | 11/1996 | Agrafiotis et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,612,455 A | 3/1997 | Hoey |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,603 A | 6/1997 | Dower et al. |
| 5,639,873 A | 6/1997 | Barascut et al. |
| 5,641,625 A | 6/1997 | Ecker et al. |
| 5,646,265 A | 7/1997 | McGee |
| 5,650,122 A | 7/1997 | Harris et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,684,711 A | 11/1997 | Agrafiotis et al. |
| 5,688,941 A | 11/1997 | Cook et al. |
| 5,693,463 A | 12/1997 | Edwards et al. |
| 5,696,248 A | 12/1997 | Peyman et al. |
| 5,697,248 A | 12/1997 | Brown |
| 5,700,637 A | 12/1997 | Southern |
| 5,700,920 A | 12/1997 | Altmann et al. |
| 5,700,922 A | 12/1997 | Cook |
| 5,708,158 A | 1/1998 | Hoey |
| 5,714,331 A | 2/1998 | Buchardt et al. |
| 5,716,780 A | 2/1998 | Edwards et al. |
| 5,719,262 A | 2/1998 | Buchardt et al. |
| 5,720,923 A | 2/1998 | Haff et al. |
| 5,766,855 A | 6/1998 | Buchardt et al. |
| 5,773,571 A | 6/1998 | Nielsen et al. |
| 5,783,431 A | 7/1998 | Peterson et al. |
| 5,786,461 A | 7/1998 | Buchardt et al. |
| 5,789,573 A | 8/1998 | Baker et al. |
| 5,801,154 A | 9/1998 | Baracchini et al. |
| 5,824,485 A | 10/1998 | Thompson et al. |
| 5,831,014 A | 11/1998 | Cook et al. |
| 5,859,221 A | 1/1999 | Cook et al. |
| 5,864,010 A | 1/1999 | Cook et al. |
| 5,877,021 A | 3/1999 | Stinchcomb et al. |
| 5,901,069 A | 5/1999 | Agrafiotis et al. |
| 5,955,589 A | 9/1999 | Cook et al. |
| 5,969,116 A | 10/1999 | Martin |

(56) References Cited

U.S. PATENT DOCUMENTS

| | | | |
|---|---|---|---|
| 5,986,053 | A | 11/1999 | Ecker et al. |
| 6,016,348 | A | 1/2000 | Blatter et al. |
| 6,025,339 | A | 2/2000 | Nyce et al. |
| 6,143,881 | A | 11/2000 | Metelev et al. |
| 6,194,150 | B1 | 2/2001 | Stinchcomb et al. |
| 6,197,584 | B1 | 3/2001 | Bennett et al. |
| 6,201,103 | B1 | 3/2001 | Nielsen et al. |
| 6,204,326 | B1 | 3/2001 | Cook et al. |
| 6,210,892 | B1 | 4/2001 | Bennett et al. |
| 6,228,982 | B1 | 5/2001 | Norden et al. |
| 6,295,514 | B1 | 9/2001 | Agrafiotis et al. |
| 6,346,614 | B1 | 2/2002 | Metelev et al. |
| 6,350,853 | B1 | 2/2002 | Nielsen et al. |
| 6,395,474 | B1 | 5/2002 | Buchardt et al. |
| 6,399,754 | B1 | 6/2002 | Cook |
| 6,414,112 | B1 | 7/2002 | Buchardt et al. |
| 6,421,612 | B1 | 7/2002 | Agrafiotis et al. |
| 6,434,490 | B1 | 8/2002 | Agrafiotis et al. |
| 6,441,130 | B1 | 8/2002 | Egholm et al. |
| 6,451,968 | B1 | 9/2002 | Egholm et al. |
| 6,453,246 | B1 | 9/2002 | Agrafiotis et al. |
| 6,506,784 | B1 | 1/2003 | Dhanoa et al. |
| 6,518,266 | B1 | 2/2003 | Dhanoa et al. |
| 6,571,227 | B1 | 5/2003 | Salemme et al. |
| 6,582,908 | B2 | 6/2003 | Fodor et al. |
| 6,593,292 | B1 | 7/2003 | Rothbard et al. |
| 6,617,162 | B2 * | 9/2003 | Dobie et al. ............... 435/375 |
| 2001/0053519 | A1 | 12/2001 | Fodor et al. |
| 2002/0049173 | A1 | 4/2002 | Bennett et al. |
| 2003/0228597 | A1 | 12/2003 | Cowsert et al. |
| 2005/0202531 | A1 | 9/2005 | Toporik et al. |
| 2006/0063730 | A1 * | 3/2006 | Monia et al. ............... 514/44 |

FOREIGN PATENT DOCUMENTS

| | | |
|---|---|---|
| WO | WO 89/10977 | 11/1989 |
| WO | WO 92/20702 | 11/1992 |
| WO | WO 93/04204 | 3/1993 |
| WO | WO 94/02498 | 2/1994 |
| WO | WO 94/02499 | 2/1994 |
| WO | WO 94/05333 | 3/1994 |
| WO | WO 94/17093 | 8/1994 |
| WO | WO 95/28640 | 10/1995 |
| WO | WO 96/11205 | 4/1996 |
| WO | WO 86/07363 | 12/1996 |
| WO | WO 96/39415 | 12/1996 |
| WO | WO 97/22256 | 6/1997 |
| WO | WO 98/03533 | 1/1998 |
| WO | WO 98/37242 | 8/1998 |
| WO | WO 99/53101 | 10/1999 |
| WO | WO 99/57320 | 11/1999 |
| WO | WO 99/60010 | 11/1999 |
| WO | WO 01/27261 | 4/2001 |
| WO | WO 03/022222 | 3/2003 |

OTHER PUBLICATIONS

Ausubel et al., "Short Protocols in Molecular Biology" 2nd Edition, Greene Publishing Associates and John Wiley & Sons, New York (1992) 4-1 to 4-29, 10-33 to 10-35, 10-57 to 10-63, 11-3 to 11-54.
Baker et al., "Cleavage of the 5' Cap Structure of mRNA by a Europium(III) Macrocyclic Complex with Pendant Alcohol Groups" J. Am. Chem. Soc. (1997) 119(38):8749-8755.
Beaucage et al., "Deoxynucleoside Phosphoramidites—A New Class of Key Intermediates for Deoxypolynucleotide Synthesis" Tetrahedron Lett. (1981) 22:1859-1862.
Boumpas et al., "A short course of BG9588 (anti-CD40 ligand antibody) improves serologic activity and decreases humaturia in patients with proliferative lupas glomerulonephritis" Arthritis Rheum (2003) 48:719-727.
Branch et al., "A good antisense molecule is hard to find," TIBS (1998) 23:45-50.
Brazma et al., "Gene expression data analysis" FEBS Lett. (2000) 480:17-24.
Buhlmann et al., "Therapeutic Potential for Blockade of the CD40 Ligand, gp39" J. Clin. Immunol. (1996) 16(2):83-89.
Carulli et al., "High Throughput Analysis of Differential Gene Expression" J. Cell Biochem. Suppl. (1998) 30/31:286-296.
Celis et al., "Gene expression profiling: monitoring transcription and translation products using DNA microarrays and proteomics" FEBS Lett. (2000) 480:2-16.
Chiang et al., "Antisense Oligonucleotides Inhibit Interceullular Adhesion Molecule 1 Expression by Two Distinct Mechanisms" J. Biol. Chem. (1991) 266:18162-18171.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Clement et al., "Protein tyrosine kinase activation and protein kinase C translocation are functional components of CD40 signal transduction in resting human B cells" Immunological Investigations (1994) 23(6-7):437-448.
Christensen et al., "Solid-Phase Synthesis of Peptide Nucleic Acids" J. Pept. Sci. (1995) 3(1):175-183.
Crooke et al., "Pharmacokinetic Properties of Several Novel Oligonucleotide Analogs in mice" J. Pharmacol. Exp. Therapeutics (1996) 277:923-937.
Crooke et al., "Basic Principles of Antisense Therapeutics" Antisense Research and Application (1998) Chapter 1:1-50.
Dahl et al., "A Highly Reactive, Odourless Substitute for Thiophenol/Triethylamine as a Deprotection Reagent in the Synthesis of Oligonucleotides and their Analogues" Acta Chem. Scand. (1990) 44:639-641.
DeCamp et al., "Site-directed drug design" Protein Engineering, Principles and Practice, Cleland, J.L., et al. (Ed.) 1996, Chapter 17, 467-472.
Demesmaeker et al., "Antisense Oligonucleotides" Acc. Chem. Res. (1995) 28(9):366-374.
Elbashir et al., "RNA interference is mediated by 21- and 22-nucleotide RNAs" Genes Dev. (2001) 15:188-200.
Elbashir et al., "Duplexes of 21-nucleotide RNAs mediate RNA interference in cultured mammalian cells" Nature (2001) 411:494-498.
Englisch et al., "Chemically Modified Oligonucleotides as Probes and Inhibitors" Angewandte Chemie, International Edition (1991) 30(6):613-629.
Eliopoulos et al., "The role of the CD40 pathway in the pathogenesis and treatment of cancer" Curren Opinion in Pharmacology (2004) 4:360-367.
Fire et al., "Potent and specific genetics interference by double-stranded RNA in Caenorhabditis elegans" Nature (1998) 391:806-811.
Forster et al., "External Guide Sequences for an RNA Enzyme" Science (1990) 249:783-786.
Freier et al., "The ups and downs of nucleic acid duplex stability: structure-stability studies on chemically-modified DNA:RNA duplexes" Nucl. Acids Res. (1997) 25:4429-4443.
Fuchs et al., "Identification of Differentially Expressed Genes by Mutually Subtracted RNA Fingerprinting" Anal. Biochem. (2000) 286:91-98.
Gewirtz et al., "Facilitating oligonucleotide delivery: Helping antisense deliver on its promise" PNAS USA (1996) 93:3161-3163.
Ghosh et al., "Evaluation of some properties of a phosphorodithioate oligodeoxyribonucleotide for antisense application" Nucl. Acid Res. (1993) 21(24):5761-5766.
Ghosh et al., "Phosphorothioate-phosphodiester oligonucleotide co-polymers: assessment for antisense application" Anti-Cancer Drug Design, XP-002110959, 1993, 8, 15-32.
Glasser, "ISIS Pharmaceuticals Demonstrates Efficacy in Crohn's Disease with its Antisense Drug" Genetic Engin. News (1997) 17:1.
Going et al., "Molecular Pathology and Future Developments" Eur. J. Cancer (1999) 35.
Griffin et al., "The Synthesis of Oligoribonucleotides—II: Methoxymethylidene Derivatives of Ribonucleosides and 5'-Ribonucleotides" Tetrahedron (1967) 23:2301-2313.

(56) References Cited

OTHER PUBLICATIONS

Gruss et al., "CD40/CD40 Ligand Interactions in Normal, Reactive and Malignant Lympho-Hematopoietic Tissues" Leuk. Lymphoma (1997) 24:393-422.

Guo et al., "par-1, a Gene Required for Establishing Polarity in C. elegans Embryos, Encodes a Putative Ser/Thr Kinase That is Asymmetrically Distributed" Cell (1995) 81:611-620.

Haseloff et al., "Simple RNA enzymes with new and highly specific endoribonuclease activities" Nature (1988) 334:585-591.

Hyndman et al., "Software to determine optimal oligonucleotide sequences based on hybridization simulation data" BioTechniques, XP002932984, Jun. 1996, 20, 1090-1097.

Hyrup et al., "Peptide Nucleic Acids (PNA): Synthesis, Properties and Potential Applications" Bioorg. Med. Chem. 1996, 4(1), 5-23.

Janeway, "How the Immune System Recognizes Invaders" Sci. Amer. (1993) 269, 73-79.

Jones et al., "A rapid method for recombination and site-specific mutagenesis by placing homologous ends on DNA using polymerase chain reaction" Biotechniques (1991) 10(1):62-66.

Jungblut et al., "Proteomics in human disease: Cancer, heart and infectious diseases" Electrophoresis (1999) 20:2100-2110.

Jurecic et al., "Long-distance DD-PCR and cDNA microarrays" Curr. Opin. Microbiol. (2000) 3:316-321.

Kabanov et al., "A new class of antivirals: antisense oligonucleotides combined with a hydrophobic substituent effectively inhibit influenza virus reproduction and synthesis of virus-specific proteins in MDCK cells" FEBS Letts. (1990) 259(2):327-330.

Kahn, "From Genome to Preteome: Looking at a Cell's Proteins" Science (1995) 270:369-370.

Karras et al., "Peptide Nucleic Acids are Potent Modulators of Endogenous Pre-mRNA Splicing of the Murine Interleukin-5 Receptor-a Chain" Biochemistry (2001) 40:7853-7859.

Kaiser et al., "Color test for detection of free terminal amino groups in the solid-phase synthesis of peptides" Anal. Biochem. (1970) 34(2):595-598.

Kluth et al., "Endothelial Expression of CD40 in Renal Cell Carcinoma" Cancer Res. (1997) 57:891-899.

Koppelhus et al., "Cell-dependent differential cellular uptake of PNA, peptides, and PNA-peptide conjugates" Antisense & Nucleic Acid Drug Develop. (2002) 12:51-63.

Kroschwitz (ed.), "Polynucleotides" Concise Encyclopedia of Polymer Science and Engineering, John Wiley & Sons (1990) 858-859.

Lacerra et al., "Restoration of hemoglobin a synthesis in erythroid cells from peripheral blood of thalassemic patients" PNAS (2000) 97(17):9591-9596.

Larson et al., "Rapid DNA Fingerprinting of Pathogens by Flow Cytometry" Cytometry (2000) 41:203-208.

Larsson et al., "High-throughput protein expression of cDNA products as a tool in functional genomics" J. Biotechnol. (2000) 80:143-157.

Letsinger et al., "Cholesteryl-conjugated oligonucleotides: Synthesis, properties and activity as inhibitors of replication of human immunodeficiency virus in cell culture" PNAS (1989) 86:6553-6556.

Lima et al., "Implication of RNA Structure on Antisense Oligonucleotide Hybridization Kinetics" Biochem (1992) 31:12055-12061.

Lomakin et al., "A theoretical analysis of specificity of nucleic acid interactions with oligonucleotides and peptide nucleic acids (PNAs)" J. Molecular Biology (1998) 276(1):1-24.

Lutgens et al., "Requirement for CD154 in the progression of atherosclerosis" Nat. Med. (1999) 5(11):1313-1316.

Mach et al., "Reduction of atherosclerosis in mice by inhibition of CD40 signalling" Nature (1998) 394(9):200-203.

Mach et al., "Functional CD40 ligand is expressed on human vascular endothelial cells, smooth muscle cells, and macrophages: Implications for CD40-CD40 ligand signaling in atherosclerosis" PNAS (1997) 94:1931-1936.

Madden et al., "Serial analysis of gene expression: from gene discovery to target identification" Drug Discov. Today (2000) 5(9):415-425.

Makgoba et al., "The CD2-LFA-3 and LFA-1-ICAM pathways: relevance to T-cell recognition" Immunol. Today (1989) 10(12):417-422.

Manoharan et al., "Cholic Acid-Oligonucleotide Conjugates for Antisense Applications" Bioorganic Med. Chem. Letts. (1994) 4(8):1053-1060.

Manoharan et al., "Chemical Modifications to Improve Uptake and Bioavailability of Antisense Oligonucleotides" Ann. N.Y. Acad. Sci (1992) 660:306-309.

Manoharan et al., "Introduction of a Lipophilic Thioether Tether in the Minor Groove of Nucleic Acids for Antisense Applications" Bioorg. Med. Chem. Letts. (1993) 3(12):2765-2770.

Manoharan et al., "Lipidic Nucleic Acids" Tetrahedron Letts. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Martin et al., "Ein neuer Zugang zu 2'-O-Alkylribonucleosiden and Eigenschaften deren Oligonucleotide" Hely. Chim. Acta (1995) 78:486-504 (English summary included).

Matteucci et al., "Synthesis of Deoxyoligonucleoties on a Polymer Support" J. Am. Chem. Soc. (1981) 103:3185-3191.

Mercatante et al., "Modification of alternative splicing pathways as a potential approach to chemotherapy" Pharmacol. & Ther. (2000) 85:237-243.

Milligan et al., "Current Concepts in Antisense Drug Design" Journal of Medicinal Chemistry (1993) 36(14):1923-1937.

Milner et al., "Selecting Effective Antisense Reagents on Combinatorial Oligonucleotide Arrays" Nature Biotechnology (1997) 15:537-541.

Mirabelli et al., "In vitro and in vivo pharmacologic activities of antisense oligonucleotides" Anti-Cancer Drug Des. (1991) 6:647-661.

Mishra et al., "Improved leishmanicidal effect of phosphorothioate antisense oligonucleotides by LDL-medicated delivery" Biochim. Biophys. Acta. (1995) 1264:229-237.

Mitsuhashi, "Strategy for designing specific antisense oligonucleotide sequences" J. Gastroenterology (1997) 32:282-287.

Miura et al., "Fluorometric determination of total mRNA with oligo(dT) immobized on microtiter plates" Clin. Chem. (1996) 42(11) 1758-1764.

Montgomery et al., "RNA as a target of double-stranded RNA-mediated genetic interference in Caenorhabditis elegans" PNAS USA (1998) 95:15502-15507.

New England Biolabs 1998/99 Catalog (cover page and pp. 121 and 284).

Nickerson et al., "Automated DNA diagnostics using an ELISA-based oligonucleotide ligation assay" PNAS (1990) 87:8923-8927.

Nielsen et al., "Sequence-Selective Recognition of DNA by Strand Displacement with a Thymine-Substituted Polyamide" Science (1991) 254:1497-1500.

Nowak, "Entering the Postgenome Era" Science (1995) 270:368-371.

Oberhauser et al., "Effective incorporation of 2'-O-methyl-oligonucleotides into liposomes and enhanced cell association through modification with thiocholesterol" Nucl. Acids Res. (1992) 20(3):533-538.

Opalinska et al., "Nucleic-Acid Therapeutics: Basic Principles and Recent Applications" Nature Reviews Drug Discovery (2002) 1:503-514.

Patzel et al., "Theoretical design of antisense RNA structures substantially improves annealing kinetics and efficacy in human cells" Nat. Biotechnol (1998) 16(1):64-68.

Prashar et al., "READS: A Method for Display of 3'-End Fragments of Restriction Enzyme-Digested cDNAs for Analysis of Differential Gene Expression" Methods Enzymol. (1999) 303:258-272.

Rao et al., "elk tissue-specific ets-related genes on chromosomes X and 14 near translocation breakpoints" Science (1989) 244:66-70.

Reddy et al., "Fast Cleavage and Deprotection of Oligonucleotides" Tetrahedron Lett. (1994) 35(25):4311-4314.

Reynolds et al., "Rational siRNA design for RNA interference" Nature Biotechnology (2004) 22(3):326-330.

(56) References Cited

OTHER PUBLICATIONS

Rojanasakul, "Antisense oligonucleotide therapeutics: drug delivery and targeting" Advanced Drug Delivery Reviews (1996) 18:115-131.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi et al., "Heterocyclic Base Modifications in Nucleic Acids and their Applications in Antisense Oligonucleotides" Antisense Research and Applications, CRC Press, Boca Raton, Chapter 15 (1993) 273-288.
Santalucia et al., "Improved Nearest-Neighbor Parameters for Predicting DNA Duplex Stability" Biochem. (1996) 35:3555-3562.
Sazani et al., "Systemically delivered antisense oligomers upregulate gene expression in mouse tissues" Nature Biotech (2002) 20:1228-1233.
Sazani et al., "Nuclear antisense effects of neutral, anionic and cationic oligonucleotide analogs" Nucleic Acids Research (2001) 29(19):3965-3974.
Scaringe, "Design and Development of New Protecting Groups for RNA Synthesis" Ph.D. Thesis, University of Colorado, 1996.
Scaringe et al., "Novel RNA Synthesis Method Using 5'-O-Silyl-2'-O-orthoester Protecting Groups" J. Am. Chem. Soc. (1998) 120:11820-22821.
Schmajuk et al., "Antisense oligonucleotides with different backbones" J. Biol. Chem. (1999) 274(31):21783-21789.
Sczakiel et al., "Computer-aided search for effective antisense RNA target sequences of the human immunodeficiency virus type 1" Antisense Res. & Dev. (1993) 3:45-52.
Serra et al., "Predicting Thermodynamic Properties of RNA" Meth. Enzymol. (1995) 259:242-261.
Sharrocks et al., "The ETS-domain transcription factor family" Int. J. Biochem. Cell Biol. (1997) 29(12):1371-1387.
Shea et al., "Synthesis, hybridization properties and antiviral activity of lipid-oligodeoxynucleotide conjugates" Nucl. Acids Res. (1990) 18(13):3777-3783.
Sierakowska et al., "Repair of thalassemic human B-globin mRNA in mammalian cells by antisense oligonucleotides" PNAS (1996) 93:128401-12844.
Siwkowski et al., "Identification and functional validation of PNAs that inhibit murine CD40 expression by redirection of splicing" Nucleic Acids Research (2004) 32(9):2698.
Smith et al., "Comparison of Biosequences" Adv. Appl. Math (1981) 2:482-489.
Stamenkovic et al., "A B-lymphocyte activation molecule related to the nerve growth factor receptor and induced by cytokines in carcinomas" The EMBO Journal (1989) 8(5):1403-1410.
Stirchak et al., "Uncharged stereoregular nucleic acid analogues: 2. Morpholino nucleoside oligomers with carbamate internucleoside linkages" Nucleic Acid Research (1989) 17(15):6129-6141.
Stull et al., "Predicting antisense oligonucleotide inhibitory efficacy: a computational approach using histograms and thermodynamic indices" Nucleic Acids Res. (1992) 20(13):3501-3508.
Sugimoto et al., "Thermodynamic Parameters to Predict Stability of RNA/DNA Hybrid Duplexes" Biochem. (1995) 34:11211-11216.
Sutcliffe et al., "TOGA: An automated parsing technology for analyzing expression of nearly all genes" PNAS USA (2000) 97:1976-1981.
Svinarchuk et al., "Inhibition of HIV proliferation in MT-4 cells by antisense oligonucleotide conjugated to lipophilic groups" Biochimie (1993) 75:49-54.
Szoka, "Many are probed, but few are chosen" Nature Biotech (1997) 15:509.
Tabara et al., "RNAi in c. elegans: Soaking in the Genome Sequence" Science (1998) 282:430-431.
Tijsterman et al., "RNA Helicase MUT-14-Dependent Gene Silencing Triggered in C. elegans by Short Antisense RNAs" Science (2002) 295:694-697.
Timmons et al., "Specfic interference by ingested dsRNA" Nature (1998) 395:854.
Timmons et al., "Ingestion of bacterially expressed dsRNAs can produce specific potent genetic interference in Caenorhabditis elegans" Gene (2001) 263:103-112.
To, "Identification of Differential Gene Expression by High Throughput Analysis" Comb. Chem. High Throughput Screen. (2000) 3:235-241.
Tone et al., "Regulation of CD40 function by its isoforms generated through alternative splicing" PNAS (2001) 98:1751-1756.
Tuschl et al., "Targeted mRNA degradation by double-stranded RNA in vitro" Genes. Dev. (1999) 13:3191-3197.
Uhlmann et al., "Antisense Oligonucleotides: A New Therapeutic Principle" Chem. Reviews (1990) 90(4):544-584.
Wang et al., "Construction of CD40 antisense RNA and its apoptotic effect on Balm cell" Zhongguo Mian Yi Xue Zazhi (1999) 15: 100. (Abstract).
Wincott et al., "Synthesis, deprotection, analysis and purification of RNA and ribozymes" Nucleic Acids Res. (1995) 23(14):2677-2684.
Xia et al., "Thermodynamic parameters for an expanded nearest-neighbor model for formation of RNA duplexes with Watson-crick base pairs" Biochem (1998) 37:14719-14735.
Zhang et al., "PowerBLAST: A New Network BLAST Application for Interactive or Automated Sequence Analysis and Annotation" Genome Res. (1997) 7:649-656.
International Search Report for Application No. PCT/US2008/012998 dated Jun. 8, 2009.
International Search Report for Application No. PCT/US99/08765 dated Oct. 22, 1999.
Partial European Search Report for Application No. 99918757 dated Jul. 13, 2002.
"Analyzing DNA" Genome Analysis—A Laboratory Manuel, Green Ed. (1997) vol. 1, 574-578.

* cited by examiner

MODULATION OF CD40 EXPRESSION

RELATED APPLICATIONS

This application is a 35 U.S.C §371 national phase application of international application serial no. PCT/US2008/012998, filed on Nov. 20, 2008, which is a non-provisional of and claims priority to U.S. patent application Ser. No. 60/989421, filed on Nov. 20, 2007, the disclosure of each of which is incorporated herein by reference in its entirety.

SEQUENCE LISTING

The present application is being filed along with a Sequence Listing in electronic format. The Sequence Listing is provided as a file entitled 33841-513SEQLIST.txt, created Nov. 19, 2008, which is 67 Kb in size. The information in the electronic format of the sequence listing is incorporated herein by reference in its entirety. This sequence listing is identical to the sequence listing filed on Nov. 20, 2007, with the exception of the addition of SEQ ID NO: 237.

FIELD OF THE INVENTION

The present invention provides methods and compositions for lowing levels of CD40 in an animal. Such methods and compositions are useful as anti-inflammatory compounds and anti-tumor compounds.

BACKGROUND OF THE INVENTION

The immune system serves a vital role in protecting the body against infectious agents. It is well established, however, that a number of disease states and/or disorders are a result of either abnormal or undesirable activation of immune responses. Common examples include graft versus host disease (GVHD) and graft rejection, and autoimmune linked diseases such as multiple sclerosis (MS), systemic lupus erythematosus (SLE), and certain forms of arthritis.

In general, an immune response is activated as a result of either tissue injury or infection. Both cases involve the recruitment and activation of a number of immune system effector cells (e.g., B- and T-lymphocytes, macrophages, eosinophils, neutrophils) in a process coordinated through a series of complex cell-cell interactions. A typical scenario by which an immune response is mounted against a foreign protein is as follows: foreign proteins captured by antigen presenting cells (APC's) such as macrophages or dendritic cells are processed and displayed on the cell surface of the APC. Circulating T-helper cells which express an immunoglobulin that recognizes (i.e. binds) the displayed antigen undergo activation by the APC. These activated T-helpers in turn activate appropriate B-cell clones to proliferate and differentiate into plasma cells that produce and secrete humoral antibodies targeted against the foreign antigen. The secreted humoral antibodies are free to circulate and bind to any cells expressing the foreign protein on their cell surface, in effect marking the cell for destruction by other immune effector cells. In each of the stages described above, direct cell-cell contact between the involved cell types is required in order for activation to occur. (Gruss et al., Leuk. Lymphoma 1989, 24:393). In recent years, a number of cell surface receptors that mediate these cell-cell contact dependent activation events have been identified. Among these cell surface receptors is CD40 and its physiological ligand, CD40 Ligand (CD40L) which is also known as CD154.

CD40 was first characterized as a receptor expressed on B-lymphocytes. It was later found that engagement of B-cell CD40 with CD40L expressed on activated T-cells is essential for T-cell dependent B-cell activation (i.e. proliferation, immunoglobulin secretion, and class switching). It was subsequently revealed that functional CD40 is expressed on a variety of cell types other than B-cells, including macrophages, dendritic cells, thymic epithelial cells, Langerhans cells, and endothelial cells. These studies have led to the current belief that CD40 plays a broad role in immune regulation by mediating interactions of T-cells with B-cells as well as other cell types. In support of this notion, it has been shown that stimulation of CD40 in macrophages and dendritic results is required for T-cell activation during antigen presentation. (Gruss et al., Leuk. Lymphoma, 1997, 24:393). Recent evidence points to a role for CD40 in tissue inflammation as well. Production of the inflammatory mediators IL-12 and nitric oxide by macrophages have been shown to be CD40 dependent. (Buhlmann and Noelle, J. Clin. Immunol., 1996, 16:83). In endothelial cells, stimulation of CD40 by CD40L has been found to induce surface expression of E-selectin, ICAM-1, and VCAM-1, promoting adhesion of leukocytes to sites of inflammation (Buhlmann and Noelle, J. Clin. Immunol., 1996, 16:83); Gruss et al., Leuk. Lymphoma, 1997, 24:393). Finally, a number of reports have documented overexpression of CD40 in epithelial and hematopoietic tumors as well as tumor infiltrating endothelial cells, indicating that CD40 may play a role in tumor growth and/or angiogenesis as well (Gruss et al., Leuk. Lymphoma, 1997, 24:393; Kluth et al., Cancer Res., 1997, 57:891).

Due to the pivotal role that CD40 plays in humoral immunity, the potential exists that therapeutic strategies aimed at downregulating CD40 or interfering with CD40 signaling may provide a novel class of agents useful in treating a number of immune associated disorders, including but not limited to graft-versus-host disease (GVHD), graft rejection, and autoimmune diseases such as multiple sclerosis (MS), systemic lupus erythematosus (SLE), and certain forms of arthritis. Inhibitors of CD40 may also prove useful as anti-inflammatory compounds, and could therefore be useful as treatment for a variety of inflammatory and allergic conditions such as asthma, rheumatoid arthritis, allograft rejections, inflammatory bowel disease, autoimmune encephalomyelitis, thyroiditis, various dermatological conditions, and psoriasis. Recently, both CD40 and CD154 have been shown to be expressed on vascular endothelial cells, vascular smooth muscle cells and macrophages present in atherosclerotic plaques, suggesting that inflammation and immunity contribute to the atherogenic process. That this process involves CD40 signaling is suggested by several studies in mouse models in which disruption of CD154 (by knockout or by monoclonal antibody) reduced the progression or size of atherosclerotic lesions. (Mach et al., Nature, 1998, 394:200-3; Lutgens et al., 1999, Nat. Med. 5:1313-6).

Finally, as more is learned of the association between CD40 overexpression and tumor growth, inhibitors of CD40 may prove useful as anti-tumor agents and inhibitors of other hyperproliferative conditions as well.

Currently, there are no known therapeutic agents which effectively inhibit the synthesis of CD40. To date, strategies aimed at inhibiting CD40 function have involved the use of a variety of agents that disrupt CD40/CD40L binding. These include monoclonal antibodies directed against either CD40 or CD40L, soluble forms of CD40, and synthetic peptides derived from a second CD40 binding protein, A20. The use of neutralizing antibodies against CD40 and/or CD40L in animal models has provided evidence that inhibition of CD40 signaling would have therapeutic benefit for GVHD, allograft rejection, rheumatoid arthritis, SLE, MS, and B-cell lymphoma. (Buhlmann and Noelle, *J. Clin. Immunol*, 1996, 16:83). Clinical investigations were initiated using anti-CD154 monoclonal antibody in patients with lupus nephritis. However, studies were terminated due to the development of thrombotic events. (Boumpas et al., 2003, *Arthritis Rheum*. 2003, 48:719-27).

Due to the problems associated with the use of large proteins as therapeutic agents, there is a long-felt need for additional agents capable of effectively inhibiting CD40 function. Antisense oligonucleotides avoid many of the pitfalls of current agents used to block CD40/CD40L interactions and may therefore prove to be uniquely useful in a number of therapeutic, diagnostic and research applications. U.S. Pat. No. 6,197,584 (Bennett and Cowsert) discloses antisense compounds targeted to CD40.

SUMMARY OF THE INVENTION

Provided herein are antisense compounds, compositions, and methods for the treatment and prevention of inflammatory conditions and cancer.

Antisense compounds described herein may be 12 to 30 nucleobases in length targeted to a CD40 nucleic acid. In certain embodiments, the CD40 nucleic acid may be any of the sequences as set forth in GENBANK® Accession No. X60592.1, incorporated herein as SEQ ID NO: 1; GENBANK® Accession No. H50598.1, incorporated herein as SEQ ID NO: 2; GENBANK® Accession No. AA203290.1, incorporated herein as SEQ ID NO: 3; and nucleotides 9797000 to nucleotide 9813000 of GENBANK Accession No. NT_011362.9, incorporated herein as SEQ ID NO: 4, or GENBANK® Accession No. BC064518.1, incorporated herein as SEQ ID NO: 237.

The antisense compound may be 12 to 30 nucleobases in length and may have a nucleobase sequence comprising at least 8 contiguous nucleobases complementary to an equal length portion of an intron region of the CD40 gene, selected from the following regions of SEQ ID NO: 4:

(a) positions 11250-12685, corresponding to intron 6;
(b) positions 2943-6367, corresponding to intron 1,
(c) positions 6447-6780, corresponding to intron 2,
(d) positions 6907-7157, corresponding to intron 3,
(e) positions 7305-7673, corresponding to intron 4,
(f) positions 7768-11187, corresponding to intron 5,
(g) positions 12773-12877, corresponding to intron 7, or
(h) positions 12907-13429, corresponding to intron 8, wherein the remaining part or parts of the antisense compound are at least 70% complementary to the sequence shown in SEQ ID NO: 4. Preferably, the remaining parts of the antisense compound are at least 75%, 80%, 85%, 90%, 95%, 98%, 99%, or, most preferably, 100% complementary to the sequence shown in SEQ ID NO: 4.

Preferably, the antisense compound may comprise at least 8 contiguous nucleobases complementary to an equal length portion of positions 12527 to 12685 of SEQ ID NO: 4, which is a region that can be either part of intron 6, or can be part of an alternative version of exon 7 when a different splice acceptor site is selected. Preferably, the antisense compound has a nucleobase sequence comprising at least 8 contiguous nucleobases of the nucleobase sequence of SEQ ID NO: 208, wherein the nucleobase sequence of the compound is at least 70% complementary to the sequence shown in SEQ ID NO: 4. Preferably, the antisense compound is at least 75%, 80%, 85%, 90%, 95%, 98%, 99%, or, most preferably, 100% complementary to the sequence shown in SEQ ID NO: 4.

More preferably, the antisense compound has the sequence of SEQ ID NO: 208. Even more preferably, the antisense compound is 20 nucleobases in length and consists of the nucleobase sequence of SEQ ID NO: 208. Most preferably, the antisense compound is an antisense oligonucleotide 20 nucleotides in length having the sequence of nucleotides as set forth in SEQ ID NO:208, wherein each cytosine is a 5-methylcytosine, each internucleoside linkage is a phosphorothioate linkage, nucleotides 1-5 and 16-20 are 2'-O-methoxyethyl nucleotides, and nucleotides 6-15 are 2'-deoxynucleotides; most preferably the antisense compound is ISIS 396236.

In an alternative embodiment, the antisense compound may be 12 to 30 nucleobases in length and have a nucleobase sequence comprising at least 8 contiguous nucleobases complementary to an equal length portion of a region of the CD40 gene, corresponding to positions 13662-16001 of SEQ ID NO: 4, which forms part of exon 9 or a region 3' to exon 9, wherein the remaining parts of the antisense compound are at least 70% complementary to the sequence shown in SEQ ID NO: 4. Preferably, the target region of the CD40 gene corresponds to positions 13877-14084, even more preferably to positions 13937-13996, of SEQ ID NO: 4. Preferably, the remaining parts of the antisense compound are at least 75%, 80%, 85%, 90%, 95%, 98%, 99%, or, most preferably, 100% complementary to the sequence shown in SEQ ID NO: 4.

In yet another alternative embodiment, the antisense compound is 12 to 30 nucleobases in length and has a nucleobase sequence complementary to the sequence shown in SEQ ID NO: 1, starting at position 69 or 70 of SEQ ID NO: 1, wherein the nucleobase sequence is at least 95% complementary to the sequence shown in SEQ ID NO: 1. Preferably, the nucleobase sequence is essentially complementary to the sequence shown in SEQ ID NO: 1. More preferably, the nucleobase sequence is selected from the sequences of SEQ ID Nos: 90 and 163. Even more preferably, the antisense compound has a nucleobase sequence of SEQ ID NO: 90. Even more preferably, the antisense compound is 18 or 20 nucleobases in length and consists of the nucleobase sequence of SEQ ID NO: 90 or SEQ ID NO: 163. The antisense compound may be ISIS26163, ISIS396201 or ISIS396278. Preferably, the antisense compound is an antisense oligonucleotide 18 nucleotides in length having the sequence of nucleotides as set forth in SEQ ID NO: 90, wherein each cytosine is a 5-methylcytosine, each internucleoside linkage is a phosphorothioate linkage, nucleotides 1-4 and 15-18 are 2'-O-methoxyethyl nucleotides, and nucleotides 5 to 14 are 2'-deoxynucleotides. Most preferably, the antisense compound is ISIS26163.

An antisense compound according to the invention may comprise a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 5 to 236. Preferably, the compound consists of a single-stranded modified oligonucleotide. Preferably, the nucleobase sequence of the modified oligonucleotide is 100% complementary to a nucleobase sequence of SEQ ID NO: 1, SEQ ID NO: 2, SEQ ID NO: 3, SEQ ID NO: 4, or SEQ ID NO: 237.

The antisense compound may comprise linked nucleosides. Preferably, the antisense compound is an antisense oligonucleotide.

The antisense compound may be a single-stranded or double-stranded oligonucleotide. Preferably, the antisense compound is a single-stranded oligonucleotide.

The antisense oligonucleotide may be modified, wherein at least one internucleoside linkage is a modified internucleoside linkage. The internucleoside linkage may be a phosphorothioate internucleoside linkage.

The antisense oligonucleotide may be modified, wherein at least one nucleoside comprises a modified sugar. The modified sugar may be a bicyclic sugar. Preferably, the at least one bicyclic sugar comprises a 4'-CH(CH3)—O-2' bridge. The modified sugar may comprise a 2'-O-methoxyethyl. The antisense compound may comprise at least one tetrahydropyran modified nucleoside, wherein a tetrahydropyran ring replaces the furanose ring. Preferably, each of the at least one tetrahydropyran modified nucleoside has the structure

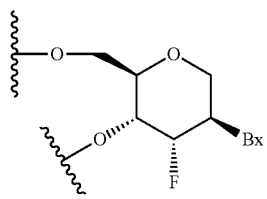

wherein Bx is an optionally protected heterocyclic base moiety.

The antisense compound may comprise a modified nucleobase. The modified nucleobase may be a 5-methylcytosine. Preferably, every cytosine is a 5-methylcytosine.

The antisense compound may be a gapmer, for example an oligonucleotide comprising:
  a gap segment consisting of linked deoxynucleosides;
  a 5' wing segment consisting of linked nucleosides;
  a 3' wing segment consisting of linked nucleosides;
  wherein the gap segment is positioned between the 5' wing segment and the 3' wing segment and wherein each nucleoside of each wing segment comprises a modified sugar. Preferably, each nucleoside of each wing segment comprises a 2'-O-methoxyethyl sugar; and preferably each internucleoside linkage is a phosphorothioate linkage.

The antisense oligonucleotide may be a 5-10-5 MOE gapmer or a 2-15-3 MOE gapmer. The antisense oligonucleotide may consist of 20 linked nucleosides.

The antisense oligonucleotide may be a 4-10-4 MOE gapmer. The antisense oligonucleotide may consist of 18 linked nucleosides.

Compositions described herein may comprise an oligonucleotide consisting of 12 to 30 linked nucleosides, targeted to a CD40 nucleic acid or a salt thereof and a pharmaceutically acceptable carrier or diluent.

The composition may comprise a single-stranded or double-stranded oligonucleotide.

Another embodiment of the invention is a pharmaceutical composition comprising an antisense compound as described above and a liposome or a lipid based delivery system. Preferably, said liposome is an amphoteric liposome. Preferably, said amphoteric liposome is formed from a lipid phase comprising an amphoteric lipid or a mixture of lipid components with amphoteric properties. Said amphoteric liposome may further comprise one or more neutral or zwitterionic lipids. More preferably, said amphoteric liposome is formed from a lipid phase comprising
  (a) about 15 mol % POPC, about 45 mol % DOPE, about 20 mol % MoChol, about 20 mol % Chems
  (b) about 60 mol % POPC, about 10 mol % DOTAP, about 30 mol % Chems
  (c) about 30 mol % POPC, about 10 mol % DOTAP, about 20 mol % Chems, about 40 mol % Chol
  (d) about 60 mol % POPC, about 20 mol % HistChol, about 20 mol % Chol.

A further embodiment of the invention is an antisense compound or composition as described above for medical use. Yet a further embodiment of the invention is an antisense compound or a composition as described above for the treatment of cancer or an inflammatory or immune associated condition. The treatment may further comprise administering a second drug, which may be administered separately or concomitantly with the antisense compound of the invention.

Methods described herein may comprise administering to an animal an antisense compound as described above, preferably an antisense compound comprising an oligonucleotide consisting of 12 to 30 linked nucleosides targeted to a CD40 nucleic acid, or a composition comprising said antisense compound. Preferably, the animal is a human.

Administration of the antisense compound and/or the second drug may be by parenteral administration, topical administration, oral administration or aerosol administration. Parenteral administration may be any of subcutaneous or intravenous administration.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Acceptable safety profile" means a pattern of side effects that is within clinically acceptable limits.

"Active pharmaceutical ingredient" means the substance or substances in a pharmaceutical composition that provides a desired effect.

"Active target region" means a target region to which one or more active antisense compounds is targeted. "Active antisense compounds" means antisense compounds that reduce target nucleic acid levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration.

"Administering" means providing a pharmaceutical agent to an individual, and includes, but is not limited to administering by a medical professional and self-administering.

"Antisense compound" means an oligomeric compound that is capable of undergoing hybridization to a target nucleic acid through hydrogen bonding.

"Antisense inhibition" means reduction of target nucleic acid levels in the presence of an antisense compound complementary to a target nucleic acid compared to target nucleic acid levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" or "bicyclic nucleoside" or "bicyclic nucleotide" refers to a nucleoside or nucleotide wherein the furanose portion of the nucleoside includes a bridge connecting two carbon atoms on the furanose ring, thereby forming a bicyclic ring system. As used herein, unless otherwise indicated, the term "methyleneoxy BNA" alone refers to β-D-methyleneoxy BNA.

"Cap structure" or "terminal cap moiety" means chemical modifications, which have been incorporated at either terminus of an antisense compound.

"Chimeric antisense compounds" means antisense compounds that have at least 2 chemically distinct regions, each position having a plurality of subunits. A "gapmer" means an antisense compound in which an internal position having a plurality of nucleotides that supports RNaseH cleavage is positioned between external regions having one or more nucleotides that are chemically distinct from the nucleosides of the internal region. A "gap segment" means the plurality of nucleotides that make up the internal region of a gapmer. A "wing segment" means the external region of a gapmer.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses administration in parallel or sequentially.

"Complementarity" means the capacity for pairing between nucleobases of a first nucleic acid and a second nucleic acid.

"Comply" means the adherence with a recommended therapy by a individual.

"Contiguous nucleobases" means nucleobases immediately adjacent to each other.

"Diluent" means an ingredient in a composition that lacks pharmacological activity, but is pharmaceutically necessary or desirable. For example, in drugs that are injected the diluent may be a liquid, e.g. saline solution.

"Dose" means a specified quantity of a pharmaceutical agent provided in a single administration, or in a specified time period. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in a individual. In other embodiments, the pharmaceutical agent is administered by infusion over an extended period of time or continuously. Doses may be stated as the amount of pharmaceutical agent per hour, day, week or month.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Duration" means the period of time during which an activity or event continues. In certain embodiments, the duration of treatment is the period of time during which doses of a pharmaceutical agent are administered.

"Efficacy" means the ability to produce a desired effect.

"CD40 nucleic acid" means any nucleic acid encoding CD40. For example, in certain embodiments, a CD40 nucleic acid includes, without limitation, a DNA sequence encoding CD40, an RNA sequence transcribed from DNA encoding CD40, and an mRNA sequence encoding CD40. "CD40 mRNA" means an mRNA encoding a CD40 protein.

"Fully complementary" means each nucleobase of a first nucleic acid has a complementary nucleobase in a second nucleic acid. In certain embodiments, a first nucleic acid is an antisense compound and a target nucleic acid is a second nucleic acid. In certain such embodiments, an antisense oligonucleotide is a first nucleic acid and a target nucleic acid is a second nucleic acid.

"Gap-widened" means an antisense compound has a gap segment of 12 or more contiguous 2'-deoxyribonucleotides positioned between and immediately adjacent to 5' and 3' wing segments having from one to six nucleotides having modified sugar moieties. "Immediately adjacent" means there are no intervening nucleotides between the immediately adjacent elements.

"Hybridization" means the annealing of complementary nucleic acid molecules. In certain embodiments, complementary nucleic acid molecules include, but are not limited to, an antisense compound and a nucleic acid target. In certain such embodiments, complementary nucleic acid molecules include, but are not limited to, an antisense oligonucleotide and a nucleic acid target "Individual" means a human or non-human animal selected for treatment or therapy.

"Individual compliance" means adherence to a recommended or prescribed therapy by a individual.

"Injection site reaction" means inflammation or abnormal redness of skin at a site of injection in a individual.

"Internucleoside linkage" refers to the chemical bond between nucleosides.

"Linked nucleosides" means adjacent nucleosides which are bonded together.

"Modified internucleoside linkage" refers to a substitution and/or any change from a naturally occurring internucleoside bond (i.e. a phosphodiester internucleoside bond).

"Modified oligonucleotide" means an oligonucleotide comprising a modified internucleoside linkage, a modified sugar, and/or a modified nucleobase.

"Modified sugar" refers to a substitution and/or any change from a natural sugar.

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleotide" means a nucleotide having, independently, a modified sugar moiety, modified internucleoside linkage, or modified nucleobase. A "modified nucleoside" means a nucleotide having, independently, a modified sugar moiety or modified nucleobase.

"Modified sugar moiety" means a sugar moiety having any substitution and/or change from a natural sugar moiety.

"Motif" means the pattern of unmodified and modified nucleosides in an antisense compound.

"Naturally occurring internucleoside linkage" means a 3' to 5' phosphodiester linkage.

"Natural sugar moiety" means a sugar moiety found in DNA (2'-H) or RNA (2'-OH).

"Non-complementary nucleobase" or "mismatch" means a nucleobase of a first nucleic acid that is not capable of pairing with the corresponding nucleobase of a second or target nucleic acid.

"Nucleoside" means a nucleobase linked to a sugar.

As used herein the term "nucleoside mimetic" is intended to include those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleobase" means a heterocyclic moiety capable of pairing with a base of another nucleic acid.

"Nucleobase sequence" means the order of contiguous nucleobases independent of any sugar, linkage, and/or nucleobase modification.

"Nucleotide" means a nucleoside having a phosphate group covalently linked to the sugar portion of the nucleoside.

The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" means a polymer or oligomer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer or oligomer of linked nucleosides each of which can be modified or unmodified, independent one from another.

"Parenteral administration," means administration through injection or infusion. Parenteral administration includes, but is not limited to, subcutaneous administration, intravenous administration, or intramuscular administration.

"Pharmaceutical agent" means a substance that provides a therapeutic benefit when administered to a individual. For example, in certain embodiments, an antisense oligonucleotide targeted to CD40 is pharmaceutical agent.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Pharmaceutical composition" means a mixture of substances suitable for administering to an individual. For example, a pharmaceutical composition may comprise one or more antisense oligonucleotides or a combination of antisense oligonucleotides and non-antisense active agents and a sterile aqueous solution or other pharmaceutically acceptable additive.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prodrug" means a therapeutic agent that is prepared in an inactive form that is converted to an active form (i.e., drug) within the body or cells thereof by the action of endogenous enzymes or other chemicals and/or conditions.

"Recommended therapy" means a therapeutic regimen recommended by a medical professional for the treatment, amelioration, or prevention of a disease.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Single-stranded modified oligonucleotide" means a modified oligonucleotide which is not hybridized to a complementary strand.

"Specifically hybridizable" means an antisense compound that hybridizes to a target nucleic acid to induce a desired effect, while exhibiting minimal or no effects on non-target nucleic acids.

The term "sugar surrogate" overlaps with the slightly broader term "nucleoside mimetic" but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Stringent hybridization conditions" means conditions under which a nucleic acid molecule, such as an antisense compound, will hybridize to a target nucleic acid sequence, but to a minimal number of other sequences. Stringent conditions are sequence-dependent and will vary in different circumstances. In the context of this invention, "stringent conditions" under which oligomeric compounds hybridize to a target sequence are determined by the nature and composition of the oligomeric compounds and the assays in which they are being investigated.

"Subcutaneous administration" means administration just below the skin. "Intravenous administration" means administration into a vein.

"Targeted" or "targeted to" means having a nucleobase sequence that will allow specific hybridization of an antisense compound to a target nucleic acid to induce a desired effect. In certain embodiments, a desired effect is reduction of a target nucleic acid. In certain such embodiments, a desired effect is reduction of a CD40 mRNA.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds. Target nucleic acids may include, but are not limited to, DNA, RNA (including, but not limited to pre-mRNA and mRNA or portions thereof) transcribed from DNA encoding a target, and also miRNA.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Unmodified nucleotide" means a nucleotide composed of naturally occurring nucleobases, sugar moieties and internucleoside linkages. In certain embodiments, an unmodified nucleotide is an RNA nucleotide (i.e., β-D-ribonucleosides) or a DNA nucleotide (i.e., β-D-deoxyribonucleoside).

Antisense Compounds

Antisense compounds include, but are not limited to, oligonucleotides, oligonucleosides, oligonucleotide analogs, oligonucleotide mimetics, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a CD40 nucleic acid is 12 to 30 subunits in length. In other words, antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleotides.

In certain embodiments, a shortened or truncated antisense compound targeted to a CD40 nucleic acid has a single subunit deleted from the 5' end (5' truncation), or alternatively from the 3' end (3' truncation). A shortened or truncated antisense compound targeted to a CD40 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two are more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Bhanot et al. (PCT/US2007/068401) provided short antisense compounds, including compounds comprising chemically-modified high-affinity monomers 8 to 16 monomers in length. These short antisense compounds were shown to be useful for reducing target nucleic acids and/or proteins in cells, tissues, and animals with increased potency and improved therapeutic index. Short antisense compounds were effective at lower doses than previously described antisense compounds, allowing for a reduction in toxicity and cost of treatment. In addition, the described short antisense compounds have greater potential for oral dosing.

Antisense Compound Motifs

In certain embodiments, antisense compounds targeted to a CD40 nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In a preferred embodiment, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-10-4, 2-15-3, 4-12-3, 4-12-4, 3-14-3, 2-16-2, 1-18-1, 3-10-3, 2-10-2, 1-10-1 or 2-8-2.

In some embodiments, the antisense compound as a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10 or 8-2.

In one embodiment, antisense compounds targeted to a CD40 nucleic acid possess a 5-10-5 gapmer motif.

In some embodiments, an antisense compound targeted to a CD40 nucleic acid has a gap-widened motif. In other embodiments, an antisense oligonucleotide targeted to a CD40 nucleic acid has a gap-widened motif.

In one embodiment, a gap-widened antisense oligonucleotide targeted to a CD40 nucleic acid has a gap segment of fourteen 2'-deoxyribonucleotides positioned between wing segments of three chemically modified nucleosides. In one embodiment, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode CD40 include, without limitation, the following: GENBANK Accession No. X60592.1, first deposited with GENBANK® on Apr. 21, 1993 and incorporated herein as SEQ ID NO: 1; GENBANK® Accession No. H50598.1, first deposited with GENBANK® on Sep. 19, 1995, and incorporated herein as SEQ ID NO: 2; GENBANK Accession No. AA203290.1, first deposited with GENBANK® on Jan. 25, 1997, and incorporated herein as SEQ ID NO: 3; and nucleotides 9797000 to 9813000 of GENBANK Accession No. NT_011362.9, first deposited with GENBANK® on Nov. 29, 2000, and incorporated herein as SEQ ID NO: 4, and GENBANK® Accession No. BC064518.1, incorporated herein as SEQ ID NO: 237.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In one embodiment, a target region is a structurally defined region of the nucleic acid. For example, a target region may encompass a 3' UTR, a 5' UTR, an exon, an intron, a coding region, a translation initiation region, translation termination region, or other defined nucleic acid region. The structurally defined regions for CD40 can be obtained by accession number from sequence databases such as NCBI and such information is incorporated herein by reference. In other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In other embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In one embodiment, target segments within a target region are separated by no more than about 300 nucleotides. In other embodiments, target segments within a target region are separated by no more than about, 250, 200, 150, 100, 90, 80, 70, 60, 50, 40, 30, 20, or 10 nucleotides on the target nucleic acid. In another embodiment, target segments within a target region are separated by no more than about 5 nucleotides on the target nucleic acid. In additional embodiments, target segments are contiguous.

Suitable target segments may be found within a 5' UTR, a coding region, a 3' UTR, an intron, or an exon. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In one embodiment, reductions in CD40 mRNA levels are indicative of inhibition of CD40 expression. Reductions in levels of a CD40 protein are also indicative of inhibition of target mRNA expression. Further, phenotypic changes are indicative of inhibition of CD40 expression. For example, changes in cell morphology over time or treatment dose as well as changes in levels of cellular components such as proteins, lipids, nucleic acids, hormones, saccharides, or metals is indicative of inhibition of CD40 expression. Reduction of eosinophils is indicative of inhibition of CD40 expression. Measurements of cellular status which include pH, stage of cell cycle, intake or excretion of biological indicators by the cell are also endpoints of interest.

Analysis of the genotype of the cell (measurement of the expression of one or more of the genes of the cell) after treatment is also used as an indicator of the efficacy or potency of the CD40 inhibitors. Hallmark genes, or those genes suspected to be associated with a specific disease state, condition, or phenotype, are measured in both treated and untreated cells.

Genomic Structure, Exons and Introns

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Hybridization

In some embodiments, hybridization occurs between an antisense compound disclosed herein and a CD40 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In one embodiment, the antisense compounds provided herein are specifically hybridizable with a CD40 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a CD40 nucleic acid).

Non-complementary nucleobases between an antisense compound and a CD40 nucleic acid may be tolerated provided that the antisense compound remains able to specifically hybridize to a target nucleic acid. Moreover, an antisense compound may hybridize over one or more segments of a CD40 nucleic acid such that intervening or adjacent segments are not involved in the hybridization event (e.g., a loop structure, mismatch or hairpin structure).

In some embodiments, the antisense compounds provided herein are at least 70%, at least 75%, at least 80%, at least 85%, at least 90%, at least 95%, at least 96%, at least 97%, at least 98% or at least 99% complementary to a CD40 nucleic acid. Percent complementarity of an antisense compound with a target nucleic acid can be determined using routine methods. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In other embodiments, the antisense compounds provided herein are fully complementary (i.e, 100% complementary) to a target nucleic acid. For example, an antisense compound may be fully complementary to a CD40 nucleic acid, or a target region, or a target segment or target sequence thereof. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound.

When two or more non-complementary nucleobases are present, they may be contiguous (i.e. linked) or non-contiguous. In one embodiment, a non-complementary nucleobase is located in the wing segment of a gapmer antisense oligonucleotide.

In one embodiment, antisense compounds up to 20 nucleobases in length comprise no more than 4, no more than 3, no more than 2 or no more than 1 non-complementary nucleobase(s) relative to a target nucleic acid, such as a CD40 nucleic acid.

In another embodiment, antisense compounds up to 30 nucleobases in length comprise no more than 6, no more than 5, no more than 4, no more than 3, no more than 2 or no more than 1 non-complementary nucleobase(s) relative to a target nucleic acid, such as a CD40 nucleic acid.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In one embodiment, the antisense compounds are complementary to at least an 8 nucleobase portion of a target segment. In another embodiment, the antisense compounds are complementary to at least a 12 nucleobase portion of a target segment. In yet another embodiment, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In one embodiment, the antisense compounds are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphonoacetates, phosphoramidate, and phosphorothioates or phosphorodithioates. Internucleoside linkages that do not have a phosphorus atom include, amongst others, methylene(methylimino) or MMI linkages, morpholino linkages or amide linkages. In peptide nucleic acids (PNA) the sugar backbone is replaced with an amide containing backbone.

Methods of preparation of phosphorous-containing and non-phosphorous-containing linkages are well known.

Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697; 5,625,050 and U.S. Pat. No. 6,693,187, each of which is herein incorporated by reference.

Representative United States patents that teach the preparation of non-phosphorous-containing linkages include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In one embodiment, antisense compounds targeted to a CD40 nucleic acid comprise one or more modified internucleoside linkages. In some embodiments, the modified internucleoside linkages are phosphorothioate linkages. In other embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides are modified by modification of the ribofuranose ring. Such modifications include without limitation, addition of substituent groups, bridging of non-geminal ring atoms to form a bicyclic nucleic acid (BNA), as in locked nucleic acids (LNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$ (known as 2'-OMe) and 2'-O(CH$_2$)$_2$OCH$_3$ (known as 2'MOE) substituent groups. The substituent at the 2' position can also be selected from allyl, amino, azido, thio, O-allyl, O—C1-C10 alkyl, OCF$_3$, O—CH$_2$CH$_2$CH$_2$NH$_2$, O(CH$_2$)$_2$SCH$_3$, O(CH$_2$)$_2$—O—N(Rm)(Rn) such as 2'-dimethylaminooxyethoxy (2'-O—(CH$_2$)$_2$ON(CH$_3$)$_2$ or 2'-DMAOE), O(CH$_2$)$_2$—O—(CH$_2$)$_2$—N(Rm)(Rn) such as 2'-dimethylaminoethoxyethoxy (2'-O—(CH$_2$)$_2$—O—(CH$_2$)$_2$—N(CH$_3$)$_2$ or 2'-DMAEOE and O—CH$_2$—C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms, e.g. a 4'-(CH$_2$)$_n$—O-2' bridge, where n=1 or n=2. In certain embodiments, antisense compounds provided herein include one or more BNA nucleosides wherein the bridge comprises one of the formulas: 4'-(CH$_2$)—O-2' (LNA); 4'-(CH$_2$)—S-2'; 4'-(CH$_2$)—O-2' (LNA); 4'-(CH$_2$)$_2$—O-2' (ENA); 4'-C(CH$_3$)$_2$—O-2' (see PCT/US2008/068922); 4'-CH(CH$_3$)—O-2' and 4'CH(CH$_2$OCH$_3$)—O-2' (see U.S. Pat. No. 7,399,845, issued on Jul. 15, 2008); 4'-CH$_2$—N(OCH$_3$)-2' (see PCT/US2008/064591); 4'-CH$_2$—O—N(CH$_3$)-2' (see published U.S. Patent Application US2004-0171570, published Sep. 2, 2004); 4'-CH$_2$—N(R)—O-2' (see U.S. Pat. No. 7,427,672, issued on Sep. 23, 2008); 4'-CH$_2$—C(CH$_3$)-2' and 4'-CH$_2$—C(=CH$_2$)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (See PCT international application PCT/DK98/00393, published on Mar. 25, 1999 as WO99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

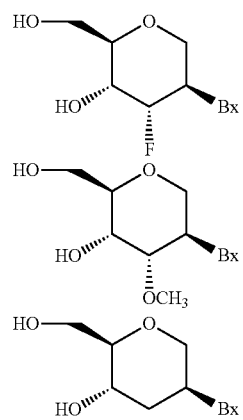

wherein Bx is an optionally protected heterocyclic base moiety.

Many other bicyclo and tricyclo sugar surrogate ring systems are also know in the art that can be used to modify nucleosides for incorporation into antisense compounds (see for example Leumann, C. J., Bioorg. Med. Chem. 10, (2002), 841-854). Such ring systems can undergo various additional substitutions to enhance activity.

Methods for the preparations of modified sugars are well known to those skilled in the art. Representative United States patents that teach the preparation of modified sugars include, but are not limited to U.S. Pat. No. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)$_2$—, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

In some embodiments, the bicyclic sugar moiety is bridged between the 2' and 4' carbon atoms with a biradical group selected from —O—(CH$_2$)p-, —O—CH$_2$—, —O—CH$_2$CH2, —O—CH(alkyl)-, —NH—(CH$_2$)p-, —N(alkyl)-(CH$_2$)p-, —O—CH(alkyl)-, —(CH(alkyl))-(CH$_2$)p-, —NH—O—(CH$_2$)p-, —N(alkyl)-O—(CH$_2$)p-, or —O—N(alkyl)-(CH$_2$)p-, wherein p is 1, 2, 3, 4 or 5 and each alkyl group can be further substituted. In certain embodiments, p is 1, 2 or 3.

In one aspect, each of said bridges is, independently, —[C(R1)(R2)]n-, —[C(R1)(R2)]n-O—, —C(R1R2)-N(R1)-O— or —C(R1R2)-O—N(R1)-. In another aspect, each of said bridges is, independently, 4'-(CH$_2$)$_3$-2',4'-(CH$_2$)$_2$-2',4'-CH$_2$—O-2',4'-(CH$_2$)$_2$—O-2',4'-CH$_2$—O—N(R1)-2' and 4'-CH$_2$—N(R1)-O-2'- wherein each R1 is, independently, H, a protecting group or C1-C12 alkyl.

In nucleotides having modified sugar moieties, the nucleobase moieties (natural, modified or a combination thereof) are maintained for hybridization with an appropriate nucleic acid target.

In one embodiment, antisense compounds targeted to a CD40 nucleic acid comprise one or more nucleotides having modified sugar moieties. In a preferred embodiment, the modified sugar moiety is 2'-MOE. In other embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

Methods for the preparations of modified nucleobases are well known to those skilled in the art. Representative United States patents that teach the preparation of modified nucleobases include, but are not limited to U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941 each of which is herein incorporated by reference.

In one embodiment, antisense compounds targeted to a CD40 nucleic acid comprise one or more modified nucleobases. In an additional embodiment, gap-widened antisense oligonucleotides targeted to a CD40 nucleic acid comprise one or more modified nucleobases. In some embodiments, the modified nucleobase is 5-methylcytosine. In further embodiments, each cytosine is a 5-methylcytosine.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Compositions and Methods for Formulating Pharmaceutical Compositions

Antisense oligonucleotides may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a CD40 nucleic acid can be utilized in pharmaceutical compositions by combining the antisense compound with a suitable pharmaceutically acceptable diluent or carrier. A pharmaceutically acceptable diluent includes for example phosphate-buffered saline (PBS). PBS is a diluent suitable for use in compositions to be delivered parenterally. Accordingly, in one embodiment, employed in the methods described herein is a pharmaceutical composition comprising an antisense compound targeted to a CD40 nucleic acid and a pharmaceutically acceptable diluent. In one embodiment, the pharmaceutically acceptable diluent is PBS. In other embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

Other liposomes or lipid based delivery systems known in the art are described for example in WO 05/105152; WO 06/069782; Morrissey et al., Nature Biotechnology, 23 (8), 1002-1007, 2005; WO 05/007196; Wheeler et al., Gene Therapy, 6 (2), 271-281, 1999; WO 02/34236; Budker et al., Nature Biotechnology, 14 (6), 760-764, 1996; U.S. Pat. No. 5,965,434; U.S. Pat. No. 5,635,487; Spagnou et al., Biochemistry, 43 (42), 13348-13356, 2004; U.S. Pat. No. 6,756,054; WO 06/016097 and U.S. Pat. No. 5,785,992; WO 04/035523, each of which is herein incorporated by reference.

In a preferred embodiment of the invention amphoteric liposomes may be used as formulations which include the inventive antisense compounds. Amphoteric liposomes are a class of liposomes having an anionic or neutral charge at pH 7.5 and a cationic charge at pH 4. Reference is made to WO 02/066012 by Panzner et al. which is incorporated herein by reference. The use, selection and manufacturing of amphoteric liposomes for the transfection of cells is further described in WO 05/094783 of Ended et al., WO 07/031,333 of Panzner et al., WO 07/107,304 of Panzner et al. and WO 08/043,575 of Panzner et al. Amphoteric liposomes have an excellent biodistribution and are well tolerated in animals. They can encapsulate nucleic acid molecules with high efficiency. WO 06/048329 of Panzner et al., which is incorporated herein by reference in its entirety, describes pharmaceutical compositions comprising amphoteric liposomes and oligonucleotides which are adapted to target nucleic acids encoding CD40.

By "amphoteric" is meant herein that the liposomes comprise charged groups of both anionic and cationic character wherein:

(i) at least one of the charged groups has a pKa between 4 and 7.4, (ii) the cationic charge prevails at pH 4 and (iii) the anionic charge prevails at pH 7.4;

whereby the liposomes have an isoelectric point of zero net charge between pH 4 and pH 7.4. Amphoteric character, by this definition, is different from "zwitterionic character", because zwitterions do not have a pK in the range mentioned above. In consequence, zwitterions are essentially neutral over a range of pH values. Phosphatidylcholine or phosphatidylethanolamines, for example, are neutral lipids with zwitterionic character.

Amphoteric liposomes may be formed from a lipid phase comprising an amphoteric lipid. In some embodiments said lipid phase may comprise 5 to 30 mol. % of said amphoteric lipid, preferably 10 to 25 mol. %.

Suitable amphoteric lipids are disclosed in WO 02/066489 and WO 03/070735 by Panzner et al. Preferably, said amphoteric lipid is selected from the group consisting of HistChol, HistDG, isoHistSuccDG, Acylcarnosin and HCChol. (A glossary of such abbreviated forms of the names of the lipids referred to herein is included below for ease of reference. A number of such abbreviations are those that are commonly used by those skilled in the art.)

Alternatively, said amphoteric liposomes may be formed from a lipid phase comprising a mixture of lipid components with amphoteric properties. Such amphoteric liposomes may be formed from pH-responsive anionic and/or cationic components, as disclosed for example in WO 02/066012. Cationic lipids sensitive to pH are disclosed in WO 02/066489 and WO 03/070220 and in the references made therein, in particular in Budker, et al. 1996, Nat Biotechnol. 14 (6):760-4, and can be used in combination with constitutively charged anionic lipids or with anionic lipids that are sensitive to pH.

Alternatively, the cationic charge may be introduced from constitutively charged lipids that are known to those skilled in the art in combination with a pH sensitive anionic lipid. Combinations of constitutively charged anionic and cationic lipids, e.g. DOTAP and DPPG, are not preferred. Thus, in some presently preferred embodiments of the invention, said mixture of lipid components may comprise (i) a stable cationic lipid and a chargeable anionic lipid, (ii) a chargeable cationic lipid and chargeable anionic lipid or (iii) a stable anionic lipid and a chargeable cationic lipid.

Preferred cationic components include DMTAP, DPTAP, DOTAP, DC-Chol, MoChol, HisChol, DPIM, CHIM, DOME, DDAB, DAC-Chol, TC-Chol, DOTMA, DOGS, $(C18)_2Gly^+$ N,N-dioctadecylamido-glycin, CTAB, CPyC, DODAP and DOEPC.

Preferred anionic lipids for use with the invention include DOGSucc, POGSucc, DMGSucc, DPGSucc, DMPS, DPPS, DOPS, POPS, DMPG, DPPG, DOPG, POPG, DMPA, DPPA, DOPA, POPA, CHEMS and CetylP.

Preferably, such an amphoteric mixture of lipids does not constitute more than about 70 mol. % of the lipid phase. In some embodiments, said mixture may constitute not more than 50 mol. % of the lipid phase; preferably said lipid phase comprises about 20 to about 40 mol. % of such a mixture.

In some embodiments, said lipid phase may further comprise a neutral lipid, preferably a neutral phospholipid, such as a phosphatidylcholine. Presently preferred phosphatidylcholines include POPC, natural or hydrogenated soy bean PC, natural or hydrogenated egg PC, DMPC, DPPC, DSPC and DOPC. More preferably, said phosphatidylcholine comprises POPC, non-hydrogenated soy bean PC or non-hydrogenated egg PC.

The lipid phase may comprise at least 15 mol. % of said phosphatidylcholine, preferably at least 20 mol. %. In some embodiments, said lipid phase may comprise no less than about 25 mol. % phosphatidylcholine. Alternatively, said lipid phase may comprise no less than about 40 mol. % phosphatidylcholine.

A presently preferred formulation in accordance with the present invention comprises a liposome having about 60 mol. % POPC, about 10 mol. % DOTAP and about 30 mol. % CHEMS.

In some embodiments said neutral lipid may comprise a phosphatidylethanolamine or a mixture of phosphatidylcholine and phosphatidylethanolamine. Said neutral phosphatidylcholines or phosphatidylethanolamines or mixtures of the two may be present in the lipid phase in the molar amount (mol. %) not constituted by the other components of the lipid phase, but to at least 20 mol. % (the total for the lipid phase being 100 mol. %).

Preferred phosphatidylethanolamines include DOPE, DMPE and DPPE.

In some embodiments said neutral lipid may comprise POPC and DOPE.

Advantageously, said lipid phase may comprise a mixture of anionic and cationic lipids with amphoteric properties, phosphatidylcholine and phosphatidylethanolamine. Amphoteric liposomes formed from such a lipid phase may be serum-stable and therefore suitable for systemic delivery. Preferably said lipid phase comprises MoChol as a cationic lipid and CHEMS or DMG-Succ as an anionic lipid.

Further presently preferred amphoteric liposomes for use as formulations which include antisense compounds of the present invention may be selected from the group consisting of:
  (a) about 15 mol. % POPC, about 45 mol. % DOPE, about 20 mol. % MoChol and about 20 mol. % CHEMS;
  (b) about 10 mol. % POPC, about 30 mol. % DOPE, about 30 mol. % MoChol and about 30 mol. % CHEMS;
  (c) about 10 mol. % POPC, about 30 mol. % DOPE, about 20 mol. % MoChol and about 40 mol. % CHEMS;
  (d) about 6 mol. % POPC, about 24 mol. % DOPE, about 47 mol. % MoChol and about 23 mol. % CHEMS.

Alternatively, said lipid phase may comprise a mixture of anionic and cationic lipids with amphoteric properties a neutral phosphatidylcholine and cholesterol. Such liposomes may also be serum-stable. In some embodiments, said lipid phase may comprise from 30 mol. % to 50 mol. % cholesterol, preferably from about 35 mol. % to about 45 mol. %. Alternatively, said lipid phase may comprise phosphatidylcholine and from 10 mol. % to 25 mol. % cholesterol, preferably from about 15 mol. % to about 25 mol. %.

A presently preferred formulation comprises 10 to 25 mol. % amphoteric lipid, e.g. HistChol, HistDG or Acylcarnosin, 15 to 25 mol. % cholesterol and the remainder being POPC, soy bean PC, egg PC, DMPC, DPPC or DOPC, preferably POPC; for example about 60 mol. % POPC, about 20 mol. % HistChol and about 20 mol. % Chol.

Another presently preferred formulation in accordance with the present invention comprises a liposome including a mix of lipid components with amphoteric properties and having about 30 mol. % POPC, about 10 mol. % DOTAP, about 20 mol. % CHEMS and about 40 mol. % Chol.

The amphoteric liposomes may have a size in the range 50 to 500 nm, preferably 100 to 500 nm, more preferably 150 and 300 nm.

The amphoteric liposome formulations of the present invention may be formulated for use as a colloid in a suitable pharmacologically acceptable vehicle. Vehicles such as water, saline, phosphate buffered saline and the like are well known to those skilled in the art for this purpose.

In some embodiments, the amphoteric liposome formulations of the present invention may be administered at a physiological pH of between about 7 and about 8. To this end, the formulation comprising the antisense compound, excipient and vehicle may be formulated to have a pH in this range.

The amphoteric liposome formulations of the invention may be manufactured using suitable methods that are known to those skilled in the art. Such methods include, but are not limited to, extrusion through membranes of defined pore size, injection of lipid solutions in ethanol into a water phase containing the cargo to be encapsulated, or high pressure homogenisation.

A solution of the oligonucleotide may be contacted with said excipient at a neutral pH, thereby resulting in volume inclusion of a certain percentage of the solution. An high concentrations of the excipient, ranging from about 50 mM to about 150 mM, is preferred to achieve substantial encapsulation of the active agent.

Amphoteric liposomes used as formulations in accordance with the present invention offer the distinct advantage of binding oligonucleotides at or below their isoelectric point, thereby concentrating said active agent at the liposome surface. This process is described in more detail in WO 02/066012.

Irrespective of the actual production process used to make the amphoteric liposome formulations, in some embodiments, non-encapsulated oligonucleotide may be removed from the liposomes after the initial production step in which the liposomes are formed as tight containers. Again, the technical literature and the references included herein describe such methodology in detail and suitable process steps may include, but are not limited to, size exclusion chromatography, sedimentation, dialysis, ultrafiltration and diafiltration.

However, the removal of any non-encapsulated oligonucleotide is not required for performance of the invention, and in some embodiments the composition may comprise free as well as entrapped drug.

In some aspects of the invention the amphoteric liposome formulations which include the inventive antisense compounds may be used as pharmaceutical compositions for the prevention or treatment of an inflammatory, immune or autoimmune disorder of a human or non-human animal such as graft rejection, graft-versus-host disease, multiple sclerosis, systemic lupus erythematosous, rheumatoid arthritis, asthma, inflammatory bowel disease, psoriasis or thyroiditis, Morbus Crohn and Colitis ulcerosa.

Glossary Of Common Abbreviated Lipid Names

DMPC Dimyristoylphosphatidylcholine
DPPC Dipalmitoylphosphatidylcholine
DSPC Distearoylphosphatidylcholine
POPC Palmitoyl-oleoylphosphatidylcholine
DOPC Dioleoylphosphatidylcholine
DOPE Dioleoylphosphatidylethanolamine
DMPE Dimyristoylphosphatidylethanolamine
DPPE Dipalmitoylphosphatidylethanolamine
DOPG Dioleoylphosphatidylglycerol
POPG Palmitoyl-oleoylphosphatidylglycerol
DMPG Dimyristoylphosphatidylglycerol
DPPG Dipalmitoylphosphatidylglycerol
DMPS Dimyristoylphosphatidylserine
DPPS Dipalmitoylphosphatidylserine
DOPS Dioleoylphosphatidylserine
POPS Palmitoyl-oleoylphosphatidylserine
DMPA Dimyristoylphosphatidic acid
DPPA Dipalmitoylphosphatidic acid
DOPA Dioleoylphosphatidic acid
POPA Palmitoyl-oleoylphosphatidic acid
CHEMS Cholesterolhemisuccinate
DC-Chol 3-β-[N—(N',N'-dimethylethane) carbamoyl]cholesterol
CetylP Cetylphosphate
DODAP (1,2)-dioleoyloxypropyl)-N,N-dimethylammonium chloride
DOEPC 1,2-dioleoyl-sn-glycero-3-ethylphosphocholine
DAC-Chol 3-β-[N—(N,N'-dimethylethane) carbamoyl]cholesterol
TC-Chol 3-β-[N—(N',N',N'-trimethylaminoethane)carbamoyl]cholesterol
DOTMA (1,2-dioleyloxypropyl)-N,N,N-trimethylammoniumchlorid) (Lipofectin®)
DOGS ((C18)$_2$GlySper3$^+$) N,N-dioctadecylamido-glycyl-spermine (Transfectam®)
CTAB Cetyl-trimethylammoniumbromide,
CPyC Cetyl-pyridiniumchloride
DOTAP (1,2-dioleoyloxypropyl)-N,N,N-trimethylammonium salt
DMTAP (1,2-dimyristoyloxypropyl)-N,N,N-trimethylammonium salt
DPTAP (1,2-dipalmitoyloxypropyl)-N,N,N-trimethylammonium salt
DOTMA (1,2-dioleyloxypropyl)-N,N,N-trimethylammonium chloride)
DORIE (1,2-dioleyloxypropyl)-3 dimethylhydroxyethyl ammoniumbromide)
DDAB Dimethyldioctadecylammonium bromide
DPIM 4-(2,3-bis-palmitoyloxy-propyl)-1-methyl-1H-imidazole
CHIM Histaminyl-Cholesterolcarbamate
MoChol 4-(2-Aminoethyl)-Morpholino-Cholesterol-hemisuccinate
His Chol Histaminyl-Cholesterolhemisuccinate.
HCChol Nα-Histidinyl-Cholesterolcarbamate
HistChol Nα-Histidinyl-Cholesterol-hemisuccinate.
AC Acylcarnosine, Stearyl- & Palmitoylcarnosine
HistDG 1,2-Dipalmitoylglycerol-hemisuccinate-Nα-Histidinyl-hemisuccinate, & Distearoyl-, Dimyristoyl-, Dioleoyl- or palmitoyl-oleoylderivatives
IsoHistSuccDG 1,2-Dipalmitoylglycerol-Oα-Histidinyl-Nα-hemisuccinat, & Distearoyl-, Dimyristoyl-, Dioleoyl- or palmitoyl-oleoylderivatives
DGSucc 1,2-Dipalmitoyglycerol-3-hemisuccinate & Distearoyl-, Dimyristoyl-Dioleoyl- or palmitoyl-oleoyl-derivatives The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety. In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG); cationic (e.g. dioleoyltetramethylaminopropyl DOTAP and dioleoylphosphatidyl ethanolamine DOTMA) or amphoteric lipids or lipid mixtures wherein a mixture of cationic and anionic lipids displays amphoteric properties. For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other active agents which function by a non-antisense mechanism, such as for example chemotherapeutic agents or antiinflammatory drugs. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

Cell Culture and Antisense Compounds Treatment

The effects of antisense compounds on the level, activity or expression of CD40 nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, HuVEC cells, T24, A549, and primary hepatocytes.

In vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a CD40 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as GAPDH or by quantifying total RNA using RIBOGREEN® (Invitrogen, Inc. Carlsbad, Calif.). GAPDH expression is quantified by real time PCR, by being run simultaneously with the target, multiplexing, or separately. Total RNA is quantified using RIBOGREEN® RNA quantification reagent (Invetrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a CD40 nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of CD40 nucleic acids can be assessed by measuring CD40 protein levels. Protein levels of CD40 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat CD40 are commercially available.

In vivo Testing of Antisense Compounds

Antisense compounds, for example, antisense oligonucleotides, are tested in animals to assess their ability to inhibit expression of CD40 and produce phenotypic changes, such as changes in cell morphology over time or treatment dose as well as changes in levels of cellular components such as proteins, nucleic acids, hormones, cytokines, and eosinophils. Testing may be performed in normal animals, or in experimental disease models. For administration to animals, antisense oligonucleotides are formulated in a pharmaceutically acceptable diluent, such as phosphate-buffered saline. Administration includes pulmonary administration, aerosol administration, topical administration, and parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in CD40 nucleic acid expression are measured.

Certain Indications

In certain embodiments, the invention provides methods of treating an individual comprising administering one or more pharmaceutical compositions of the present invention. In certain embodiments, the individual has an inflammatory or hyperproliferative disorder. In certain embodiments the invention provides methods for prophylactically reducing CD40 expression in an individual. Certain embodiments include treating an individual in need thereof by administering to an individual a therapeutically effective amount of an antisense compound targeted to a CD40 nucleic acid.

In one embodiment, administration of a therapeutically effective amount of an antisense compound targeted to a CD40 nucleic acid is accompanied by monitoring of eosinophils in an individual, to determine an individual's response to administration of the antisense compound. An individual's response to administration of the antisense compound is used by a physician to determine the amount and duration of therapeutic intervention.

In one embodiment, administration of an antisense compound targeted to a CD40 nucleic acid results in reduction of CD40 expression by at least 15, 20, 25, 30, 35, 40, 45, 50, 55, 60, 65, 70, 75, 80, 85, 90, 95 or 99%, or a range defined by any two of these values. In some embodiments, administration of a CD40 antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a CD40 antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments pharmaceutical composition comprising an antisense compound targeted to CD40 is used for the preparation of a medicament for treating a patient suffering or susceptible to an inflammatory condition or a hyperproliferative disorder.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include steroids and/or chemotherapeutic agents. In certain such embodiments, pharmaceutical agents that may be co-administered with a pharmaceutical composition of the present invention include, but are not limited to prednisone, corticosteroids, and paclitaxel. In certain such embodiments, the agent is administered prior to administration of a pharmaceutical composition of the present invention. In certain such embodiments, the agent is administered following administration of a pharmaceutical composition of the present invention. In certain such embodiments the agent is administered at the same time as a pharmaceutical composition of the present invention. In certain such embodiments the dose of a co-administered agent is the same as the dose that would be administered if the agent was administered alone. In certain such embodiments the dose of a co-administered agent is lower than the dose that would be administered if the agent was administered alone. In certain such embodiments the dose of a co-administered agent is greater than the dose that would be administered if the agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In other embodiments, the co-administration results in effects that are supra-additive of the effects of the compounds when administered alone. In some embodiments, the first compound is an antisense compound. In some embodiments, the second compound is an antisense compound.

EXAMPLES

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Human CD40 In Vitro

Antisense oligonucleotides targeted to a CD40 nucleic acid were tested for their effects on CD40 mRNA in vitro. When cultured cells, grown in a 96-well plate, reached 80% confluency, they were treated with 150 nM antisense oligonucleotide. After a treatment period of approximately 24 hours, RNA was isolated from the cells and CD40 mRNA levels were measured by quantitative real-time PCR, as described herein. CD40 mRNA levels were adjusted according to total RNA content as measured by normalization to RIBOGREEN®. Results are presented as percent inhibition of CD40, relative to untreated control cells in Table 1.

The antisense oligonucleotides were designed as 18-mers with phosphorothioate backbones (internucleoside linkages) throughout. "5' target site" indicates the 5'-most nucleotide which the antisense oligonucleotide is targeted to SEQ ID NO: 1 (GENBANK® Accession No X60592.1). Data are averages from three experiments.

TABLE 1

Inhibition of human CD40 mRNA levels by fully phosphorothioate oligodeoxynucleotides

| Oligo ID | Target SEQ ID NO | Target Start Site | Target Stop Site | Target Region | Sequence (5' to 3') | % Inhibition | SEQ ID NO |
|---|---|---|---|---|---|---|---|
| 18623 | 1 | 18 | 35 | 5' UTR | CCAGGCGGCAGGACCACT | 31 | 5 |
| 18624 | 1 | 20 | 37 | 5' UTR | GACCAGGCGGCAGGACCA | 28 | 6 |
| 18625 | 1 | 26 | 43 | 5' UTR | AGGTGAGACCAGGCGGCA | 22 | 7 |
| 18626 | 1 | 48 | 65 | AUG | CAGAGGCAGACGAACCAT | 0 | 8 |
| 18627 | 1 | 49 | 66 | Coding | GCAGAGGCAGACGAACCA | 0 | 9 |
| 18628 | 1 | 73 | 90 | Coding | GCAAGCAGCCCCAGAGGA | 0 | 10 |
| 18629 | 1 | 78 | 95 | Coding | GGTCAGCAAGCAGCCCCA | 30 | 11 |
| 18630 | 1 | 84 | 101 | Coding | GACAGCGGTCAGCAAGCA | 0 | 12 |
| 18631 | 1 | 88 | 105 | Coding | GATGGACAGCGGTCAGCA | 0 | 13 |
| 18632 | 1 | 92 | 109 | Coding | TCTGGATGGACAGCGGTC | 0 | 14 |
| 18633 | 1 | 98 | 115 | Coding | GGTGGTTCTGGATGGACA | 0 | 15 |
| 18634 | 1 | 101 | 118 | Coding | GTGGGTGGTTCTGGATGG | 0 | 16 |
| 18635 | 1 | 104 | 121 | Coding | GCAGTGGGTGGTTCTGGA | 0 | 17 |
| 18636 | 1 | 152 | 169 | Coding | CACAAAGAACAGCACTGA | 0 | 18 |
| 18637 | 1 | 156 | 173 | Coding | CTGGCACAAAGAACAGCA | 0 | 19 |
| 18638 | 1 | 162 | 179 | Coding | TCCTGGCTGGCACAAAGA | 0 | 20 |
| 18639 | 1 | 165 | 182 | Coding | CTGTCCTGGCTGGCACAA | 5 | 21 |
| 18640 | 1 | 176 | 193 | Coding | CTCACCAGTTTCTGTCCT | 0 | 22 |
| 18641 | 1 | 179 | 196 | Coding | TCACTCACCAGTTTCTGT | 0 | 23 |
| 18642 | 1 | 185 | 202 | Coding | GTGCAGTCACTCACCAGT | 0 | 24 |
| 18643 | 1 | 190 | 207 | Coding | ACTCTGTGCAGTCACTCA | 0 | 25 |
| 18644 | 1 | 196 | 213 | Coding | CAGTGAACTCTGTGCAGT | 5 | 26 |
| 18645 | 1 | 205 | 222 | Coding | ATTCCGTTTCAGTGAACT | 0 | 27 |
| 18646 | 1 | 211 | 228 | Coding | GAAGGCATTCCGTTTCAG | 9 | 28 |
| 18647 | 1 | 222 | 239 | Coding | TTCACCGCAAGGAAGGCA | 0 | 29 |
| 18648 | 1 | 250 | 267 | Coding | CTCTGTTCCAGGTGTCTA | 0 | 30 |
| 18649 | 1 | 267 | 284 | Coding | CTGGTGGCAGTGTGTCTC | 0 | 31 |
| 18650 | 1 | 286 | 303 | Coding | TGGGGTCGCAGTATTTGT | 0 | 32 |
| 18651 | 1 | 289 | 306 | Coding | GGTTGGGGTCGCAGTATT | 0 | 33 |
| 18652 | 1 | 292 | 309 | Coding | CTAGGTTGGGGTCGCAGT | 0 | 34 |
| 18653 | 1 | 318 | 335 | Coding | GGTGCCCTTCTGCTGGAC | 20 | 35 |
| 18654 | 1 | 322 | 339 | Coding | CTGAGGTGCCCTTCTGCT | 16 | 36 |
| 18655 | 1 | 332 | 349 | Coding | GTGTCTGTTTCTGAGGTG | 0 | 37 |
| 18656 | 1 | 334 | 351 | Coding | TGGTGTCTGTTTCTGAGG | 0 | 38 |
| 18657 | 1 | 345 | 362 | Coding | ACAGGTGCAGATGGTGTC | 0 | 39 |
| 18658 | 1 | 348 | 365 | Coding | TTCACAGGTGCAGATGGT | 0 | 40 |
| 18659 | 1 | 360 | 377 | Coding | GTGCCAGCCTTCTTCACA | 6 | 41 |

TABLE 1-continued

Inhibition of human CD40 mRNA levels by fully phosphorothioate oligodeoxynucleotides

| Oligo ID | Target SEQ ID NO | Target Start Site | Target Stop Site | Target Region | Sequence (5' to 3') | % Inhibition | SEQ ID NO |
|---|---|---|---|---|---|---|---|
| 18660 | 1 | 364 | 381 | Coding | TACAGTGCCAGCCTTCTT | 8 | 42 |
| 18661 | 1 | 391 | 408 | Coding | GGACACAGCTCTCACAGG | 0 | 43 |
| 18662 | 1 | 395 | 412 | Coding | TGCAGGACACAGCTCTCA | 0 | 44 |
| 18663 | 1 | 401 | 418 | Coding | GAGCGGTGCAGGACACAG | 0 | 45 |
| 18664 | 1 | 416 | 433 | Coding | AAGCCGGGCGAGCATGAG | 0 | 46 |
| 18665 | 1 | 432 | 449 | Coding | AATCTGCTTGACCCCAAA | 6 | 47 |
| 18666 | 1 | 446 | 463 | Coding | GAAACCCTGTAGCAATC | 0 | 48 |
| 18667 | 1 | 452 | 469 | Coding | GTATCAGAAACCCCTGTA | 0 | 49 |
| 18668 | 1 | 463 | 480 | Coding | GCTCGCAGATGGTATCAG | 0 | 50 |
| 18669 | 1 | 468 | 485 | Coding | GCAGGGCTCGCAGATGGT | 34 | 51 |
| 18670 | 1 | 471 | 488 | Coding | TGGGCAGGGCTCGCAGAT | 0 | 52 |
| 18671 | 1 | 474 | 491 | Coding | GACTGGGCAGGGCTCGCA | 3 | 53 |
| 18672 | 1 | 490 | 507 | Coding | CATTGGAGAAGAAGCCGA | 0 | 54 |
| 18673 | 1 | 497 | 514 | Coding | GATGACACATTGGAGAAG | 0 | 55 |
| 18674 | 1 | 500 | 517 | Coding | GCAGATGACACATTGGAG | 0 | 56 |
| 18675 | 1 | 506 | 523 | Coding | TCGAAAGCAGATGACACA | 0 | 57 |
| 18676 | 1 | 524 | 541 | Coding | GTCCAAGGGTGACATTTT | 8 | 58 |
| 18677 | 1 | 532 | 549 | Coding | CACAGCTTGTCCAAGGGT | 0 | 59 |
| 18678 | 1 | 539 | 556 | Coding | TTGGTCTCACAGCTTGTC | 0 | 60 |
| 18679 | 1 | 546 | 563 | Coding | CAGGTCTTTGGTCTCACA | 7 | 61 |
| 18680 | 1 | 558 | 575 | Coding | CTGTTGCACAACCAGGTC | 19 | 62 |
| 18681 | 1 | 570 | 587 | Coding | GTTTGTGCCTGCCTGTTG | 2 | 63 |
| 18682 | 1 | 575 | 592 | Coding | GTCTTGTTTGTGCCTGCC | 0 | 64 |
| 18683 | 1 | 590 | 607 | Coding | CCACAGACAACATCAGTC | 0 | 65 |
| 18684 | 1 | 597 | 614 | Coding | CTGGGGACCACAGACAAC | 0 | 66 |
| 18685 | 1 | 607 | 624 | Coding | TCAGCCGATCCTGGGGAC | 0 | 67 |
| 18686 | 1 | 621 | 638 | Coding | CACCACCAGGGCTCTCAG | 23 | 68 |
| 18687 | 1 | 626 | 643 | Coding | GGGATCACCACCAGGGCT | 0 | 69 |
| 18688 | 1 | 657 | 674 | Coding | GAGGATGGCAAACAGGAT | 0 | 70 |
| 18689 | 1 | 668 | 685 | Coding | ACCAGCACCAAGAGGATG | 0 | 71 |
| 18690 | 1 | 679 | 696 | Coding | TTTTGATAAAGACCAGCA | 0 | 72 |
| 18691 | 1 | 703 | 720 | Coding | TATTGGTTGGCTTCTTGG | 0 | 73 |
| 18692 | 1 | 729 | 746 | Coding | GGGTTCCTGCTTGGGGTG | 0 | 74 |
| 18693 | 1 | 750 | 767 | Coding | GTCGGGAAAATTGATCTC | 0 | 75 |
| 18694 | 1 | 754 | 771 | Coding | GATCGTCGGGAAAATTGA | 0 | 76 |
| 18695 | 1 | 765 | 782 | Coding | GGAGCCAGGAAGATCGTC | 0 | 77 |

TABLE 1-continued

Inhibition of human CD40 mRNA levels by fully phosphorothioate oligodeoxynucleotides

| Oligo ID | Target SEQ ID NO | Target Start Site | Target Stop Site | Target Region | Sequence (5' to 3') | % Inhibition | SEQ ID NO |
|---|---|---|---|---|---|---|---|
| 18696 | 1 | 766 | 783 | Coding | TGGAGCCAGGAAGATCGT | 0 | 78 |
| 18697 | 1 | 780 | 797 | Coding | TGGAGCAGCAGTGTTGGA | 0 | 79 |
| 18698 | 1 | 796 | 813 | Coding | GTAAAGTCTCCTGCACTG | 0 | 80 |
| 18699 | 1 | 806 | 823 | Coding | TGGCATCCATGTAAAGTC | 0 | 81 |
| 18700 | 1 | 810 | 827 | Coding | CGGTTGGCATCCATGTAA | 0 | 82 |
| 18701 | 1 | 834 | 851 | Coding | CTCTTTGCCATCCTCCTG | 4 | 83 |
| 18702 | 1 | 861 | 878 | Coding | CTGTCTCTCCTGCACTGA | 0 | 84 |
| 18703 | 1 | 873 | 890 | Stop | GGTGCAGCCTCACTGTCT | 0 | 85 |
| 18704 | 1 | 910 | 927 | 3' UTR | AACTGCCTGTTTGCCCAC | 34 | 86 |
| 18705 | 1 | 954 | 971 | 3' UTR | CTTCTGCCTGCACCCCTG | 0 | 87 |
| 18706 | 1 | 976 | 993 | 3' UTR | ACTGACTGGGCATAGCTC | 0 | 88 |

Example 2

Antisense Inhibition of Human CD40 In Vitro

Antisense oligonucleotides targeted to a CD40 nucleic acid were tested for their effects on CD40 mRNA in vitro. T24 cells at a density of 7000 cells per well in a 96-well plate were treated with 150 nM antisense oligonucleotide. After a treatment period of approximately 24 hours, RNA was isolated from the cells and CD40 mRNA levels were measured by quantitative real-time PCR, as described herein. CD40 mRNA levels were adjusted according to GAPDH content, a housekeeping gene. Results are presented as percent inhibition of CD40, relative to untreated control cells in Table 2.

The antisense oligonucleotides were designed as 4-10-4 gapmers, where the gap segment comprises 2'-deoxynucleotides and each wing segment comprises 2'-MOE nucleotides and 5-methylcytosine substitutions. The antisense oligonucleotides comprise phosphorothioate backbones (internucleoside linkages) throughout. "5' target site" indicates the 5'-most nucleotide which the antisense oligonucleotide is targeted to SEQ ID NO: 1 (GENBANK® Accession No X60592.1). Data are averages from three experiments. "ND" indicates a value was not determined.

TABLE 2

Inhibition of human CD40 mRNA levels by chimeric oligonucleotides having 4-10-4 MOE wings and deoxy gap

| OligoID | Target SEQ ID NO | Target Start Site | Target Stop Site | Target Region | Sequence (5' to 3') | % Inhibition | SEQ ID NO |
|---|---|---|---|---|---|---|---|
| 19211 | 1 | 18 | 35 | 5' UTR | CCAGGCGGCAGGACCACT | 76 | 5 |
| 19212 | 1 | 20 | 37 | 5' UTR | GACCAGGCGGCAGGACCA | 77 | 6 |
| 19213 | 1 | 26 | 43 | 5' UTR | AGGTGAGACCAGGCGGCA | 81 | 7 |
| 19214 | 1 | 48 | 65 | AUG | CAGAGGCAGACGAACCAT | 24 | 8 |
| 19215 | 1 | 49 | 66 | Coding | GCAGAGGCAGACGAACCA | 46 | 9 |
| 19216 | 1 | 73 | 90 | Coding | GCAAGCAGCCCCAGAGGA | 66 | 10 |
| 19217 | 1 | 78 | 95 | Coding | GGTCAGCAAGCAGCCCCA | 75 | 11 |
| 19218 | 1 | 84 | 101 | Coding | GACAGCGGTCAGCAAGCA | 67 | 12 |
| 19219 | 1 | 88 | 105 | Coding | GATGGACAGCGGTCAGCA | 65 | 13 |
| 19220 | 1 | 92 | 109 | Coding | TCTGGATGGACAGCGGTC | 79 | 14 |
| 19221 | 1 | 98 | 115 | Coding | GGTGGTTCTGGATGGACA | 81 | 15 |
| 19222 | 1 | 101 | 118 | Coding | GTGGGTGGTTCTGGATGG | 58 | 16 |

TABLE 2-continued

Inhibition of human CD40 mRNA levels by chimeric oligonucleotides having 4-10-4 MOE wings and deoxy gap

| OligoID | Target SEQ ID NO | Target Start Site | Target Stop Site | Target Region | Sequence (5' to 3') | % Inhibition | SEQ ID NO |
|---|---|---|---|---|---|---|---|
| 19223 | 1 | 104 | 121 | Coding | GCAGTGGGTGGTTCTGGA | 74 | 17 |
| 19224 | 1 | 152 | 169 | Coding | CACAAAGAACAGCACTGA | 40 | 18 |
| 19225 | 1 | 156 | 173 | Coding | CTGGCACAAAGAACAGCA | 60 | 19 |
| 19226 | 1 | 162 | 179 | Coding | TCCTGGCTGGCACAAAGA | 10 | 20 |
| 19227 | 1 | 165 | 182 | Coding | CTGTCCTGGCTGGCACAA | 24 | 21 |
| 19228 | 1 | 176 | 193 | Coding | CTCACCAGTTTCTGTCCT | 22 | 22 |
| 19229 | 1 | 179 | 196 | Coding | TCACTCACCAGTTTCTGT | 41 | 23 |
| 19230 | 1 | 185 | 202 | Coding | GTGCAGTCACTCACCAGT | 82 | 24 |
| 19231 | 1 | 190 | 207 | Coding | ACTCTGTGCAGTCACTCA | 38 | 25 |
| 19232 | 1 | 196 | 213 | Coding | CAGTGAACTCTGTGCAGT | 40 | 26 |
| 19233 | 1 | 205 | 222 | Coding | ATTCCGTTTCAGTGAACT | 56 | 27 |
| 19234 | 1 | 211 | 228 | Coding | GAAGGCATTCCGTTTCAG | 32 | 28 |
| 19235 | 1 | 222 | 239 | Coding | TTCACCGCAAGGAAGGCA | 61 | 29 |
| 19236 | 1 | 250 | 267 | Coding | CTCTGTTCCAGGTGTCTA | 62 | 30 |
| 19237 | 1 | 267 | 284 | Coding | CTGGTGGCAGTGTGTCTC | 70 | 31 |
| 19238 | 1 | 286 | 303 | Coding | TGGGGTCGCAGTATTTGT | 0 | 32 |
| 19239 | 1 | 289 | 306 | Coding | GGTTGGGGTCGCAGTATT | 19 | 33 |
| 19240 | 1 | 292 | 309 | Coding | CTAGGTTGGGGTCGCAGT | 36 | 34 |
| 19241 | 1 | 318 | 335 | Coding | GGTGCCCTTCTGCTGGAC | 79 | 35 |
| 19242 | 1 | 322 | 339 | Coding | CTGAGGTGCCCTTCTGCT | 70 | 36 |
| 19243 | 1 | 332 | 349 | Coding | GTGTCTGTTTCTGAGGTG | 63 | 37 |
| 19244 | 1 | 334 | 351 | Coding | TGGTGTCTGTTTCTGAGG | 43 | 38 |
| 19245 | 1 | 345 | 362 | Coding | ACAGGTGCAGATGGTGTC | 73 | 39 |
| 19246 | 1 | 348 | 365 | Coding | TTCACAGGTGCAGATGGT | 48 | 40 |
| 19247 | 1 | 360 | 377 | Coding | GTGCCAGCCTTCTTCACA | 61 | 41 |
| 19248 | 1 | 364 | 381 | Coding | TACAGTGCCAGCCTTCTT | 47 | 42 |
| 19249 | 1 | 391 | 408 | Coding | GGACACAGCTCTCACAGG | 0 | 43 |
| 19250 | 1 | 395 | 412 | Coding | TGCAGGACACAGCTCTCA | 52 | 44 |
| 19251 | 1 | 401 | 418 | Coding | GAGCGGTGCAGGACACAG | 50 | 45 |
| 19252 | 1 | 416 | 433 | Coding | AAGCCGGGCGAGCATGAG | 32 | 46 |
| 19253 | 1 | 432 | 449 | Coding | AATCTGCTTGACCCCAAA | 0 | 47 |
| 19254 | 1 | 446 | 463 | Coding | GAAACCCCTGTAGCAATC | 0 | 48 |
| 19255 | 1 | 452 | 469 | Coding | GTATCAGAAACCCCTGTA | 36 | 49 |
| 19256 | 1 | 463 | 480 | Coding | GCTCGCAGATGGTATCAG | 65 | 50 |
| 19257 | 1 | 468 | 485 | Coding | GCAGGGCTCGCAGATGGT | 75 | 51 |
| 19258 | 1 | 471 | 488 | Coding | TGGGCAGGGCTCGCAGAT | 0 | 52 |

TABLE 2-continued

Inhibition of human CD40 mRNA levels by chimeric oligonucleotides having 4-10-4 MOE wings and deoxy gap

| OligoID | Target SEQ ID NO | Target Start Site | Target Stop Site | Target Region | Sequence (5' to 3') | % Inhibition | SEQ ID NO |
|---|---|---|---|---|---|---|---|
| 19259 | 1 | 474 | 491 | Coding | GACTGGGCAGGGCTCGCA | 82 | 53 |
| 19260 | 1 | 490 | 507 | Coding | CATTGGAGAAGAAGCCGA | 41 | 54 |
| 19261 | 1 | 497 | 514 | Coding | GATGACACATTGGAGAAG | 14 | 55 |
| 19262 | 1 | 500 | 517 | Coding | GCAGATGACACATTGGAG | 78 | 56 |
| 19263 | 1 | 506 | 523 | Coding | TCGAAAGCAGATGACACA | 59 | 57 |
| 19264 | 1 | 524 | 541 | Coding | GTCCAAGGGTGACATTTT | 71 | 58 |
| 19265 | 1 | 532 | 549 | Coding | CACAGCTTGTCCAAGGGT | 0 | 59 |
| 19266 | 1 | 539 | 556 | Coding | TTGGTCTCACAGCTTGTC | 46 | 60 |
| 19267 | 1 | 546 | 563 | Coding | CAGGTCTTTGGTCTCACA | 64 | 61 |
| 19268 | 1 | 558 | 575 | Coding | CTGTTGCACAACCAGGTC | 82 | 62 |
| 19269 | 1 | 570 | 587 | Coding | GTTTGTGCCTGCCTGTTG | 70 | 63 |
| 19270 | 1 | 575 | 592 | Coding | GTCTTGTTTGTGCCTGCC | 69 | 64 |
| 19271 | 1 | 590 | 607 | Coding | CCACAGACAACATCAGTC | 11 | 65 |
| 19272 | 1 | 597 | 614 | Coding | CTGGGGACCACAGACAAC | 9 | 66 |
| 19273 | 1 | 607 | 624 | Coding | TCAGCCGATCCTGGGGAC | 0 | 67 |
| 19274 | 1 | 621 | 638 | Coding | CACCACCAGGGCTCTCAG | 23 | 68 |
| 19275 | 1 | 626 | 643 | Coding | GGGATCACCACCAGGGCT | 58 | 69 |
| 19276 | 1 | 657 | 674 | Coding | GAGGATGGCAAACAGGAT | 49 | 70 |
| 19277 | 1 | 668 | 685 | Coding | ACCAGCACCAAGAGGATG | ND | 71 |
| 19278 | 1 | 679 | 696 | Coding | TTTTGATAAAGACCAGCA | 31 | 72 |
| 19279 | 1 | 703 | 720 | Coding | TATTGGTTGGCTTCTTGG | 49 | 73 |
| 19280 | 1 | 729 | 746 | Coding | GGGTTCCTGCTTGGGGTG | 14 | 74 |
| 19281 | 1 | 750 | 767 | Coding | GTCGGGAAAATTGATCTC | 55 | 75 |
| 19282 | 1 | 754 | 771 | Coding | GATCGTCGGGAAAATTGA | 0 | 76 |
| 19283 | 1 | 765 | 782 | Coding | GGAGCCAGGAAGATCGTC | 69 | 77 |
| 19284 | 1 | 766 | 783 | Coding | TGGAGCCAGGAAGATCGT | 54 | 78 |
| 19285 | 1 | 780 | 797 | Coding | TGGAGCAGCAGTGTTGGA | 15 | 79 |
| 19286 | 1 | 796 | 813 | Coding | GTAAAGTCTCCTGCACTG | 31 | 80 |
| 19287 | 1 | 806 | 823 | Coding | TGGCATCCATGTAAAGTC | 65 | 81 |
| 19288 | 1 | 810 | 827 | Coding | CGGTTGGCATCCATGTAA | 34 | 82 |
| 19289 | 1 | 834 | 851 | Coding | CTCTTTGCCATCCTCCTG | 42 | 83 |
| 19290 | 1 | 861 | 878 | Coding | CTGTCTCTCCTGCACTGA | 26 | 84 |
| 19291 | 1 | 873 | 890 | Stop | GGTGCAGCCTCACTGTCT | 76 | 85 |
| 19292 | 1 | 910 | 927 | 3' UTR | AACTGCCTGTTTGCCCAC | 63 | 86 |

TABLE 2-continued

Inhibition of human CD40 mRNA levels by chimeric oligonucleotides having 4-10-4 MOE wings and deoxy gap

| OligoID | Target SEQ ID NO | Target Start Site | Target Stop Site | Target Region | Sequence (5' to 3') | % Inhibition | SEQ ID NO |
|---|---|---|---|---|---|---|---|
| 19293 | 1 | 954 | 971 | 3' UTR | CTTCTGCCTGCACCCCTG | 0 | 87 |
| 19294 | 1 | 976 | 993 | 3' UTR | ACTGACTGGGCATAGCTC | 12 | 88 |

Example 3

Antisense Inhibition of Human CD40

Antisense oligonucleotides targeted to a CD40 nucleic acid were tested for their effects on CD40 mRNA in vitro. T24 cells at a density of 7000 cells per well in a 96-well plate were treated with 100 nM of antisense oligonucleotide. After a treatment period of approximately 24 hours, RNA was isolated from the cells and CD40 mRNA levels were measured by quantitative real-time PCR, as described herein. CD40 mRNA levels were adjusted according to GAPDH content, a housekeeping gene. Results are presented as percent inhibition of CD40, relative to untreated control cells in Table 3.

The antisense oligonucleotides were designed as 4-10-4 gapmers, where the gap segment comprises 2'-deoxynucleotides and each wing segment comprises 2'-MOE nucleotides. The antisense oligonucleotides comprise phosphorothioate backbones (internucleoside linkages) and 5-methylcytosine substitutions throughout. "5' target site" indicates the 5'-most nucleotide which the antisense oligonucleotide is targeted to SEQ ID NO: 1 (GENBANK Accession No. X60592.1), SEQ ID NO: 2 (GENBANK® Accession No. H50598.1), and SEQ ID NO: 3 (GENBANK® Accession No. AA203290.1).

TABLE 3

Inhibition of human CD40 mRNA levels by chimeric oligonucleotides having 4-10-4 MOE wings and deoxy gap

| Oligo ID | Target SEQ ID NO | Target Start Site | Target Stop Site | Sequence (5' to 3') | % Inhibition | SEQ ID NO |
|---|---|---|---|---|---|---|
| 26162 | 1 | 66 | 83 | GCCCCAGAGGACGCACTG | 0 | 89 |
| 26163 | 1 | 70 | 87 | AGCAGCCCCAGAGGACGC | 98 | 90 |
| 26164 | 1 | 74 | 91 | AGCAAGCAGCCCCAGAGG | 47 | 91 |
| 26165 | 1 | 80 | 97 | GCGGTCAGCAAGCAGCCC | 54 | 92 |
| 26167 | 1 | 95 | 112 | GGTTCTGGATGGACAGCG | 66 | 93 |
| 26168 | 1 | 102 | 119 | AGTGGGTGGTTCTGGATG | 26 | 94 |
| 26169 | 1 | 141 | 158 | GCACTGACTGTTTATTAG | 43 | 95 |
| 26170 | 1 | 154 | 171 | GGCACAAAGAACAGCACT | 53 | 96 |
| 26171 | 1 | 164 | 181 | TGTCCTGGCTGGCACAAA | 29 | 97 |
| 26172 | 1 | 171 | 188 | CAGTTTCTGTCCTGGCTG | 48 | 98 |
| 26173 | 1 | 180 | 197 | GTCACTCACCAGTTTCTG | 47 | 99 |
| 26174 | 1 | 210 | 227 | AAGGCATTCCGTTTCAGT | 57 | 100 |
| 26175 | 1 | 224 | 241 | CTTTCACCGCAAGGAAGG | 34 | 101 |
| 26176 | 1 | 250 | 267 | CTCTGTTCCAGGTGTCTA | 78 | 30 |
| 26177 | 1 | 257 | 274 | TGTGTCTCTCTGTTCCAG | 57 | 102 |
| 26178 | 1 | 264 | 281 | GTGGCAGTGTGTCTCTCT | 0 | 103 |
| 26179 | 1 | 314 | 331 | CCCTTCTGCTGGACCCGA | 58 | 104 |
| 26180 | 1 | 321 | 338 | TGAGGTGCCCTTCTGCTG | 69 | 105 |
| 26181 | 1 | 329 | 346 | TCTGTTTCTGAGGTGCCC | 44 | 106 |
| 26182 | 1 | 336 | 353 | GATGGTGTCTGTTTCTGA | 12 | 107 |

TABLE 3-continued

Inhibition of human CD40 mRNA levels by chimeric oligonucleotides having 4-10-4 MOE wings and deoxy gap

| Oligo ID | Target SEQ ID NO | Target Start Site | Target Stop Site | Sequence (5' to 3') | % Inhibition | SEQ ID NO |
|---|---|---|---|---|---|---|
| 26183 | 1 | 364 | 381 | TACAGTGCCAGCCTTCTT | 14 | 42 |
| 26184 | 1 | 445 | 462 | AAACCCCTGTAGCAATCT | 15 | 108 |
| 26185 | 1 | 460 | 477 | CGCAGATGGTATCAGAAA | 53 | 109 |
| 26186 | 1 | 469 | 486 | GGCAGGGCTCGCAGATGG | 79 | 110 |
| 26202 | 1 | 485 | 502 | GAGAAGAAGCCGACTGGG | 0 | 111 |
| 26187 | 1 | 487 | 504 | TGGAGAAGAAGCCGACTG | 23 | 112 |
| 26204 | 1 | 489 | 506 | ATTGGAGAAGAAGCCGAC | 0 | 113 |
| 26205 | 1 | 491 | 508 | ACATTGGAGAAGAAGCCG | 4 | 114 |
| 26206 | 1 | 493 | 510 | ACACATTGGAGAAGAAGC | 0 | 115 |
| 26207 | 1 | 495 | 512 | TGACACATTGGAGAAGAA | 46 | 116 |
| 26188 | 1 | 496 | 513 | ATGACACATTGGAGAAGA | 0 | 117 |
| 26208 | 1 | 497 | 514 | GATGACACATTGGAGAAG | 0 | 55 |
| 26189 | 1 | 503 | 520 | AAAGCAGATGACACATTG | 6 | 118 |
| 26209 | 1 | 524 | 541 | GTCCAAGGGTGACATTTT | 53 | 58 |
| 26210 | 1 | 545 | 562 | AGGTCTTTGGTCTCACAG | 81 | 119 |
| 26211 | 1 | 555 | 572 | TTGCACAACCAGGTCTTT | 48 | 120 |
| 26212 | 1 | 570 | 587 | GTTTGTGCCTGCCTGTTG | 76 | 63 |
| 26213 | 1 | 572 | 589 | TTGTTTGTGCCTGCCTGT | 50 | 121 |
| 26214 | 1 | 574 | 591 | TCTTGTTTGTGCCTGCCT | 87 | 122 |
| 26215 | 1 | 576 | 593 | AGTCTTGTTTGTGCCTGC | 83 | 123 |
| 26216 | 1 | 577 | 594 | CAGTCTTGTTTGTGCCTG | 80 | 124 |
| 26217 | 1 | 578 | 595 | TCAGTCTTGTTTGTGCCT | 88 | 125 |
| 26218 | 1 | 580 | 597 | CATCAGTCTTGTTTGTGC | 52 | 126 |
| 26219 | 1 | 590 | 607 | CCACAGACAACATCAGTC | 16 | 65 |
| 26220 | 1 | 592 | 609 | GACCACAGACAACATCAG | 11 | 127 |
| 26221 | 1 | 594 | 611 | GGGACCACAGACAACATC | 40 | 128 |
| 26222 | 1 | 622 | 639 | TCACCACCAGGGCTCTCA | 37 | 129 |
| 26223 | 1 | 624 | 641 | GATCACCACCAGGGCTCT | 82 | 130 |
| 26224 | 1 | 658 | 675 | AGAGGATGGCAAACAGGA | 33 | 131 |
| 26225 | 1 | 659 | 676 | AAGAGGATGGCAAACAGG | 0 | 132 |
| 26226 | 1 | 660 | 677 | CAAGAGGATGGCAAACAG | 0 | 133 |
| 26227 | 1 | 669 | 686 | GACCAGCACCAAGAGGAT | 57 | 134 |
| 26228 | 1 | 671 | 688 | AAGACCAGCACCAAGAGG | 35 | 135 |
| 26229 | 1 | 673 | 690 | TAAAGACCAGCACCAAGA | 13 | 136 |
| 26230 | 1 | 676 | 693 | TGATAAAGACCAGCACCA | 0 | 137 |
| 26231 | 1 | 678 | 695 | TTTGATAAAGACCAGCAC | 26 | 138 |

TABLE 3-continued

Inhibition of human CD40 mRNA levels by chimeric oligonucleotides having 4-10-4 MOE wings and deoxy gap

| Oligo ID | Target SEQ ID NO | Target Start Site | Target Stop Site | Sequence (5' to 3') | % Inhibition | SEQ ID NO |
|---|---|---|---|---|---|---|
| 26232 | 2 | 375 | 392 | ACTCTCTTTGCCCATCCT | 0 | 139 |
| 26233 | 2 | 377 | 394 | CGACTCTCTTTGCCCATC | 31 | 140 |
| 26234 | 2 | 380 | 397 | ATGCGACTCTCTTTGCCC | 12 | 141 |
| 26235 | 2 | 382 | 399 | AAATGCGACTCTCTTTGC | 36 | 142 |
| 26236 | 2 | 385 | 402 | CTGAAATGCGACTCTCTT | 51 | 143 |
| 26237 | 2 | 387 | 404 | AACTGAAATGCGACTCTC | 0 | 144 |
| 26238 | 2 | 406 | 423 | CTTCACTGTCTCTCCCTG | 0 | 145 |
| 26239 | 2 | 407 | 424 | CCTTCACTGTCTCTCCCT | 56 | 146 |
| 26240 | 2 | 409 | 426 | AACCTTCACTGTCTCTCC | 0 | 147 |
| 26190 | 3 | 520 | 537 | GATCACCACAGGCTCTCA | 0 | 148 |
| 26191 | 3 | 565 | 582 | TGATAAGACAGCACCAAG | 9 | 149 |
| 26192 | 3 | 584 | 601 | GGTAGTTCTTGCCACTTT | 0 | 150 |
| 26193 | 3 | 593 | 610 | GGGCCTATGGGTAGTTCT | 0 | 151 |
| 26194 | 3 | 617 | 634 | ATTATCTCTGGGTCTGCT | 9 | 152 |
| 26195 | 3 | 646 | 663 | ACTGACACATTTGAGCAG | 0 | 153 |
| 26196 | 3 | 654 | 671 | GACTCCCTACTGACACAT | 0 | 154 |
| 26197 | 3 | 689 | 706 | CAAAGAGCGGTTCTCCAC | 0 | 155 |
| 26198 | 3 | 696 | 713 | AATTCTCCAAAGAGCGGT | 0 | 156 |
| 26199 | 3 | 728 | 745 | TCTTGACATCCTTTTCAT | 0 | 157 |
| 26200 | 3 | 736 | 753 | CCCACCTATCTTGACATC | 0 | 158 |
| 26201 | 3 | 791 | 808 | AGGCCGAGAGTTCAAAAT | 0 | 159 |

Example 4

Antisense Inhibition of Human CD40

Antisense oligonucleotides targeted to a CD40 nucleic acid were tested for their effects on CD40 mRNA in vitro. A549 cells at a density of 5000 cells per well in a 96-well plate were treated with 120 nM of antisense oligonucleotide. After a treatment period of approximately 24 hours, RNA was isolated from the cells and CD40 mRNA levels were measured by quantitative real-time PCR, as described herein. CD40 primer probe set LTS37 was used to measure mRNA levels. CD40 mRNA levels were adjusted according to total RNA content as measured by RIBOGREEN®. Results are presented as percent inhibition of CD40, relative to untreated control cells in Table 4.

The antisense oligonucleotides were designed as 4-10-4 gapmers, 5-10-5 gapmers, or 2-15-3 gapmers, where the gap segment comprises 2'-deoxynucleotides and each wing segment comprises 2'-MOE nucleotides. The motif for each compound is indicated by the column labeled "motif." The antisense oligonucleotides comprise phosphorothioate backbones (internucleoside linkages) and 5-methylcytosine substitutions throughout. "5' target site" indicates the 5'-most nucleotide which the antisense oligonucleotide is targeted to SEQ ID NO: 1 (GENBANK Accession No. X60592.1) or SEQ ID NO: 4 (nucleotides 9797000 to 9813000 of GENBANK Accession No. NT_011362.9).

TABLE 4

Inhibition of human CD40 mRNA levels by chimeric oligonucleotides having 4-10-4 MOE wings and deoxy gap, 5-10-5 MOE wings and deoxy gap, and 2-15-3 MOE wings and deoxy gap

| Oligo ID | Target SEQ ID NO | Motif | Target Start Site | Target Stop Site | Sequence (5' to 3') | % Inhibition | SEQ ID NO |
|---|---|---|---|---|---|---|---|
| 26163 | 4 | 4-10-4 | 2914 | 2931 | AGCAGCCCCAGAGGACGC | 74 | 90 |
| 396243 | 4 | 5-10-5 | 2728 | 2747 | CCAGCAATTCACCGCGCAGG | 0 | 160 |
| 396320 | 4 | 2-15-3 | 2728 | 2747 | CCAGCAATTCACCGCGCAGG | 0 | 160 |
| 396199 | 4 | 5-10-5 | 2892 | 2911 | TGCAGAGGCAGACGAACCAT | 75 | 161 |
| 396276 | 4 | 2-15-3 | 2892 | 2911 | TGCAGAGGCAGACGAACCAT | 55 | 161 |
| 396200 | 4 | 5-10-5 | 2904 | 2923 | CAGAGGACGCACTGCAGAGG | 79 | 162 |
| 396277 | 4 | 2-15-3 | 2904 | 2923 | CAGAGGACGCACTGCAGAGG | 69 | 162 |
| 396201 | 4 | 5-10-5 | 2913 | 2932 | AAGCAGCCCCAGAGGACGCA | 76 | 163 |
| 396278 | 4 | 2-15-3 | 2913 | 2932 | AAGCAGCCCCAGAGGACGCA | 78 | 163 |
| 396202 | 4 | 5-10-5 | 2924 | 2943 | CAGCGGTCAGCAAGCAGCCC | 68 | 164 |
| 396279 | 4 | 2-15-3 | 2924 | 2943 | CAGCGGTCAGCAAGCAGCCC | 88 | 164 |
| 396244 | 4 | 5-10-5 | 2928 | 2947 | CTCACAGCGGTCAGCAAGCA | 86 | 165 |
| 396321 | 4 | 2-15-3 | 2928 | 2947 | CTCACAGCGGTCAGCAAGCA | 75 | 165 |
| 396245 | 4 | 5-10-5 | 3349 | 3368 | GCTGGCAAGGAGATGATAAC | 51 | 166 |
| 396322 | 4 | 2-15-3 | 3349 | 3368 | GCTGGCAAGGAGATGATAAC | 54 | 166 |
| 396246 | 4 | 5-10-5 | 3480 | 3499 | AGGTTGGAACACCCAAGATA | 69 | 167 |
| 396323 | 4 | 2-15-3 | 3480 | 3499 | AGGTTGGAACACCCAAGATA | 78 | 167 |
| 396247 | 4 | 5-10-5 | 3649 | 3668 | GGAGAAACCCCTGGTTTCTC | 45 | 168 |
| 396324 | 4 | 2-15-3 | 3649 | 3668 | GGAGAAACCCCTGGTTTCTC | 26 | 168 |
| 396248 | 4 | 5-10-5 | 3860 | 3879 | TCATTCCTGCCCAGGCTTCA | 43 | 169 |
| 396325 | 4 | 2-15-3 | 3860 | 3879 | TCATTCCTGCCCAGGCTTCA | 39 | 169 |
| 396249 | 4 | 5-10-5 | 3950 | 3969 | TCAGGTGAAAGTGAAAGCTG | 68 | 170 |
| 396326 | 4 | 2-15-3 | 3950 | 3969 | TCAGGTGAAAGTGAAAGCTG | 69 | 170 |
| 396250 | 4 | 5-10-5 | 4490 | 4509 | TACCATCTTCAAACACATGA | 79 | 171 |
| 396327 | 4 | 2-15-3 | 4490 | 4509 | TACCATCTTCAAACACATGA | 71 | 171 |
| 396251 | 4 | 5-10-5 | 4604 | 4623 | TTACCCAAAATGGGAAAGGA | 86 | 172 |
| 396328 | 4 | 2-15-3 | 4604 | 4623 | TTACCCAAAATGGGAAAGGA | 48 | 172 |
| 396252 | 4 | 5-10-5 | 4810 | 4829 | GAAAGAATACATGTATATGG | 72 | 173 |
| 396329 | 4 | 2-15-3 | 4810 | 4829 | GAAAGAATACATGTATATGG | 10 | 173 |
| 396253 | 4 | 5-10-5 | 4944 | 4963 | AGAGTCAGACAGCTTTAGAC | 78 | 174 |
| 396330 | 4 | 2-15-3 | 4944 | 4963 | AGAGTCAGACAGCTTTAGAC | 79 | 174 |
| 396254 | 4 | 5-10-5 | 5651 | 5670 | GTACCACCCATGCTATTAAT | 79 | 175 |
| 396331 | 4 | 2-15-3 | 5651 | 5670 | GTACCACCCATGCTATTAAT | 84 | 175 |
| 396255 | 4 | 5-10-5 | 5740 | 5759 | ACAGTGACAGAGTCCAAATG | 85 | 176 |
| 396332 | 4 | 2-15-3 | 5740 | 5759 | ACAGTGACAGAGTCCAAATG | 75 | 176 |
| 396256 | 4 | 5-10-5 | 5830 | 5849 | AATGTAAAGCTGGAAGGGTA | 52 | 177 |

TABLE 4-continued

Inhibition of human CD40 mRNA levels by chimeric oligonucleotides having 4-10-4 MOE wings and deoxy gap, 5-10-5 MOE wings and deoxy gap, and 2-15-3 MOE wings and deoxy gap

| Oligo ID | Target SEQ ID NO | Motif | Target Start Site | Target Stop Site | Sequence (5' to 3') | % Inhibition | SEQ ID NO |
|---|---|---|---|---|---|---|---|
| 396333 | 4 | 2-15-3 | 5830 | 5849 | AATGTAAAGCTGGAAGGGTA | 37 | 177 |
| 396257 | 4 | 5-10-5 | 5964 | 5983 | GGGCTATGTTTAGCACTTGG | 79 | 178 |
| 396334 | 4 | 2-15-3 | 5964 | 5983 | GGGCTATGTTTAGCACTTGG | 73 | 178 |
| 396258 | 4 | 5-10-5 | 6078 | 6097 | GGGCTTGATGCCTGAGTCAT | 73 | 179 |
| 396335 | 4 | 2-15-3 | 6078 | 6097 | GGGCTTGATGCCTGAGTCAT | 40 | 179 |
| 396259 | 4 | 5-10-5 | 6251 | 6270 | TGAAGTGCAAGTCAAAACAG | 52 | 180 |
| 396336 | 4 | 2-15-3 | 6251 | 6270 | TGAAGTGCAAGTCAAAACAG | 44 | 180 |
| 396260 | 4 | 5-10-5 | 6332 | 6351 | GCAATTTGAAGGGATCTTGA | 68 | 181 |
| 396337 | 4 | 2-15-3 | 6332 | 6351 | GCAATTTGAAGGGATCTTGA | 42 | 181 |
| 396203 | 4 | 5-10-5 | 6374 | 6393 | CATGCAGTGGGTGGTTCTGG | 77 | 182 |
| 396280 | 4 | 2-15-3 | 6374 | 6393 | CATGCAGTGGGTGGTTCTGG | 83 | 182 |
| 396204 | 4 | 5-10-5 | 6385 | 6404 | GTTTTTCTCTGCATGCAGTG | 78 | 183 |
| 396281 | 4 | 2-15-3 | 6385 | 6404 | GTTTTTCTCTGCATGCAGTG | 70 | 183 |
| 396205 | 4 | 5-10-5 | 6424 | 6443 | GCTGGCACAAAGAACAGCAC | 61 | 184 |
| 396282 | 4 | 2-15-3 | 6424 | 6443 | GCTGGCACAAAGAACAGCAC | 65 | 184 |
| 396261 | 4 | 5-10-5 | 6709 | 6728 | CACTAACCACACAATGATCA | 85 | 185 |
| 396338 | 4 | 2-15-3 | 6709 | 6728 | CACTAACCACACAATGATCA | 62 | 185 |
| 396206 | 4 | 5-10-5 | 6787 | 6806 | TGTGCAGTCACTCACCAGTT | 83 | 186 |
| 396283 | 4 | 2-15-3 | 6787 | 6806 | TGTGCAGTCACTCACCAGTT | 72 | 186 |
| 396207 | 4 | 5-10-5 | 6838 | 6857 | GTCTAGGAATTCGCTTTCAC | 95 | 187 |
| 396284 | 4 | 2-15-3 | 6838 | 6857 | GTCTAGGAATTCGCTTTCAC | 85 | 187 |
| 396208 | 4 | 5-10-5 | 6843 | 6862 | CAGGTGTCTAGGAATTCGCT | 98 | 188 |
| 396285 | 4 | 2-15-3 | 6843 | 6862 | CAGGTGTCTAGGAATTCGCT | 90 | 188 |
| 396209 | 4 | 5-10-5 | 6883 | 6902 | GTCGCAGTATTTGTGCTGGT | 84 | 189 |
| 396286 | 4 | 2-15-3 | 6883 | 6902 | GTCGCAGTATTTGTGCTGGT | 86 | 189 |
| 396262 | 4 | 5-10-5 | 7154 | 7173 | ACCCGAAGCCCTAGGTCTGA | 92 | 190 |
| 396339 | 4 | 2-15-3 | 7154 | 7173 | ACCCGAAGCCCTAGGTCTGA | 84 | 190 |
| 396210 | 4 | 5-10-5 | 7158 | 7177 | CTGGACCCGAAGCCCTAGGT | 82 | 191 |
| 396287 | 4 | 2-15-3 | 7158 | 7177 | CTGGACCCGAAGCCCTAGGT | 90 | 191 |
| 396211 | 4 | 5-10-5 | 7163 | 7182 | TTCTGCTGGACCCGAAGCCC | 65 | 192 |
| 396288 | 4 | 2-15-3 | 7163 | 7182 | TTCTGCTGGACCCGAAGCCC | 80 | 192 |
| 396212 | 4 | 5-10-5 | 7204 | 7223 | CTTCTTCACAGGTGCAGATG | 79 | 193 |
| 396289 | 4 | 2-15-3 | 7204 | 7223 | CTTCTTCACAGGTGCAGATG | 72 | 193 |
| 396263 | 4 | 5-10-5 | 7590 | 7609 | AGCCAGTGGCCAGGCAGGAC | 70 | 194 |
| 396340 | 4 | 2-15-3 | 7590 | 7609 | AGCCAGTGGCCAGGCAGGAC | 56 | 194 |
| 396214 | 4 | 5-10-5 | 7704 | 7723 | GAAGAAGCCGACTGGGCAGG | 76 | 195 |

TABLE 4-continued

Inhibition of human CD40 mRNA levels by chimeric oligonucleotides having 4-10-4 MOE wings and deoxy gap, 5-10-5 MOE wings and deoxy gap, and 2-15-3 MOE wings and deoxy gap

| Oligo ID | Target SEQ ID NO | Motif | Target Start Site | Target Stop Site | Sequence (5' to 3') | % Inhibition | SEQ ID NO |
|---|---|---|---|---|---|---|---|
| 396291 | 4 | 2-15-3 | 7704 | 7723 | GAAGAAGCCGACTGGGCAGG | 80 | 195 |
| 396215 | 4 | 5-10-5 | 7709 | 7728 | TTGGAGAAGAAGCCGACTGG | 77 | 196 |
| 396292 | 4 | 2-15-3 | 7709 | 7728 | TTGGAGAAGAAGCCGACTGG | 80 | 196 |
| 396216 | 4 | 5-10-5 | 7718 | 7737 | GATGACACATTGGAGAAGAA | 76 | 197 |
| 396293 | 4 | 2-15-3 | 7718 | 7737 | GATGACACATTGGAGAAGAA | 65 | 197 |
| 396264 | 4 | 5-10-5 | 7953 | 7972 | TGTCTATTACCTCAAAGAGA | 89 | 198 |
| 396341 | 4 | 2-15-3 | 7953 | 7972 | TGTCTATTACCTCAAAGAGA | 72 | 198 |
| 396265 | 4 | 5-10-5 | 8492 | 8511 | ACAGTGTGTTCAGAGGATTG | 82 | 199 |
| 396342 | 4 | 2-15-3 | 8492 | 8511 | ACAGTGTGTTCAGAGGATTG | 67 | 199 |
| 396266 | 4 | 5-10-5 | 9755 | 9774 | ACAATACACTTTACATGTTT | 90 | 200 |
| 396343 | 4 | 2-15-3 | 9755 | 9774 | ACAATACACTTTACATGTTT | 63 | 200 |
| 396267 | 4 | 5-10-5 | 10414 | 10433 | ATTGTGTCTTTAGAACCAGA | 84 | 201 |
| 396344 | 4 | 2-15-3 | 10414 | 10433 | ATTGTGTCTTTAGAACCAGA | 59 | 201 |
| 396268 | 4 | 5-10-5 | 10528 | 10547 | GGGCCCTAAAGGATGTAAAA | 34 | 202 |
| 396345 | 4 | 2-15-3 | 10528 | 10547 | GGGCCCTAAAGGATGTAAAA | 76 | 202 |
| 396217 | 4 | 5-10-5 | 11218 | 11237 | CAGTCTTGTTTGTGCCTGCC | 70 | 203 |
| 396294 | 4 | 2-15-3 | 11218 | 11237 | CAGTCTTGTTTGTGCCTGCC | 79 | 203 |
| 396269 | 4 | 5-10-5 | 11244 | 11263 | TGTCCAGGACTCACCACAGA | 77 | 204 |
| 396346 | 4 | 2-15-3 | 11244 | 11263 | TGTCCAGGACTCACCACAGA | 83 | 204 |
| 396270 | 4 | 5-10-5 | 11801 | 11820 | TATGGCACCTTCTTAAATAT | 85 | 205 |
| 396347 | 4 | 2-15-3 | 11801 | 11820 | TATGGCACCTTCTTAAATAT | 81 | 205 |
| 396271 | 4 | 5-10-5 | 12248 | 12267 | TGCTTTTGGTATAGAAGAGT | 86 | 206 |
| 396348 | 4 | 2-15-3 | 12248 | 12267 | TGCTTTTGGTATAGAAGAGT | 76 | 206 |
| 396235 | 4 | 5-10-5 | 12526 | 12545 | AAATGTGGCTGGCAGATGTC | 79 | 207 |
| 396312 | 4 | 2-15-3 | 12526 | 12545 | AAATGTGGCTGGCAGATGTC | 82 | 207 |
| 396236 | 4 | 5-10-5 | 12572 | 12591 | GTCAGAGCTCATCTACATCA | 87 | 208 |
| 396313 | 4 | 2-15-3 | 12572 | 12591 | GTCAGAGCTCATCTACATCA | 82 | 208 |
| 396237 | 4 | 5-10-5 | 12754 | 12773 | CTGATAAAGACCAGCACCAA | 69 | 209 |
| 396314 | 4 | 2-15-3 | 12754 | 12773 | CTGATAAAGACCAGCACCAA | 70 | 209 |
| 396238 | 4 | 5-10-5 | 12762 | 12781 | AGGACTCACTGATAAAGACC | 69 | 210 |
| 396315 | 4 | 2-15-3 | 12762 | 12781 | AGGACTCACTGATAAAGACC | 43 | 210 |
| 396239 | 4 | 5-10-5 | 12982 | 13001 | CAGACTCTGAATCAGTTTTA | 78 | 211 |
| 396316 | 4 | 2-15-3 | 12982 | 13001 | CAGACTCTGAATCAGTTTTA | 70 | 211 |
| 396240 | 4 | 5-10-5 | 13021 | 13040 | CAGTCCCCAATTCTGCTGCC | 43 | 212 |
| 396317 | 4 | 2-15-3 | 13021 | 13040 | CAGTCCCCAATTCTGCTGCC | 70 | 212 |
| 396241 | 4 | 5-10-5 | 13107 | 13126 | CCAGTGTTAGGCTCTGCCAG | 76 | 213 |

TABLE 4-continued

Inhibition of human CD40 mRNA levels by chimeric oligonucleotides having 4-10-4 MOE wings and deoxy gap, 5-10-5 MOE wings and deoxy gap, and 2-15-3 MOE wings and deoxy gap

| Oligo ID | Target SEQ ID NO | Motif | Target Start Site | Target Stop Site | Sequence (5' to 3') | % Inhibition | SEQ ID NO |
|---|---|---|---|---|---|---|---|
| 396318 | 4 | 2-15-3 | 13107 | 13126 | CCAGTGTTAGGCTCTGCCAG | 85 | 213 |
| 396242 | 4 | 5-10-5 | 13134 | 13153 | GAATGCCAGGAAAGGAGTGA | 69 | 214 |
| 396319 | 4 | 2-15-3 | 13134 | 13153 | GAATGCCAGGAAAGGAGTGA | 84 | 214 |
| 396272 | 4 | 5-10-5 | 13171 | 13190 | CAGCCCCAAGGCCCAAAGAT | 48 | 215 |
| 396349 | 4 | 2-15-3 | 13171 | 13190 | CAGCCCCAAGGCCCAAAGAT | 57 | 215 |
| 396220 | 4 | 5-10-5 | 13491 | 13510 | CTGCACTGGAGCAGCAGTGT | 81 | 216 |
| 396297 | 4 | 2-15-3 | 13491 | 13510 | CTGCACTGGAGCAGCAGTGT | 74 | 216 |
| 396221 | 4 | 5-10-5 | 13517 | 13536 | ACCGGTTGGCATCCATGTAA | 61 | 217 |
| 396298 | 4 | 2-15-3 | 13517 | 13536 | ACCGGTTGGCATCCATGTAA | 73 | 217 |
| 396222 | 4 | 5-10-5 | 13525 | 13544 | CCTGGGTGACCGGTTGGCAT | 71 | 218 |
| 396299 | 4 | 2-15-3 | 13525 | 13544 | CCTGGGTGACCGGTTGGCAT | 82 | 218 |
| 396223 | 4 | 5-10-5 | 13802 | 13821 | CAAGTTGGGAGACTGGATGG | 65 | 219 |
| 396300 | 4 | 2-15-3 | 13802 | 13821 | CAAGTTGGGAGACTGGATGG | 79 | 219 |
| 396224 | 4 | 5-10-5 | 13810 | 13829 | CTTTAATACAAGTTGGGAGA | 68 | 220 |
| 396301 | 4 | 2-15-3 | 13810 | 13829 | CTTTAATACAAGTTGGGAGA | 64 | 220 |
| 396225 | 4 | 5-10-5 | 13877 | 13896 | TCGGAAGGTCTGGTGGATAT | 65 | 221 |
| 396302 | 4 | 2-15-3 | 13877 | 13896 | TCGGAAGGTCTGGTGGATAT | 83 | 221 |
| 396226 | 4 | 5-10-5 | 13896 | 13915 | TGGGCACCAAACTGCTGGAT | 70 | 222 |
| 396303 | 4 | 2-15-3 | 13896 | 13915 | TGGGCACCAAACTGCTGGAT | 76 | 222 |
| 396227 | 4 | 5-10-5 | 13937 | 13956 | TATGGCTTCCTGGGCGCAGG | 59 | 223 |
| 396304 | 4 | 2-15-3 | 13937 | 13956 | TATGGCTTCCTGGGCGCAGG | 74 | 223 |
| 396228 | 4 | 5-10-5 | 13961 | 13980 | AATGCTGCAATGGGCATCTG | 78 | 224 |
| 396305 | 4 | 2-15-3 | 13961 | 13980 | AATGCTGCAATGGGCATCTG | 83 | 224 |
| 396229 | 4 | 5-10-5 | 13977 | 13996 | GTTCACTATCACAAACAATG | 84 | 225 |
| 396306 | 4 | 2-15-3 | 13977 | 13996 | GTTCACTATCACAAACAATG | 67 | 225 |
| 396230 | 4 | 5-10-5 | 13997 | 14016 | CAGTTAAGCAGCTTCCAGTT | 84 | 226 |
| 396307 | 4 | 2-15-3 | 13997 | 14016 | CAGTTAAGCAGCTTCCAGTT | 85 | 226 |
| 396231 | 4 | 5-10-5 | 14028 | 14047 | AATTTTATTTAGCCAGTCTC | 80 | 227 |
| 396308 | 4 | 2-15-3 | 14028 | 14047 | AATTTTATTTAGCCAGTCTC | 79 | 227 |
| 396232 | 4 | 5-10-5 | 14046 | 14065 | GTTGTATAAATATATTCTAA | 44 | 228 |
| 396309 | 4 | 2-15-3 | 14046 | 14065 | GTTGTATAAATATATTCTAA | 25 | 228 |
| 396233 | 4 | 5-10-5 | 14065 | 14084 | ACAGTGTTTTGAGATTCTG | 83 | 229 |
| 396310 | 4 | 2-15-3 | 14065 | 14084 | ACAGTGTTTTGAGATTCTG | 50 | 229 |
| 396273 | 4 | 5-10-5 | 14725 | 14744 | CTCAGGACCCAGAGTGAGGA | 37 | 230 |
| 396350 | 4 | 2-15-3 | 14725 | 14744 | CTCAGGACCCAGAGTGAGGA | 50 | 230 |
| 396274 | 4 | 5-10-5 | 15073 | 15092 | TGGGTTAAACCTCACCTCGA | 59 | 231 |

TABLE 4-continued

Inhibition of human CD40 mRNA levels by chimeric oligonucleotides having 4-10-4 MOE wings and deoxy gap, 5-10-5 MOE wings and deoxy gap, and 2-15-3 MOE wings and deoxy gap

| Oligo ID | Target SEQ ID NO | Motif | Target Start Site | Target Stop Site | Sequence (5' to 3') | % Inhibition | SEQ ID NO |
|---|---|---|---|---|---|---|---|
| 396351 | 4 | 2-15-3 | 15073 | 15092 | TGGGTTAAACCTCACCTCGA | 56 | 231 |
| 396275 | 4 | 5-10-5 | 15350 | 15369 | ATTAGGTCCCAAAGTTCCCC | 23 | 232 |
| 396352 | 4 | 2-15-3 | 15350 | 15369 | ATTAGGTCCCAAAGTTCCCC | 48 | 232 |
| 396234 | 1 | 5-10-5 | 42 | 61 | GGCAGACGAACCATGGCGAG | 86 | 233 |
| 396311 | 1 | 2-15-3 | 42 | 61 | GGCAGACGAACCATGGCGAG | 82 | 233 |
| 396213 | 1 | 5-10-5 | 435 | 454 | GTAGCAATCTGCTTGACCCC | 82 | 234 |
| 396290 | 1 | 2-15-3 | 435 | 454 | GTAGCAATCTGCTTGACCCC | 79 | 234 |
| 396218 | 1 | 5-10-5 | 590 | 609 | GACCACAGACAACATCAGTC | 89 | 235 |
| 396295 | 1 | 2-15-3 | 590 | 609 | GACCACAGACAACATCAGTC | 85 | 235 |
| 396219 | 1 | 5-10-5 | 683 | 702 | CCACCTTTTTGATAAAGACC | 65 | 236 |
| 396296 | 1 | 2-15-3 | 683 | 702 | CCACCTTTTTGATAAAGACC | 41 | 236 |

Example 5

Antisense Inhibition of Human CD40 in HuVEC Cells, Primer Probe Set LTS37

Several antisense oligonucleotides exhibiting in vitro inhibition of CD40 (see Example 4) were tested at various doses in HuVEC cells. Cells were plated at densities of 5000 cells per well and treated with nM concentrations of antisense oligonucleotide as indicated in Table 5. After a treatment period of approximately 24 hours, RNA was isolated from the cells and CD40 mRNA levels were measured by quantitative real-time PCR, as described herein. Human CD40 primer probe set LTS37 was used to measure mRNA levels. CD40 mRNA levels were adjusted according to total RNA content as measured by RIBOGREEN®. Results are presented as percent inhibition of CD40, relative to untreated control cells. As illustrated in Table 5, CD40 mRNA levels were reduced in a dose-dependent manner.

TABLE 5

Antisense Inhibition of human CD40 in HuVEC cells, Primer Probe Set LTS37

| ISIS No | 0.2344 nM | 0.4688 nM | 0.9375 nM | 1.875 nM | 3.75 nM | 7.5 nM | 15.0 nM | 30.0 nM |
|---|---|---|---|---|---|---|---|---|
| 26163 | 17 | 35 | 38 | 51 | 62 | 67 | 82 | 89 |
| 396236 | 23 | 49 | 59 | 77 | 86 | 92 | 91 | 89 |
| 396266 | 35 | 45 | 58 | 74 | 55 | 72 | 57 | 56 |
| 396307 | 21 | 45 | 43 | 56 | 80 | 79 | 82 | 82 |
| 396218 | 34 | 47 | 52 | 57 | 78 | 82 | 86 | 86 |
| 396279 | 34 | 54 | 59 | 49 | 72 | 82 | 88 | 87 |
| 396287 | 31 | 48 | 52 | 50 | 64 | 77 | 85 | 86 |
| 396264 | 39 | 34 | 49 | 56 | 71 | 84 | 88 | 86 |

Example 6

Antisense Inhibition of Human CD40 in AGS Cells

Antisense oligonucleotides exhibiting in vitro inhibition of CD40 (see Example 4) were tested at various doses in AGS cells (human adenocarcinoma cells). Antisense oligonucleotides of SEQ ID No. 90 and SEQ ID No. 208 were designed as 4-10-4 gapmers or 5-10-5 gapmers, respectively, where the gap segment comprises 2'-deoxynucleotides and each wing segment comprises 2'-MOE or 2'OMe nucleotides. The antisense oligonucleotides comprise phosphorothioate backbones (internucleoside linkages) and 5-methylcytosine substitutions throughout.

Cells were plated at densities of 5000 cells per well and treated with nM concentrations of antisense oligonucleotide as indicated in Table 6. After a treatment period of approximately 24 hours, RNA was isolated from the cells and relative CD40 mRNA expression levels were quantified by real time RT-PCR using the QuantiTect™ SYBR® Green RT-PCR kit (Qiagen). CD40 mRNA levels were adjusted according to GAPDH content, a housekeeping gene. Results are presented as percent inhibition of CD40, relative to cells treated with a scrambled control oligonucleotide (TCCATTTATTAGTCTAGGAA (5-10-5 gapmer, where the gap segment comprises 2'-deoxynucleotides and each wing segment comprises 2'-MOE nucleotides. The oligonucleotide comprises phosphorothioate backbones (internucleoside linkages) and 5-methylcytosine substitutions throughout.

TABLE 6

Antisense Inhibition of human CD40 in AGS cells

| ISIS No | Motif | Wing segment | 12.5 nM | 25.0 nM | 50.0 nM | Seq ID |
|---|---|---|---|---|---|---|
| 26163 | 4-10-4 | 2'MOE | 80 | 69 | 90 | 90 |
| 396236 | 5-10-5 | 2'MOE | 83 | 86 | 94 | 208 |
| — | 4-10-4 | 2'OMe | 51 | 54 | 66 | 90 |
| — | 5-10-5 | 2'OMe | 60 | 63 | 69 | 208 |

As illustrated in Table 6, CD40 mRNA levels were reduced in a dose-dependent manner. Antisense oligonucleotides comprising 2'MOE wing segments are more active than those with 2'OMe wing segments.

Example 7

Antisense Inhibition of Murine CD40 In Vitro

Chimeric antisense oligonucleotides having 5-10-5 MOE wings and deoxy gap and 4-10-4 MOE wings and deoxy gap may be designed to target murine CD40. These antisense oligonucleotides can be evaluated for their ability to reduce CD40 mRNA in primary mouse hepatocytes using similar methods as described in the human in vitro study.

For example, primary mouse hepatocytes may be treated with 0.2344 nM, 0.4688 nM, 0.9375 nM, 1.875 nM, 3.75 nM, 7.5 nM, 15.0 nM, and 30.0 nM of antisense oligonucleotides for a period of approximately 24 hours. RNA can be isolated from the cells and CD40 mRNA levels can be measured by quantitative real-time PCR, as described herein. Murine CD40 primer probe sets can be used to measure mRNA levels. CD40 mRNA levels can then be adjusted according to total RNA content as measured by RIBOGREEN®.

Example 8

Antisense Inhibition of Murine CD40 In Vivo

Antisense oligonucleotides showing statistically significant dose-dependent inhibition from an in vitro study can be evaluated for their ability to reduce CD40 mRNA in vivo.
Treatment Antisense oligonucleotide can be evaluated in Balb/c mice and compared to a control group treated with saline. Oligonucleotide or saline would be administered subcutaneously at a dose of 5 mg/kg, 10 mg/kg, 25 mg/kg, or 50 mg/kg twice a week for three weeks. After the treatment period, whole liver can be collected for RNA analysis and protein analysis.
RNA Analysis Liver RNA can be isolated for real-time PCR analysis of CD40. It is theorized that an antisense oligonucleotide showing significant dose-dependent inhibition in vitro may show significant dose-dependent inhibition in vivo.

Protein Analysis

Liver CD40 protein may be measured by Western blot.

Example 9

Tolerability of Antisense Compounds in Rodents

Male 6 week old Balb/c mice were dosed subcutaneous 2× per week for 4 weeks with 25 or 50 mg/kg of antisense oligonucleotides Isis 26163 or Isis 396236. Mice were sacrificed 2 days following last administration. Body weights of the animals were monitored throughout the study. After sacrification liver, spleen and kidney weights and liver enzymes ALT and AST from mouse plasma were determined.

Compared to a saline control treatment body weights of the mice are not affected by antisense oligonucleotides Isis 26163 or Isis 396236. Liver weight and spleen weight displayed a slight increase for Isis 26163 but not for Isis 396236. LFT (liver function test) elevations were small and within the normal range of high dose mouse studies.

Example 10

Antisense Inhibition of Human CD40 In Vitro on T24 Cells—Comparative Data for ISIS 26163 and ISIS19216

Antisense oligonucleotides ISIS 26163 and ISIS19216 targeted to a CD40 nucleic acid were tested for their effects on CD40 mRNA in vitro. The antisense oligonucleotides were designed as 4-10-4 gapmers, where the gap segment comprises 2'-deoxynucleotides and each wing segment comprises 2'-MOE nucleotides. The antisense oligonucleotides comprise phosphorothioate backbones (internucleoside linkages) and 5-methylcytosine substitutions throughout or in the wings, respectively.

T24 cells at a density of 7000 cells per well in a 96-well plate were treated with 100 nM or 150 nM, respectively, of antisense oligonucleotide. After a treatment period of approximately 24 hours, RNA was isolated from the cells and CD40 mRNA levels were measured by quantitative real-time PCR, as described herein. CD40 mRNA levels were adjusted according to GAPDH content, a housekeeping gene.

Results are presented in Table 7 as percent inhibition of CD40, relative to untreated control cells.

TABLE 7

| Oligo ID | Target site | nM on T24 cells | % Inhibition | SEQ ID No. |
|---|---|---|---|---|
| 26163 | 70-87 | 100 | 98 | 90 |
| 19216 | 73-90 | 150 | 66 | 10 |

Sequence ISIS 26163 shows a superior activity over ISIS19216, which overlaps the sequence by 15 nucleobases.

The invention claimed is:

1. A modified antisense compound 12 to 30 nucleobases in length and having a nucleobase sequence that is at least 90% complementary to an equal length portion of the human CD40 gene but not to other sequences throughout the human genome, selected from the following regions of SEQ ID NO: 4:
   (a) positions 11250-12685, corresponding to intron 6;
   (b) positions 2943-6367, corresponding to intron 1;
   (c) positions 6447-6780, corresponding to intron 2;
   (d) positions 6907-7157, corresponding to intron 3;
   (e) positions 7305-7673, corresponding to intron 4;
   (f) positions 7768-11187, corresponding to intron 5;
   (g) positions 12773-12877, corresponding to intron 7;
   (h) positions 12907-13429, corresponding to intron 8; and
   (i) positions 13662-16001, which forms part of exon 9 or a region 3' to exon 9.

2. The antisense compound of claim 1, wherein the nucleobase sequence is at least 90% complementary to an equal length portion of positions 12527-12685 of SEQ ID NO: 4.

3. The antisense compound of claim 2, having a nucleobase sequence comprising at least 8 contiguous nucleobases of the nucleobase sequence of SEQ ID NO: 208, wherein the nucleobase sequence of the compound is at least 95% complementary to the sequence shown in SEQ ID NO: 4.

4. A modified antisense compound 20 nucleobases in length and consisting of the nucleobase sequence of SEQ ID NO: 208.

5. The antisense compound of claim 1, wherein said antisense compound is an antisense oligonucleotide.

6. The antisense compound of claim 5, wherein at least one internucleoside linkage is a modified internucleoside linkage.

7. The antisense compound of claim 6, wherein each internucleoside linkage is a phosphorothioate internucleoside linkage.

8. The antisense compound of claim 5, wherein at least one nucleoside comprises a modified sugar.

9. The antisense compound of claim 8, wherein at least one modified sugar is a bicyclic sugar.

10. The antisense compound of claim 9, wherein the at least one bicyclic sugar comprises a 4'-CH(CH$_3$)—O-2' bridge.

11. The antisense compound of claim 8, wherein at least one modified sugar comprises a 2'-O-methoxyethyl.

12. The antisense compound of claim 1, wherein at least one said nucleobase is a modified nucleobase.

13. The antisense compound of claim 12, wherein the modified nucleobase is a 5-methylcytosine.

14. The antisense compound of claim 1, wherein the compound is an oligonucleotide comprising:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

15. The antisense compound of claim 14, wherein the oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar;
   and wherein each internucleoside linkage of said antisense compound is a phosphorothioate linkage.

16. The antisense compound of claim 14, wherein the oligonucleotide comprises:
   a gap segment consisting of fifteen linked deoxynucleosides;
   a 5' wing segment consisting of two linked nucleosides;
   a 3' wing segment consisting of three linked nucleosides;
   wherein the gap segment is positioned between the 5' wing segment and the 3' wing segment, wherein each nucleoside of each wing segment comprises a 2'-O-methoxyethyl sugar;
   and wherein each internucleoside linkage of said antisense compound is a phosphorothioate linkage.

17. The antisense compound of claim 15 or 16, wherein every cytosine is a 5-methylcytosine.

18. An antisense oligonucleotide 20 nucleobases in length having the sequence of nucleobases as set forth in SEQ ID NO:208, wherein each cytosine is a 5-methylcytosine, each internucleoside linkage is a phosphorothioate linkage, nucleotides 1-5 and 16-20 are 2'-O-methoxyethyl nucleotides, and nucleotides 6-15 are 2'-deoxynucleotides.

19. A composition comprising an antisense compound of claim 1 or 18 or a salt thereof and a pharmaceutically acceptable carrier or diluent.

20. A method comprising administering to an animal an antisense compound of claim 1 or an oligonucleotide of claim 18.

* * * * *

SEQUENCE LISTING

<160> NUMBER OF SEQ ID NOS: 238

<210> SEQ ID NO 1
<211> LENGTH: 1004
<212> TYPE: DNA
<213> ORGANISM: H. sapiens

<400> SEQUENCE: 1

```
gcctcgctcg ggcgcccagt ggtcctgccg cctggtctca cctcgccatg gttcgtctgc    60
ctctgcagtg cgtcctctgg ggctgcttgc tgaccgctgt ccatccagaa ccacccactg   120
catgcagaga aaaacagtac ctaataaaca gtcagtgctg ttctttgtgc cagccaggac   180
agaaactggt gagtgactgc acagagttca ctgaaacgga atgccttcct tgcggtgaaa   240
gcgaattcct agacacctgg aacagagaga cacactgcca ccagcacaaa tactgcgacc   300
ccaacctagg gcttcgggtc cagcagaagg gcacctcaga aacagacacc atctgcacct   360
gtgaagaagg ctggcactgt acgagtgagg cctgtgagag ctgtgtcctg caccgctcat   420
gctcgcccgg ctttgggtc aagcagattg ctacaggggg ttctgatacc atctgcgagc   480
cctgcccagt cggcttcttc tccaatgtgt catctgcttt cgaaaaatgt caccctgga   540 caagctgtga gaccaaagac ctggttgtgc aacaggcagg cacaaacaag actgatgttg   600
tctgtggtcc ccaggatcgg ctgagagccc tggtggtgat ccccatcatc ttcgggatcc   660
tgtttgccat cctcttggtg ctggtcttta tcaaaaaggt ggccaagaag ccaaccaata   720
aggcccccca ccccaagcag gaaccccagg agatcaattt tcccgacgat cttcctggct   780
ccaacactgc tgctccagtg caggagactt tacatggatg ccaaccggtc acccaggagg   840
atggcaaaga gagtcgcatc tcagtgcagg agagacagtg aggctgcacc cacccaggag   900
tgtggccacg tgggcaaaca ggcagttggc cagagagcct ggtgctgctg ctgcaggggt   960
gcaggcagaa gcggggagct atgcccagtc agtgccagcc cctc                   1004

<210> SEQ ID NO 2
<211> LENGTH: 427
<212> TYPE: DNA
<213> ORGANISM: H. sapeins
<220> FEATURE:
<221> NAME/KEY: misc_feature
<222> LOCATION: 13, 52, 152, 193, 245, 254, 263, 298, 305, 323, 331,
      344, 374
<223> OTHER INFORMATION: n = A,T,C or G

<400> SEQUENCE: 2
gataccatct gcnagccctg cccagtcggc ttcttctcca atgtgtcatc tnctttcgaa    60
aaatgtcacc cttggacaag ctgtgagacc aaagacctgg ttgtgcaaca ggcaggcaca   120
aacaagactg atgttgtctg tggtccccag gntcggctga gagccctggt ggtgatcccc   180
atcatcttcg ggntcctgtt tgccatcctc ttggtgctgg tctttatcaa aaaggtggcc   240
aagangccaa ccantaaggc ccnccacccc aagcaggaac cccaggagat caattttncc   300
gacgntcttc ctggctccaa cantgctgct ncagtgcagg aganttttaca tggatgccaa   360 ccggtcaccc aggnaggatg ggcaaagaga gtcgcatttc agttgcaggg agagacagtg   420
aaggttg                                                            427

<210> SEQ ID NO 3
<211> LENGTH: 871
<212> TYPE: DNA
<213> ORGANISM: H. sapiens

<400> SEQUENCE: 3
acctcgccat ggttcgtctg cctctgcagt gcgtcctctg gggctgcttg ctgaccgctg    60
tccatccaga accacccact gcatgcagag aaaaacagta cctaataaac agtcagtgct   120
gttctttgtg ccagccagga cagaaactgg tgagtgactg cacagagttc actgaaacgg   180
aatgccttcc ttgcggtgaa agcgaattcc tagacacctg gaacagagag acacactgcc   240
```

```
accagcacaa atactgcgac cccaacctag ggcttcgggt ccagcagaag ggcacctcag      300
aaacagacac catctgcacc tgtgaagaag gctggcactg tacgagtgag gcctgtgaga      360
gctgtgtcct gcaccgctca tgctcgcccg gctttggtgt caagcagatt gctacagggg      420
tttctgatac catctgcgag ccctgcccag tcggcttctt ctccaatgtg tcatctgctt      480
tcgaaaaatg tcacccttgg acaaggtccc aggatcggct gagagcctgt ggtgatccca      540
tcatcttcgg atctgtttgc atctcttggt gctgtcttat caaaaagtgg caagaactac      600
ccataggccc ccacccagca gacccagaga taatttctga gatttctgct caaatgtgtc      660
agtagggagt catgagcaca gtcccacggt ggagaaccgc tctttggaga attgtgccca      720
gattgccatg aaaaggatgt caagataggt gggttttgtg gggggtaaac cttccccttt      780
tgagctgtga atttgaact ctcggccttt aagaatgggg ggttaaccaa tttgactcca      840
acagttaaac ttgattatga ggtttgcctt t                                    871

<210> SEQ ID NO 4
<211> LENGTH: 16001
<212> TYPE: DNA
<213> ORGANISM: H. sapiens

<400> SEQUENCE: 4
cagcttgagg tctgtgttga gattaccagc ttcgcacccc ctgccaccaa ctctttgtca       60
tgattggagg ctgtacttag gatgagaagt tgctgaaccc actcattcat ttattcattc      120
attcagcacc catatattgg tgtcctatta tgtacctagg actgggatag atccagtcct      180
gccctcaggg agctcacagt caaatgggac caggcagaag gagttatgag ctggcatgct      240
aaatgctgtg gcaacacagg ggaggaggca ggtgggata gagtacctac ctctgcctca      300
gggagttggg gaaggtgtaa gaggaggcaa catttaaact gtttaagaaa ggagaaggaa      360
aggaaggaaa catcaagagc aatgagataa accgtaagga aaaagattg tgtgcctggg       420 aagtggggag aggctgaagc cagtgtgcat gggaggacgt ggcaggaagt aagcatagaa      480
agagaggttg gggctgagtg aggaagggtg tgctttgcca ggataagaaa tttggatcat      540
cctgagggtg cagggaaacc caaagaggct tttatgcagg aaagtgtccc agtcgatcag      600
atctggagtt tatcaagaga atcgcagcag tgtaaagagt tgcctggcac atagtaggtg      660
ctcaataaat cctgtggaat gagagaggct gttgggacag tccagatgaa agatggcacc      720
ctctgaatta gggcagtggc agaggtgaca gaaaataagg gatggatcct agaggcagaa      780
tccacaagac ttgcaaatgt gcccttaaca gcagaagcca tgagaatggg gttagaagtg      840
tcctcctctt ccatcctccc tgatctgtga ggtctggcct cttgtcctct tccagaaatt      900
gagagcttgg agggtcatca cctcaaccgt tgtctagttc aagctcctaa gttttccttg      960
gagaaaaatt taggcctaag ggaacacagt ccttcagagg cagaggctgc accagaaccc     1020
aggtgttcca tgctgcaaag cagagtgtta acactggttc aagaacatct tgagggccag     1080
gtgcggtggc tcatgcctgt aatctcagca ctttgggagg ccaaggcagg cggatcacct     1140
gaggtcagga gtttgagacc agcctggcca acgtggagaa accccgtctc tactaaaaat     1200
acaaaaatta gctgggcgtg gtggcgccag cctgtaatcc cagctactcg ggaggctgag     1260
gcaggagaat tgcttgaacc caggaggcag aggttgcagt gagccgagat catgccactg     1320
cactccagcc tggcaacag aatgagactc tgtcaaaaaa aacccaaaaa ccaaaaacca     1380
aacaaacacc caaaaaacaa aacgaaacaa aaaacaaaaa aacaaaagca cgtcttcaga     1440
```

```
gttcatgaac ccaggaaatg taggcacaag tgtgtgtgtt tctgcaaaat gagagggtcc   1500
cgagtttcct aacatactta aagtgtttta tgatgccaca aaaggctggc ccactctttt   1560 ttttttttg  agatggagtt ttgcactgtc gcccaggctg aagtgcagtg atgtaatcat   1620
tgcaatcatg gctcactgca accttgactt cttgagctca agcgatcctc ctgcctcagc   1680
ctcctgagta gctgggacta caggtgtttg ccaccatgcc tggctaactt aaaaatttct   1740 ttatttgta  gagatggggg tcttgccatg ttgccaggct ggtcttgaac tcctggcctc   1800
aagcaatctc cctttttggc cttccaaagt gttagattac aggcgtaagc caccgcgcct   1860
ggcccccacc tttatttta  tttttattta ttatttattt tttttttttt tgagactgag   1920
tcttgctctg ccttcgaggc tggagtgcag tggcacgatc tcggctcatt gcaatctctg   1980
cctctgcggt tcaagcgatt ctcctgcctc agcctcccga gtagctggga ttacaggcga   2040
acgccactac atccggttaa tttttgtatt tttagtagag acggagtttc actatgttgg   2100
ccaggttggt ctcgaactcc tgacctcaag tgatctgccc gcctcggcct cctaaagtgc   2160
tggattacag gcgtgagcca ccgcgcccgg ccccactctt aataaatgcc tgtctccagg   2220
tgctgggtgg gaggtgggat ggaatggaat gaggtgagga cgcatggatg catggatgaa   2280
tggatgggaa gttgagacga cgcgcccaca cgagggaatt cctttgaaa  gagagcgaaa   2340 ttctgagttg ggaaactctt ccttgaaacg cctccccata ccccagctgt ggccttcccg   2400
ttttctgcgt ggtggtgtgg ggggaacttc ctcaggcctc tccgcagtgg agcctctttc   2460
ggttctgcca ggatacctag aggcagcgga gagcggggca gggaggggaa accgtgagg    2520 gtccctgtgg caggccccag cacccatggg atctctctcc ggtcgcagga agcaggctag   2580
ctcctagccc gctcggctt  ggcctttgtg ggacctgggg gcaaagaaga agagctgtct   2640
ctgggaccat gcctcctccc gtacacagca agatgcgtcc ctaaactccc gggggaatta   2700
gacttgtggg aatgttctgg ggaaactcct gcgcggtgaa ttgctggggg ctccgccccc   2760
ccgataggtg gaccgcgatt ggtctttgaa gaccccgccc cttcctggg  cggggccaag   2820 gctggggcag gggagtcagc agaggcctcg ctcgggcgcc cagtggtcct gccgcctggt   2880
ctcacctcgc tatggttcgt ctgcctctgc agtgcgtcct ctgggctgc  ttgctgaccg   2940 ctgtgagttg ttttgcccc  gaccagacgg gagttgggag tggggaatga aaggaaagg    3000 gaaggaagac ttcggggaag aggccttcct ggctgatttt tgtgggggca ggagggtggg   3060
tgggagctgg gcaaggtgcc cccgctcctg gctgaatggg gtgggctgcc tctctcttct   3120
cccgggctgg ggtcccggga gcggcctaca ggggccgctc agggaaggca ctggctgccc   3180
aagcgtgcct agacggcctg gacgggttta gggagcctca gaggctggcc acacagagac   3240
tggtaggggg ttcagagggc gggaagtgag gcggaccaag ggaaggggcg ggtctggccc   3300
gtttcctgtc cccttcttat tgtggacaga tgccagcctc tgtaagtagt tatcatctcc   3360
ttgccagctg gggctgcctt cttccagggc atcttgtggg aacaagagat gggtgcagag   3420
gcccaggtac ttttgtgaga aggcaaggag cttttaacat cgccttccac cccgaaccgt   3480
atcttgggtg ttccaaccta ggaggaatcc ccagggcttt gccttttct  cctgaattta   3540 agatgacata ggagaccct  ggggagatga acagtttatg ggacacaata aagggttagg   3600
agaccagagt tctggttggc tctgacaggg ctggtgatca gagggctgga gaaaccaggg   3660
gtttctccag gcaccagagg ggctcagagc caaccaagca tatctccggg attttcagaa   3720
gcctacactt gactcacttt ttgtttaaat gtattttgt  agttcctcat tctgaggct    3780 gggaatcccc caagtacctg gctccttcat cccagcccct ctggcctccc cctactttag   3840
```

```
agggctgtag attcctgcct gaagcctggg caggaatgac ccatggtatc aaggaaagca    3900
agggaagcag caagggaaga gagggagtgg ggaggctgct ttggtcccac agctttcact    3960
ttcacctgaa gcaatggctc ttagggaaca gggaggcagg gggagggcgg agctggaaag    4020
aggtaaaggg gggcccttgt ggtaggagtg agaaagagc cagaggaggt ggggtgaagg     4080
gtgtgatcca ggcttctcaa gagcagagtt tgccctcata actcccaact ttggctccag    4140
gtagaggctg ggctgtgaca acaatgtcag aagctatcta ttgagggctt cttgtgtgtc    4200
aggctctgag ccaaacactg cctgttttct ttgtctgatt tctcacaact cccccattat    4260
acagatgggc aaattgaggc tcagaaaggg ggattgtctt gccaaaggtc tcatagctag    4320
ctaatggaag aacctggttg tgaatctaca tctgcatgat tcccgagcct gcctctcaga    4380
tagtgagagt ctccaagctc tggtcctgag ctgttttgtg cagaaggac cagaactatg     4440 gggagtgaga actggagatt gacagacttt taggggagcg ttttatttct catgtgtttg    4500
aagatggtat caaggacttt cctatctttg ggagtgtggg agctccacgt tcacaggatg    4560
gtgtcttgca atgagctggt gggggcagt agccttttct acttcctttc ccattttggg     4620
taagacacat ttctgtaagt aatttgctga gatacccagg ttgaatgaga gccaccagtt    4680
aggtaggatt ctgacagcc agccaggtag ccgggctgct tgccatatat catgcaagca     4740
gaaacaaatg aatgatgatt aaaattgcca tttaatgagc acctactatg ttcctgacac    4800
tgtgctaggc catatacatg tattctttct tatcttcgta atccaacctg cagggcaggc    4860
attattactc ccatttaga gatagagaaa ctgaggctaa gagaagcaaa ataactagta     4920
agtgttacaa agtcaggact ggagtctaaa gctgtctgac tctcaaactt gtgttctttt    4980
cactggctgt tcccaaactg tgggacagtt ttaaggagca catggacata gaattaaaca    5040
tacacttact ttacagttct tttaaaaatc cttctcattt tttcaaagag gaagtctctg    5100
gagctagaat agagttaatg cctctcaaag gcttgctaat ccttcttta aaacaaaaat     5160 caagagcagg cctgggaggg ccttcaacaa gcaaacaacc agctgggttt taataacctt    5220
gttttgtttc cccagaattt atttttaggg ttaccttta tttatgagaa gtgatactgg     5280
ttcttgtctc ttggcaatga tgtgaggttt acatttaaag taaatgtacc ggccaggcac    5340
ggtggcttgt gcctgtaatc ccagcacttt gggaggccaa ggcagtcaga tcacttgagg    5400
tcaggagttt tagatcagcc tggccaacat ggtgaaaccc tgtctctact aaaaatacat    5460
aaattagccg gcatagtgg tacacacctg taatcccagc tactcaggag gctgaggctg     5520
gagaattgct tgaacccagg agatagaggt tgcagtgggc tgagatgatg ccactgcact    5580
ccagcctggg cgatggagcg agactctgtc tcaaaaaata aaataaaagt attgaaatta    5640
acaataagta attaatagca tgggtggtac ctggatgtag taaatggtg aagatgaaac     5700 acaagttgat ggagagagga gcattgagac ctgagttctc atttggactc tgtcactgtg    5760
agactctggg caagtgaccc tcctctttgg tgctcagtct caactatctg taaaatgaaa    5820
gtgtgagttt acccttccag ctttacattc tagcatttta tgagggaagg gctggatgaa    5880
cagatgatga ggagttggag gaagaaaaca tgatgggctt tggaaaggag caggaaggga    5940
agcagaagaa taggaggaag aggccaagtg ctaaacatag ccccaaacag cactgggacc    6000
agctgaagtc agccagcttc aggactccag gggagctgct ggagtcccca tatcctatgg    6060
gatctttggg aagaggaatg actcaggcat caagccccaa ggaattctgt tctgttcaga    6120
gaatattgtg agtttacagt accattgctt tgtaaaaata ccagaatgat tctctgggtg    6180
```

```
cgattataat cagctcagtt gacaatttac ttgaaaacaa acatgccaaa tatcatgcag    6240
gttccacttt ctgttttgac ttgcacttca gtttgcagcc tctgtcctgg atgactttta    6300
cctttctgct gaagaagttg caacggagat ttcaagatcc cttcaaattg cacaattctg    6360
tttttaggtc catccagaac cacccactgc atgcagagaa aaacagtacc taataaacag    6420
tcagtgctgt tctttgtgcc agccaggtga gatgccaacc tctagcccca tcatggagt     6480 cccccttttgc tttggtggca gacgcagacc ccatatgtta actgtaaaact caaatctgaa   6540 acgacccatt tcccagccct gcttcactgt cagaatgttc tggttccctc tctaccaggt    6600
aaaactctgt ctaccctgaa ctagggatcc cagcttctcc atcttcctcg cctgattatg    6660
aaggatccaa gactttcatc tttgaatccc ctaccctaaa gcctggcctg atcattgtgt    6720
ggttagtgtc tgactcatgg agttggccag agccctccct catttcctga tgttttccag    6780
gacagaaact ggtgagtgac tgcacagagt tcactgaaac ggaatgcctt ccttgcggtg    6840
aaagcgaatt cctagacacc tggaacagag agacacactg ccaccagcac aaatactgcg    6900
accccagtgc gtgcgctgtt gggaaaggga cgcttgggaa ccgggctgat attcccgaca    6960
atgcagccat tctaatttta tgtagccagg gtctgctctg attggttgga gtccgggctg    7020
tactgatcat taaatgattt gattgccatc tctacttgga agagggtctg aggaagaaag    7080
agcaggcaat gtgggagtg aggctcagag catggcccag caggggttc ccatccttcc      7140 tgcccttctc ttctcagacc tagggcttcg ggtccagcag aagggcacct cagaaacaga    7200
caccatctgc acctgtgaag aaggctggca ctgtacgagt gaggcctgtg agagctgtgt    7260
cctgcaccgc tcatgctcgc ccggcttgg ggtcaagcag attggtaagt ggctcatctg      7320
ggaatcagtt ttggagggg acagaggagc ttagggccca aggtgagggg ctgggcagtg     7380
ggcacttagc cccagaggca gaggaagcag aggctccaac ctatgtcggt atccccactg    7440
gagtgagctg cagacgggac cttgttcatt ctgccttctg ccatggggat ctgcctttga    7500
agggcaatgg gagaagtcct cctggggact gcagctgtcg ggggcagtac cacatcgggg    7560
gaagagtgct caaggcagga gctcttcccg tcctgcctgg ccactggctg ccttgtgagc    7620
cggacaggtg gtccactgtg atggttaatg tcccccctccc cacccactcc cagctacagg    7680
ggtttctgat accatctgcg agccctgccc agtcggcttc ttctccaatg tgtcatctgc    7740
tttcgaaaaa tgtcacccctt ggacaaggta taagcactca tcccttgtgt ttcctgctct    7800
aagagtggca tggagctgcc tccattctct ccagccacct gtcctgtccc tgctcccaga    7860
ggtccacaca cactcatgta cttgtgaagc atctgcagag tggcctcatg gccaaccaga    7920
caggcacatt tccacatttt ttttgcctgc tgtctctttg aggtaataga cactgttgat    7980
ctctcgcttc atgagagcct cctatcttgg gggtattggg acacttattt tagcttttcct   8040 tctgcccctc ctgcttctcc tcagttttcc tcgtcttgct ttcaccttac ctggctttct    8100
agggctttct gggctctggg tgctcaccct gagggcctcc ctctcttacc tccaactcca    8160
aacccacacc aggtcctgcc actggctgtc tacgtgtttt gggaacttac tgtctccact    8220
gttgtcactt tagtttgggc ctcatcactg tggtctgggt gatgcctttt ctgcctcctg    8280
gcctccctgc ctctgtctct cccctcctgc tggttctgtc tccatcctct tgccaacatg    8340
agcgttcgac agtttctttc aaatcatgac actctcctat ttgagatgct tcctgtctct    8400
ctgttggaac taagactcct tagcatggca cccaaccttc ctgttgcatt tcctgctctc    8460
tttcctgcat cgcatagctt catgctactt gcaatcctct gaacacactg ttcattctct    8520
tccatcaaac tcatctgcct ggaataccctt aaacatgggc cccaggccag gcgcggtggc    8580
```

```
tcttgcctgt aatctcagca ctttggatgc caaggcgggt ggatcacttg aggtcaggag    8640
ttcaagacca gccagcacaa catggtaaaa acccatctct actaaaaata ccaaaaaatt    8700
agctgggtgt ggtggtgggc gcctgtaatc ccagctcctc gggaggctga ggcaggagaa    8760
tcacttgaac ccggaaggtg gagtttgcag tgagccaaga tagcgccact gcactccagc    8820
ctgggcaaca gagcgacatt ctgtctcaaa aaacaaacac ctgccccatt aacttttgc     8880 atttgatttt taaaaatggg caagataggc acatgggaca gaaggcacaa aagagccaaa    8940
gtgatgtctt tctcccatcc ctgccccta ggctcccagt tctttctgga gggagccatt     9000
gttccttgca tatccttcca gagattctac atataaacaa accaacacac acacacacac    9060
acacaaacac acacaaaatt tccctccttt tacttttgca caaataggag tatacatttt    9120
atttgttaac tgtctgcctt tccctaatag attgaaaatt ccttaaatgt agaaacttgg    9180 ccttttttt ttcttccatt gatacatccc ctatacctgg aacagtacct gacgcatggt      9240
aggtgcttaa attttactg ataaatgttg actgataact ggaggcacca ctggtatagt      9300
tttttttttt ttttttttt ttttttttt ttgagacaga gtctcactct gtcgcccagg       9360
ctggagtgca gtggcgcaat ctcggctcac tgcaagctct gcctcccagg ttcacgccat    9420
tctcctgcct cagcctcctg agtagctggg actataggcg cccgccacca cacccggcta    9480 attttttgt attttagta gagacggcgt ttcaccgtgt tagccaggat ggtcttgatc       9540
tcctgacctc gtgatccgtc tgccttggcc tcccaaagtg ctgggattac aggcgtgagc    9600
caccgtgccc ggccaccagt ggtatagtat taatggaatc agtgcattgg cttacgtatc    9660
tgattacagc tcagtaagtg tgtgaccctc actgagcctc agtctcctca tctgaaaaat    9720
gggaatgacc ttcatttcac aaggcttgag ctaaaaacat gtaaagtgta ttgtaaattc    9780
ctgaatgctc tactcatgta agactaaagt aggccgggcg tggtggctca cacctgtaat    9840
tgcagcactt tgggaggccg aggagggcag atcatgaggt caagagatcg agaccatcct    9900
ggctaatatg gtaaaaccct gtctctacta aaaatacaaa aattagctgg gcgtggtggc    9960
gcacatctgt agtcccagct actcaggagg cggaggcagg agaattgctt gaacctggga   10020
ggtggaggtt gcagtgagct gagatcgcgc cactgcattc cagccagtct ggcgaaagag   10080
caagactctg tctcaaaaaa aaaaaaaaa aaaaaaaag actaaagtac atggtttctt      10140
caaagcttct ctctctttct cccaccttag atgattttc ctttgcaatg tcctgtgtcc     10200
attccgcccc actcctcctg gggccacctg gaccaggtct tcatcatctc atatctatat   10260
gtttgctgtg tctcctggct ggccactctt ctgtaatttc tcctcctctg agctctctgg   10320
gcagctgaat cttctcacta gtgaagtcgc ctggttggat gctgatgaga ctgaccagct   10380
gaatccagtt gaaaacttca cacttggcag tgatctggtt ctaaagacac aattttccat   10440
agtttcctaa caccatcctg catgccacct gccttatttc cccacatcac atcgtcccac   10500
ttagcgggac tgcactgctg atccaaattt tacatccttt agggcccact caggtcatat   10560
gtcctcaggg aagtctttct ggaagaacct taaaccagag gttctcaaca gggggcagtt   10620
ttgctccctg tggaacgttt gccaatgtct ggacacattt cattcgtcac aaacggagag   10680
ggggatgcta cagggatctg gcggatagag gccaggatg ctgctgaaca tctgcaatgc    10740
ataggacagc ccaccccac ccccacaccc ccagtaaata atgatccagc ccaagtgtca    10800
ctggtgctga cgttgagtaa ccctatctta agctgaactc atcatctctc cattccagcc   10860
ttggtggatt ctgtctcctc tgaaccattc ccatctcact ttagcctacc tagatcacaa   10920
```

```
agcttggcac tcattataga ctcccctatt tattactcct tcaagatgtg caagaatctt   10980
ttctctgcac ttttaagttc tgtaagaaga gtctgtgtcg ttcctataat aaccagcata   11040
ggacgttgca cgtgttgtgt gctcagtgaa cctggatttg ttgattgttg actgactcac   11100
tctagagttg gaaatcttat gcttggggaa acttaatatc tctttctttc tctgtgtgtg   11160
tgcatttgtg cacgtgtctg tgcatagctg tgagaccaaa gacctggttg tgcaacaggc   11220
aggcacaaac aagactgatg ttgtctgtgg tgagtcctgg acaatgggcc tggagaaag    11280
cctaggaagg tgggaactga agggggagat gaggcacaca ggaacactgg atgggaaaaa   11340
ggggagggga ggcagtttgg gggtgtggta tcacagctct gccacttatc ttgggagtct   11400
gggcaaatca cttcccctct cttagcctca gtttcttcat ctgtaaaatg ggatgataac   11460
agcacttcct tagtaggttt tgattttaga gtgagaaggt tggcctacag taaagatcag   11520
ataatgtaaa tcagtgaaaa aggtcagggg taagaaaatt acattctctt tacctaacgc   11580
taaatgacca gttaatgggt gcagcacacc aacatggtac atgtatacat atgtaacaaa   11640
cctgcacatt atgcacatgt accctaaagc ttaaagtata ataataataa aatttaaaaa   11700
aacgaaaaat acattctctt tgcttttct caaaatgtac tttcctcttt gtagggctgg    11760
gactagaatg aggtgagcaa ggcacttgcc ctcgggcgca atatttaaga aggtgccata   11820
aaagtgtagt aatcaaggta aattcatttt gatgcaatat ttttaaaaat aaaaattaat   11880
gcaaagaaat ccatgatgag caagatagca acatttaaaa taagaacag gatccgaccc    11940
tgtgtttgca tgaccctgcc tcactcacct caccctaatc ctggccctgg ttccagtaaa   12000
aggaataggc agccagcctg caggccgtag tttgctgact tggtgtccgc ctgatgattt   12060
tcaaaatatg gcattaaaag aatgtttacc ttgatgactg agtgttttgg acatccttt    12120
caattttgtc ctgaaacaat ttcatcccctt gcctcacgct agtctccgcc ctgcctttg    12180
gtctttctt tattttccca ctttgaaaaa aaaattcggc atgagaaata ctttaccttt    12240
cccctccact cttctatacc aaaagcaaca tgcagacatg aatcatgcta gacctcggca   12300
ttgggcagag agcagggagt ggcggggagc atggtgagca ggtggtgaca gccactgcca   12360
ccactcgctt ctagatggtt cccaggtggg gaggctgcca actggaaccc agtcttccca   12420
gtttgtaaga gaaatcagat gtctaggttt gaatatgtga tctcccagtt taaaaatgtc   12480
ggcaaatatt tccaaacgtt aagaaaatgt tctggctcct ttaaagacat ctgccagcca   12540
catttcccca aggaccgcgg tttgaacctt ctgatgtaga tgagctctga cattggaaga   12600
ttctggagtc tgacaagtca cagcaggttg agggtaggga gaaactgcag gtgagggtg    12660
catgctgaag tcctgatttc tccaggtccc caggatcggc tgagagccct ggtggtgatc   12720
cccatcatct tcgggatcct gtttgccatc ctcttggtgc tggtctttat cagtgagtcc   12780
tcaggtgggg aggtgttggg ggagggaggg agaccacct gtttcttatc tggcctctcc    12840
aactccccat ccttttttt tttttttttt ttttagaaa aggtggccaa gaagccaacc     12900
aataaggtag gtcaccctg agaacccggg acagagtttt gacaaactgg gaagatggcc    12960
tcacggttgc ctatggggca gtaaaactga ttcagagtct gtctctgcag ccagtggggt   13020
ggcagcagaa ttggggactg tcatccccac ccaccatgcc ccttccatcc agagctcaat   13080
cccccacaga actgcccctg gcaccactgg cagagcctaa cactggctgt tcttcactcc   13140
tttcctggca ttcaacgcgt ggggagctgc atctttgggc cttggggctg gtcaaatgg    13200
gtgggagcaa atgtggcagc cccttaagcc cactggctcc cactctggaa gctcttcgtc   13260
gcccttggtg tggccagcag ggggcaggag gcacccgagg aatcagcact gacccgccgt   13320
```

```
ctgggaaagg ggggagggct tggggaaggg atccgcttcc cagggagggg ctcctcagag   13380
gcacagctgc ccctgctgct gggggtgacc tcacaccttg cctctccagg ccccccaccc   13440
caagcaggaa ccccaggaga tcaattttcc cgacgatctt cctggctcca acactgctgc   13500
tccagtgcag gagactttac atggatgcca accggtcacc caggaggatg gcaaagagag   13560
tcgcatctca gtgcaggaga gacagtgagg ctgcacccac ccaggagtgt ggccacgtgg   13620
gcaaacaggc agttggccag agagcctggt gctgctgctg ctgtggcgtg agggtgaggg   13680
gctggcactg actgggcata gctccccgct tctgcctgca cccctgcagt ttgagacagg   13740
agacctggca ctggatgcag aaacagttca ccttgaagaa cctctcactt caccctggag   13800
cccatccagt ctcccaactt gtattaaaga cagaggcaga agtttggtgg tggtggtgtt   13860
ggggtatggt ttagtaatat ccaccagacc ttccgatcca gcagtttggt gcccagagag   13920
gcatcatggt ggcttccctg cgcccaggaa gccatataca cagatgccca ttgcagcatt   13980
gtttgtgata gtgaacaact ggaagctgct taactgtcca tcagcaggag actggctaaa   14040
taaaattaga atatatttat acaacagaat ctcaaaaaca ctgttgagta aggaaaaaaa   14100
ggcatgctgc tgaatgatgg gtatggaact ttttaaaaaa gtacatgctt ttatgtatgt   14160
atattgccta tggatatatg tataaataca atatgcatca tatattgata taacaagggt   14220
tctggaaggg tacacagaaa acccacagct cgaagagtgg tgacgtctgg ggtggggaag   14280
aagggtctgg gggagggttg gttaaaggga gatttggctt tcccataatg cttcatcatt   14340
tttcccaaaa ggagagtgaa ttcacataat gcttatgtaa ttaaaaaatc atcaaacatg   14400 taaaagaaa acgggggtg aacatgctgg gtgacatgag ctatttaacc tgctgtcagg   14460
ctcacggaat gagggcattt tctgtagata aataagaatg tccccaggct gctgcccctc   14520
cagggtggtt tccatgtgtg ctcacatgtg gtattgagat tgcaaagtgc tcttcccatt   14580
tgattcatgt tcacaaaaat agccttcccc agcagggtgg gtctgcatcc ctccctcttt   14640
tacagaggtg gaaatgaggt ccagagaggc gaagtgactt gcctgtggtc acacagcggt   14700
gtctggtggt gccatgctca gagctcctca ctctgggtcc tgagctcctc ccagatctgc   14760
ctgctgtctg gaactgacat ctgtagctcc ttcccaggga gatcctgggt ctctcaccgc   14820
cttctgacct ccctgtggct gcaggagcta ctgcttctcg gtcagatggt atccccttcc   14880
cccaagcagt atctcaggat aaaaataaac catcctgttc tcttttcctg ctgagccaac   14940
tgagggggag cctagccagg aggagcggca gatggagtgg gagcagaggg gaggggaggg   15000
gaggaaggtt ggaggacaag gaggagaagg aagagcaatg caaagtgcca tgcagaaccc   15060
cggcacaaag gttcgaggtg aggtttaacc caggggtctc agcctttccc aggaaagaac   15120
ctgctttgga tttccccaac acatcctgct ggctggaggg tgtggggcga tgggggcaa   15180 ggggagatgt ggagagggct tatcccagtg gaggctgtga gggcagctgc gagccaagag   15240
aggggcacct ggcttggcag gcttcccaga agagcttcaa gaaccatttg gatacaccag   15300
gtggaggcct ttggtttaga aagtggagca aagtggtggt ggcggggaag gggaactttg   15360
ggacctaatt cttgtctctt atctagagcc taagagtgag tgttgttcac ttctttggtg   15420
gtatggtgga aagagaccaa agaccacgc ctgccacaga tcatctgtgt ggccttggat   15480
gagtcacttt cactgcttca cttctcagtt tccctatctg acaaatggtg acaatatctg   15540
cagcagacgc tattgatgcc tcctgtgttc tcttctaggt cagagcttct caaatttgag   15600
tgtgggtcag gcgcagtggc tcacgtctgt aatcccagca ctctgggagg cttaggtggg   15660
```

| | | | |
|---|---|---|---|
| cagataacct | aaggtcagga | gttcgagacc | agcctgacca acagggcaaa acccgtctc | 15720 |
| tactaaaaat | acaaaaatta | gccgggcatg | atggcgggtg cctgtaatcc cagctacttg | 15780 |
| ggaggctgag | gcagaagaat | cacttgaacc | cgggaggtgg aggttgcagt gagccgagat | 15840 |
| catgccactg | tactccagcc | tgggcaacag | agtgaaactc catctaaaat aacaacaaca | 15900 |
| acaatagcaa | caacaacaac | aacaatagca | acaacaacaa aacttgagcg tgtatctgga | 15960 |
| ccacctgcaa | ggtggtcctc | tccactattt | tcagaactgg a | 16001 |

```
<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 5
ccaggcggca ggaccact                                                  18

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 6
gaccaggcgg caggacca                                                  18

<210> SEQ ID NO 7
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 7
aggtgagacc aggcggca                                                  18

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
cagaggcaga cgaaccat                                                  18

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
gcagaggcag acgaacca                                                  18

<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 10
gcaagcagcc ccagagga                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
ggtcagcaag cagcccca                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
gacagcggtc agcaagca                                                 18

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
gatggacagc ggtcagca                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 14
tctggatgga cagcggtc                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 15
ggtggttctg gatggaca                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
gtgggtggtt ctggatgg                                                 18

<210> SEQ ID NO 17
```

```
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
gcagtgggtg gttctgga                                                   18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
cacaaagaac agcactga                                                   18

<210> SEQ ID NO 19
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 19
ctggcacaaa gaacagca                                                   18

<210> SEQ ID NO 20
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 20
tcctggctgg cacaaaga                                                   18

<210> SEQ ID NO 21
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 21
ctgtcctggc tggcacaa                                                   18

<210> SEQ ID NO 22
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 22
ctcaccagtt tctgtcct                                                   18

<210> SEQ ID NO 23
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 23
```

-continued tcactcacca gtttctgt                                               18

<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 24
gtgcagtcac tcaccagt                                               18

<210> SEQ ID NO 25
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 25
actctgtgca gtcactca                                               18

<210> SEQ ID NO 26
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 26
cagtgaactc tgtgcagt                                               18

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
attccgtttc agtgaact                                               18

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
gaaggcattc cgtttcag                                               18

<210> SEQ ID NO 29
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 29
ttcaccgcaa ggaaggca                                               18

<210> SEQ ID NO 30
<211> LENGTH: 18
<212> TYPE: DNA

```
<213> ORGANISM: Artificial Sequence
<220> FEATURE:
<223> OTHER INFORMATION: Synthetic Oligonucleotide

<400> SEQUENCE: 30
ctctgttcca ggtgtcta                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 31
ctggtggcag tgtgtctc                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 32
tggggtcgca gtatttgt                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 33
ggttggggtc gcagtatt                                                 18

<210> SEQ ID NO 34
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 34
ctaggttggg gtcgcagt                                                 18

<210> SEQ ID NO 35
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 35
ggtgcccttc tgctggac                                                 18

<210> SEQ ID NO 36
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 36
ctgaggtgcc cttctgct                                                 18
```

<210> SEQ ID NO 37
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 37
gtgtctgttt ctgaggtg                                                 18

<210> SEQ ID NO 38
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 38
tggtgtctgt ttctgagg                                                 18

<210> SEQ ID NO 39
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 39
acaggtgcag atggtgtc                                                 18

<210> SEQ ID NO 40
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 40
ttcacaggtg cagatggt                                                 18

<210> SEQ ID NO 41
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 41
gtgccagcct tcttcaca                                                 18

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 42
tacagtgcca gccttctt                                                 18

<210> SEQ ID NO 43
<211> LENGTH: 18
<212> TYPE: DNA
<213> ORGANISM: Artificial Sequence
<220> FEATURE:

<223> OTHER INFORMATION: Synthetic Oligonucleotide

<400> SEQUENCE: 43
ggacacagct ctcacagg                                                    18

<210> SEQ ID NO 44
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 44
tgcaggacac agctctca                                                    18

<210> SEQ ID NO 45
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 45
gagcggtgca ggacacag                                                    18

<210> SEQ ID NO 46
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 46
aagccgggcg agcatgag                                                    18

<210> SEQ ID NO 47
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 47
aatctgcttg accccaaa                                                    18

<210> SEQ ID NO 48
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 48
gaaacccctg tagcaatc                                                    18

<210> SEQ ID NO 49
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 49
gtatcagaaa cccctgta                                                    18

```
<210> SEQ ID NO 50
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 50
gctcgcagat ggtatcag                                                 18

<210> SEQ ID NO 51
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 51
gcagggctcg cagatggt                                                 18

<210> SEQ ID NO 52
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 52
tgggcagggc tcgcagat                                                 18

<210> SEQ ID NO 53
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 53
gactgggcag ggctcgca                                                 18

<210> SEQ ID NO 54
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 54
cattggagaa gaagccga                                                 18

<210> SEQ ID NO 55
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 55
gatgacacat tggagaag                                                 18

<210> SEQ ID NO 56
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 56
gcagatgaca cattggag                                                 18

<210> SEQ ID NO 57
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 57
tcgaaagcag atgcaca                                                  18

<210> SEQ ID NO 58
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 58
gtccaagggt gacatttt                                                 18

<210> SEQ ID NO 59
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 59
cacagcttgt ccaagggt                                                 18

<210> SEQ ID NO 60
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 60
ttggtctcac agcttgtc                                                 18

<210> SEQ ID NO 61
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 61
caggtctttg gtctcaca                                                 18

<210> SEQ ID NO 62
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 62
ctgttgcaca accaggtc                                                 18

<210> SEQ ID NO 63
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 63
gtttgtgcct gcctgttg                                                     18

<210> SEQ ID NO 64
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 64
gtcttgtttg tgcctgcc                                                     18

<210> SEQ ID NO 65
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 65
ccacagacaa catcagtc                                                     18

<210> SEQ ID NO 66
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 66
ctggggacca cagacaac                                                     18

<210> SEQ ID NO 67
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 67
tcagccgatc ctggggac                                                     18

<210> SEQ ID NO 68
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 68
caccaccagg gctctcag                                                     18

<210> SEQ ID NO 69
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 69
```
gggatcacca ccagggct                                              18

<210> SEQ ID NO 70
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 70
gaggatggca aacaggat                                              18

<210> SEQ ID NO 71
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 71
accagcacca agaggatg                                              18

<210> SEQ ID NO 72
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 72
ttttgataaa gaccagca                                              18

<210> SEQ ID NO 73
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 73
tattggttgg cttcttgg                                              18

<210> SEQ ID NO 74
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 74
gggttcctgc ttggggtg                                              18

<210> SEQ ID NO 75
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 75
gtcgggaaaa ttgatctc                                              18

<210> SEQ ID NO 76
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 76
gatcgtcggg aaaattga                                                   18

<210> SEQ ID NO 77
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 77
ggagccagga agatcgtc                                                   18

<210> SEQ ID NO 78
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 78
tggagccagg aagatcgt                                                   18

<210> SEQ ID NO 79
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 79
tggagcagca gtgttgga                                                   18

<210> SEQ ID NO 80
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 80
gtaaagtctc ctgcactg                                                   18

<210> SEQ ID NO 81
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 81
tggcatccat gtaaagtc                                                   18

<210> SEQ ID NO 82
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 82
cggttggcat ccatgtaa                                                   18
```

<210> SEQ ID NO 83
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 83
ctctttgcca tcctcctg                                                 18

<210> SEQ ID NO 84
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 84
ctgtctctcc tgcactga                                                 18

<210> SEQ ID NO 85
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 85
ggtgcagcct cactgtct                                                 18

<210> SEQ ID NO 86
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 86
aactgcctgt ttgcccac                                                 18

<210> SEQ ID NO 87
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 87
cttctgcctg cacccctg                                                 18

<210> SEQ ID NO 88
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 88
actgactggg catagctc                                                 18

<210> SEQ ID NO 89
<211> LENGTH: 18
<212> TYPE: DNA
<213> ORGANISM: Artificial Sequence
<220> FEATURE:
<223> OTHER INFORMATION: Synthetic Oligonucleotide

```
<400> SEQUENCE: 89
gccccagagg acgcactg                                               18

<210> SEQ ID NO 90
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 90
agcagcccca gaggacgc                                               18

<210> SEQ ID NO 91
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 91
agcaagcagc cccagagg                                               18

<210> SEQ ID NO 92
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 92
gcggtcagca agcagccc                                               18

<210> SEQ ID NO 93
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 93
ggttctggat ggacagcg                                               18

<210> SEQ ID NO 94
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 94
agtgggtggt tctggatg                                               18

<210> SEQ ID NO 95
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 95
gcactgactg tttattag                                               18

<210> SEQ ID NO 96
```

```
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 96
ggcacaaaga acagcact                                                    18

<210> SEQ ID NO 97
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 97
tgtcctggct ggcacaaa                                                    18

<210> SEQ ID NO 98
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 98
cagtttctgt cctggctg                                                    18

<210> SEQ ID NO 99
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 99
gtcactcacc agtttctg                                                    18

<210> SEQ ID NO 100
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 100
aaggcattcc gtttcagt                                                    18

<210> SEQ ID NO 101
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 101
ctttcaccgc aaggaagg                                                    18

<210> SEQ ID NO 102
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 102
```
tgtgtctctc tgttccag                                                  18

<210> SEQ ID NO 103
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 103
gtggcagtgt gtctctct                                                  18

<210> SEQ ID NO 104
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 104
cccttctgct ggacccga                                                  18

<210> SEQ ID NO 105
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 105
tgaggtgccc ttctgctg                                                  18

<210> SEQ ID NO 106
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 106
tctgtttctg aggtgccc                                                  18

<210> SEQ ID NO 107
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 107
gatggtgtct gtttctga                                                  18

<210> SEQ ID NO 108
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 108
aaacccctgt agcaatct                                                  18

<210> SEQ ID NO 109
<211> LENGTH: 18
<212> TYPE: DNA

```
<213> ORGANISM: Artificial Sequence
<220> FEATURE:
<223> OTHER INFORMATION: Synthetic Oligonucleotide

<400> SEQUENCE: 109
cgcagatggt atcagaaa                                                 18

<210> SEQ ID NO 110
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 110
ggcagggctc gcagatgg                                                 18

<210> SEQ ID NO 111
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 111
gagaagaagc cgactggg                                                 18

<210> SEQ ID NO 112
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 112
tggagaagaa gccgactg                                                 18

<210> SEQ ID NO 113
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 113
attggagaag aagccgac                                                 18

<210> SEQ ID NO 114
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 114
acattggaga agaagccg                                                 18

<210> SEQ ID NO 115
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 115
acacattgga gaagaagc                                                 18
```

<210> SEQ ID NO 116
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 116
tgacacattg gagaagaa                                                 18

<210> SEQ ID NO 117
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 117
atgacacatt ggagaaga                                                 18

<210> SEQ ID NO 118
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 118
aaagcagatg acacattg                                                 18

<210> SEQ ID NO 119
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 119
aggtctttgg tctcacag                                                 18

<210> SEQ ID NO 120
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 120
ttgcacaacc aggtcttt                                                 18

<210> SEQ ID NO 121
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 121
ttgtttgtgc ctgcctgt                                                 18

<210> SEQ ID NO 122
<211> LENGTH: 18
<212> TYPE: DNA
<213> ORGANISM: Artificial Sequence
<220> FEATURE:

```
<223> OTHER INFORMATION: Synthetic Oligonucleotide

<400> SEQUENCE: 122
tcttgtttgt gcctgcct                                                 18

<210> SEQ ID NO 123
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 123
agtcttgttt gtgcctgc                                                 18

<210> SEQ ID NO 124
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 124
cagtcttgtt tgtgcctg                                                 18

<210> SEQ ID NO 125
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 125
tcagtcttgt ttgtgcct                                                 18

<210> SEQ ID NO 126
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 126
catcagtctt gtttgtgc                                                 18

<210> SEQ ID NO 127
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 127
gaccacagac aacatcag                                                 18

<210> SEQ ID NO 128
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 128
gggaccacag acaacatc                                                 18
```

```
<210> SEQ ID NO 129
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 129
tcaccaccag ggctctca                                                 18

<210> SEQ ID NO 130
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 130
gatcaccacc agggctct                                                 18

<210> SEQ ID NO 131
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 131
agaggatggc aaacagga                                                 18

<210> SEQ ID NO 132
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 132
aagaggatgg caaacagg                                                 18

<210> SEQ ID NO 133
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 133
caagaggatg gcaaacag                                                 18

<210> SEQ ID NO 134
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 134
gaccagcacc aagaggat                                                 18

<210> SEQ ID NO 135
<211> LENGTH: 18
<212> TYPE: DNA
<213> ORGANISM: Artificial Sequence
<220> FEATURE:
<223> OTHER INFORMATION: Synthetic Oligonucleotide
```

```
<400> SEQUENCE: 135
aagaccagca ccaagagg                                                  18

<210> SEQ ID NO 136
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 136
taaagaccag caccaaga                                                  18

<210> SEQ ID NO 137
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 137
tgataaagac cagcacca                                                  18

<210> SEQ ID NO 138
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 138
tttgataaag accagcac                                                  18

<210> SEQ ID NO 139
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 139
actctctttg cccatcct                                                  18

<210> SEQ ID NO 140
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 140
cgactctctt tgcccatc                                                  18

<210> SEQ ID NO 141
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 141
atgcgactct ctttgccc                                                  18

<210> SEQ ID NO 142
<211> LENGTH: 18
```

```
<212> TYPE: DNA
<213> ORGANISM: Artificial Sequence
<220> FEATURE:
<223> OTHER INFORMATION: Synthetic Oligonucleotide

<400> SEQUENCE: 142
aaatgcgact ctctttgc                                                      18

<210> SEQ ID NO 143
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 143
ctgaaatgcg actctctt                                                      18

<210> SEQ ID NO 144
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 144
aactgaaatg cgactctc                                                      18

<210> SEQ ID NO 145
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 145
cttcactgtc tctccctg                                                      18

<210> SEQ ID NO 146
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 146
ccttcactgt ctctccct                                                      18

<210> SEQ ID NO 147
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 147
aaccttcact gtctctcc                                                      18

<210> SEQ ID NO 148
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 148
```

-continued gatcaccaca ggctctca                                           18

<210> SEQ ID NO 149
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 149
tgataagaca gcaccaag                                           18

<210> SEQ ID NO 150
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 150
ggtagttctt gccacttt                                           18

<210> SEQ ID NO 151
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 151
gggcctatgg gtagttct                                           18

<210> SEQ ID NO 152
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 152
attatctctg ggtctgct                                           18

<210> SEQ ID NO 153
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 153
actgacacat ttgagcag                                           18

<210> SEQ ID NO 154
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 154
gactccctac tgacacat                                           18

<210> SEQ ID NO 155
<211> LENGTH: 18
<212> TYPE: DNA
<213> ORGANISM: Artificial Sequence

```
<220> FEATURE:
<223> OTHER INFORMATION: Synthetic Oligonucleotide

<400> SEQUENCE: 155
caaagagcgg ttctccac                                                    18

<210> SEQ ID NO 156
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 156
aattctccaa agagcggt                                                    18

<210> SEQ ID NO 157
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 157
tcttgacatc cttttcat                                                    18

<210> SEQ ID NO 158
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 158
cccacctatc ttgacatc                                                    18

<210> SEQ ID NO 159
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 159
aggccgagag ttcaaaat                                                    18

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 160
ccagcaattc accgcgcagg                                                  20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
tgcagaggca gacgaaccat                                                  20
```

```
<210> SEQ ID NO 162
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 162
cagaggacgc actgcagagg                                                   20

<210> SEQ ID NO 163
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 163
aagcagcccc agaggacgca                                                   20

<210> SEQ ID NO 164
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 164
cagcggtcag caagcagccc                                                   20

<210> SEQ ID NO 165
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 165
ctcacagcgg tcagcaagca                                                   20

<210> SEQ ID NO 166
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 166
gctggcaagg agatgataac                                                   20

<210> SEQ ID NO 167
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 167
aggttggaac acccaagata                                                   20

<210> SEQ ID NO 168
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 168
ggagaaaccc ctggtttctc                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 169
tcattcctgc ccaggcttca                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 170
tcaggtgaaa gtgaaagctg                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 171
taccatcttc aaacacatga                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 172
ttacccaaaa tgggaaagga                                               20

<210> SEQ ID NO 173
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 173
gaaagaatac atgtatatgg                                               20

<210> SEQ ID NO 174
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 174
agagtcagac agctttagac                                               20

<210> SEQ ID NO 175

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 175
gtaccaccca tgctattaat                                              20

<210> SEQ ID NO 176
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 176
acagtgacag agtccaaatg                                              20

<210> SEQ ID NO 177
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 177
aatgtaaagc tggaagggta                                              20

<210> SEQ ID NO 178
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 178
gggctatgtt tagcacttgg                                              20

<210> SEQ ID NO 179
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 179
gggcttgatg cctgagtcat                                              20

<210> SEQ ID NO 180
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 180
tgaagtgcaa gtcaaaacag                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 181
```
gcaatttgaa gggatcttga                                        20

<210> SEQ ID NO 182
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 182
catgcagtgg gtggttctgg                                        20

<210> SEQ ID NO 183
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 183
gtttttctct gcatgcagtg                                        20

<210> SEQ ID NO 184
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 184
gctggcacaa agaacagcac                                        20

<210> SEQ ID NO 185
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 185
cactaaccac acaatgatca                                        20

<210> SEQ ID NO 186
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 186
tgtgcagtca ctcaccagtt                                        20

<210> SEQ ID NO 187
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 187
gtctaggaat tcgctttcac                                        20

<210> SEQ ID NO 188
<211> LENGTH: 20
<212> TYPE: DNA

```
<213> ORGANISM: Artificial Sequence
<220> FEATURE:
<223> OTHER INFORMATION: Synthetic Oligonucleotide

<400> SEQUENCE: 188
caggtgtcta ggaattcgct                                              20

<210> SEQ ID NO 189
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 189
gtcgcagtat ttgtgctggt                                              20

<210> SEQ ID NO 190
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 190
acccgaagcc ctaggtctga                                              20

<210> SEQ ID NO 191
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 191
ctggacccga agccctaggt                                              20

<210> SEQ ID NO 192
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 192
ttctgctgga cccgaagccc                                              20

<210> SEQ ID NO 193
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 193
cttcttcaca ggtgcagatg                                              20

<210> SEQ ID NO 194
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 194
agccagtggc caggcaggac                                              20
```

<210> SEQ ID NO 195
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 195
gaagaagccg actgggcagg                                                    20

<210> SEQ ID NO 196
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 196
ttggagaaga agccgactgg                                                    20

<210> SEQ ID NO 197
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 197
gatgacacat tggagaagaa                                                    20

<210> SEQ ID NO 198
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 198
tgtctattac ctcaaagaga                                                    20

<210> SEQ ID NO 199
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 199
acagtgtgtt cagaggattg                                                    20

<210> SEQ ID NO 200
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 200
acaatacact ttacatgttt                                                    20

<210> SEQ ID NO 201
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 201
attgtgtctt tagaaccaga                                          20

<210> SEQ ID NO 202
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 202
gggccctaaa ggatgtaaaa                                          20

<210> SEQ ID NO 203
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 203
cagtcttgtt tgtgcctgcc                                          20

<210> SEQ ID NO 204
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 204
tgtccaggac tcaccacaga                                          20

<210> SEQ ID NO 205
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 205
tatggcacct tcttaaatat                                          20

<210> SEQ ID NO 206
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 206
tgcttttggt atagaagagt                                          20

<210> SEQ ID NO 207
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 207
aaatgtggct ggcagatgtc                                          20

```
<210> SEQ ID NO 208
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 208
gtcagagctc atctacatca                                                   20

<210> SEQ ID NO 209
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 209
ctgataaaga ccagcaccaa                                                   20

<210> SEQ ID NO 210
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 210
aggactcact gataaagacc                                                   20

<210> SEQ ID NO 211
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 211
cagactctga atcagtttta                                                   20

<210> SEQ ID NO 212
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 212
cagtccccaa ttctgctgcc                                                   20

<210> SEQ ID NO 213
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 213
ccagtgttag gctctgccag                                                   20

<210> SEQ ID NO 214
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 214
gaatgccagg aaaggagtga                                           20

<210> SEQ ID NO 215
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 215
cagccccaag gcccaaagat                                           20

<210> SEQ ID NO 216
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 216
ctgcactgga gcagcagtgt                                           20

<210> SEQ ID NO 217
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 217
accggttggc atccatgtaa                                           20

<210> SEQ ID NO 218
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 218
cctgggtgac cggttggcat                                           20

<210> SEQ ID NO 219
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 219
caagttggga gactggatgg                                           20

<210> SEQ ID NO 220
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 220
ctttaataca agttgggaga                                           20

<210> SEQ ID NO 221
<211> LENGTH: 20

```
<212> TYPE: DNA
<213> ORGANISM: Artificial Sequence
<220> FEATURE:
<223> OTHER INFORMATION: Synthetic Oligonucleotide

<400> SEQUENCE: 221
tcggaaggtc tggtggatat                                              20

<210> SEQ ID NO 222
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 222
tgggcaccaa actgctggat                                              20

<210> SEQ ID NO 223
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 223
tatggcttcc tgggcgcagg                                              20

<210> SEQ ID NO 224
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 224
aatgctgcaa tgggcatctg                                              20

<210> SEQ ID NO 225
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 225
gttcactatc acaaacaatg                                              20

<210> SEQ ID NO 226
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 226
cagttaagca gcttccagtt                                              20

<210> SEQ ID NO 227
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 227
```
aattttattt agccagtctc                                               20

<210> SEQ ID NO 228
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 228
gttgtataaa tatattctaa                                               20

<210> SEQ ID NO 229
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 229
acagtgtttt tgagattctg                                               20

<210> SEQ ID NO 230
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 230
ctcaggaccc agagtgagga                                               20

<210> SEQ ID NO 231
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 231
tgggttaaac ctcacctcga                                               20

<210> SEQ ID NO 232
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 232
attaggtccc aaagttcccc                                               20

<210> SEQ ID NO 233
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 233
ggcagacgaa ccatggcgag                                               20

<210> SEQ ID NO 234
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 234
gtagcaatct gcttgacccc                                                  20

<210> SEQ ID NO 235
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 235
gaccacagac aacatcagtc                                                  20

<210> SEQ ID NO 236
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 236 ccacctttt  gataaagacc                                                  20

<210> SEQ ID NO 237
<211> LENGTH: 1570
<212> TYPE: DNA
<213> ORGANISM: H. sapiens

<400> SEQUENCE: 237
ggcaggggag tcagcagagg cctcgctcgg gcgcccagtg gtcctgccgc ctggtctcac      60
ctcgccatgg ttcgtctgcc tctgcagtgc gtcctctggg gctgcttgct gaccgctgtc     120
catccagaac cacccactgc atgcagagaa aaacagtacc taataaacag tcagtgctgt     180
tctttgtgcc agccaggaca gaaactggtg agtgactgca cagagttcac tgaaacggaa     240
tgccttcctt gcggtgaaag cgaattccta gacacctgga acagagagac acacttccac     300
cagcacaaat actgcgaccc caacctaggg cttcgggtcc agcagaaggg cacctcagaa     360
acagacacca tctgcacctg tgaagaaggc tggcactgta cgagtgaggc ctgtgagagc     420
tgtgtcctgc accgctcatg ctcgcccggc tttggggtca gcagattga  catctgccag     480
ccacatttcc ccaaggaccg cggtttgaac cttctgatgt agatgagctc tgacattgga     540
agattctgga gtctgacaag tcacagcagg ttgagggtag ggagaaactg caggtgaggg     600
gtgcatgctg aagtcctgat ttctccaggt ccccaggatc ggctgagagc cctggtggtg     660
atccccatca tcttcgggat cctgtttgcc atcctcttgg tgctggtctt tatcaaaaag     720
gtggccaaga agccaaccaa taaggccccc caccccaagc aggaacccca ggagatcaat     780
tttcccgacg atcttcctgg ctccaacact gctgctccag tgcaggagac tttacatgga     840
tgccaaccgg tcacccagga ggatggcaaa gagagtcgca tctcagtgca ggagagacag     900
tgaggctgca cccacccagg agtgtggcca cgtgggcaaa caggcagttg ccagagagc      960
ctggtgctgc tgctgctgtg gcgtgagggt gaggggctgg cactgactgg gcatagctcc    1020
ccgcttctgc ctgcacccct gcagtttaga caggagacct ggcactggat gcagaaacag    1080
ttcaccttga agaacctctc acttcaccct ggagcccatc cagtctccca acttgtatta    1140
aagacagagg cagaagtttg gtggtggtgg tgttggggta tggtttagta atatccacca    1200
```

```
gaccttccga tccagcagtt tggtgcccag agaggcatca tggtggcttc cctgcgccca   1260
ggaagccata tacacagatg cccattgcag cattgtttgt gatagtgaac aactggaagc   1320
tgcttaactg tccatcagca ggagactggc taaataaaat tagaatatat ttatacaaca   1380
gaatctcaaa aacactgttg agtaaggaaa aaaaggcatg ctgctgaatg atgggtatgg   1440
aactttttaa aaaagtacat gcttttatgt atgtatattg cctatggata tatgtataaa   1500
tacaatatgc atcatatatt gataaaaaaa aaaaaaaaaa aaaaaaaaaa aaaaaaaaaa   1560
aaaaaaaaaa                                                         1570

<210> SEQ ID NO 238
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 238
tccatttatt agtctaggaa                                                20
```